(12) United States Patent
Schmidt et al.

(10) Patent No.: US 6,570,057 B1
(45) Date of Patent: May 27, 2003

(54) ABSORBENT ARTICLES WITH IMPROVED DISTRIBUTION PROPERTIES UNDER SUR-SATURATION

(75) Inventors: Mattias Schmidt, Idstein (DE); Bruno Johannes Ehrnsperger, Frankfurt (DE); Fred Desai, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/646,090

(22) PCT Filed: Mar. 13, 1998

(86) PCT No.: PCT/US98/05040

§ 371 (c)(1),
(2), (4) Date: Sep. 13, 2000

(87) PCT Pub. No.: WO99/45875

PCT Pub. Date: Sep. 16, 1999

(51) Int. Cl.[7] .................................................. A61F 13/15
(52) U.S. Cl. ..................................................... 604/378
(58) Field of Search ................................ 604/368, 369, 604/367, 385.01, 385.23, 378

(56) References Cited

U.S. PATENT DOCUMENTS

| | | | |
|---|---|---|---|
| 3,575,174 A | 4/1971 | Mogor | 128/290 |
| 3,952,745 A | 4/1976 | Duncan | 125/287 |
| 4,020,780 A | 5/1977 | Shumaker et al. | 114/243 |
| 4,076,663 A | 2/1978 | Masuda et al. | 260/17.4 |
| 4,440,597 A | 4/1984 | Wells et al. | 162/111 |
| 4,578,068 A | 3/1986 | Kramer et al. | 604/368 |
| 4,610,678 A | 9/1986 | Weisman et al. | 604/368 |
| 4,737,582 A * | 4/1988 | Goldman et al. | 536/2 |
| 4,773,903 A * | 9/1988 | Weisman et al. | 604/368 |
| 4,781,710 A | 11/1988 | Megison et al. | 604/378 |
| 4,898,642 A | 2/1990 | Moore et al. | 162/157 |
| 5,061,259 A | 10/1991 | Goldman et al. | 604/368 |
| 5,117,540 A | 6/1992 | Walton et al. | 26/18.6 |
| 5,244,482 A | 9/1993 | Hassenboehler, Jr. et al. | 55/528 |
| 5,268,224 A | 12/1993 | DesMarais et al. | 428/286 |
| 5,290,820 A | 3/1994 | Brownscombe et al. | 521/64 |
| 5,352,711 A | 10/1994 | DesMarais | 521/149 |
| 5,387,207 A | 2/1995 | Dyer et al. | 604/369 |
| 5,468,536 A * | 11/1995 | Whitcomb et al. | 428/98 |
| H1511 H | 12/1995 | Chappell et al. | 604/383 |
| 5,549,589 A | 8/1996 | Horney et al. | 604/366 |
| 5,563,179 A | 10/1996 | Stone et al. | 521/64 |
| 5,583,162 A | 12/1996 | Li et al. | 521/56 |
| 5,599,335 A | 2/1997 | Goldman et al. | 604/368 |
| 5,650,222 A | 7/1997 | DesMarais et al. | 442/370 |
| 5,653,922 A | 8/1997 | Li et al. | 264/4.3 |
| 5,662,646 A | 9/1997 | Fumich | 606/15 |
| 5,786,395 A * | 7/1998 | Stone et al. | 521/64 |
| 5,851,648 A * | 12/1998 | Stone et al. | 12/98 |
| 6,013,589 A * | 1/2000 | DesMarais et al. | 442/370 |
| 6,083,211 A * | 7/2000 | DesMarais | 604/369 |
| 6,107,356 A * | 8/2000 | DesMarais | 521/62 |
| 6,107,538 A * | 8/2000 | Young et al. | 604/369 |
| 6,121,509 A * | 9/2000 | Ashraf et al. | 604/368 |
| 6,372,953 B1 * | 4/2002 | Young et al. | 604/369 |
| 6,426,445 B1 * | 7/2002 | Young et al. | 604/368 |
| 6,506,960 B1 * | 1/2003 | Young et al. | 604/378 |

FOREIGN PATENT DOCUMENTS

| | | | |
|---|---|---|---|
| EP | 0 343 941 B1 | 4/1994 | A61F/13/46 |
| EP | 0 397 110 B1 | 7/1996 | A61F/13/46 |
| EP | 0 809 991 A1 | 12/1997 | A61F/13/15 |
| EP | 0 810 078 A1 | 12/1997 | B29C/55/18 |
| EP | 0 640 330 B1 | 5/2000 | A61F/13/46 |
| WO | WO 97/05046 | 2/1997 | B65G/17/42 |
| WO | WO 97/38654 | 10/1997 | A61F/13/15 |

* cited by examiner

*Primary Examiner*—Weilun Lo
*Assistant Examiner*—Michael Bogart
(74) *Attorney, Agent, or Firm*—Eileen L. Hughett; Edward J. Milbrada; Ken K. Patel

(57) ABSTRACT

An absorbent article contains at least one fluid storage member and at least one fluid distribution member. The fluid distribution member has an improved fluid handling property especially under sub-saturation conditions. Such members exhibit, at 50% of their saturation capacity, an increased permeability of at least about 14% of one at saturation. The fluid storage member has a higher Capillary Sorption Absorbency Height than the fluid distribution member.

36 Claims, 7 Drawing Sheets

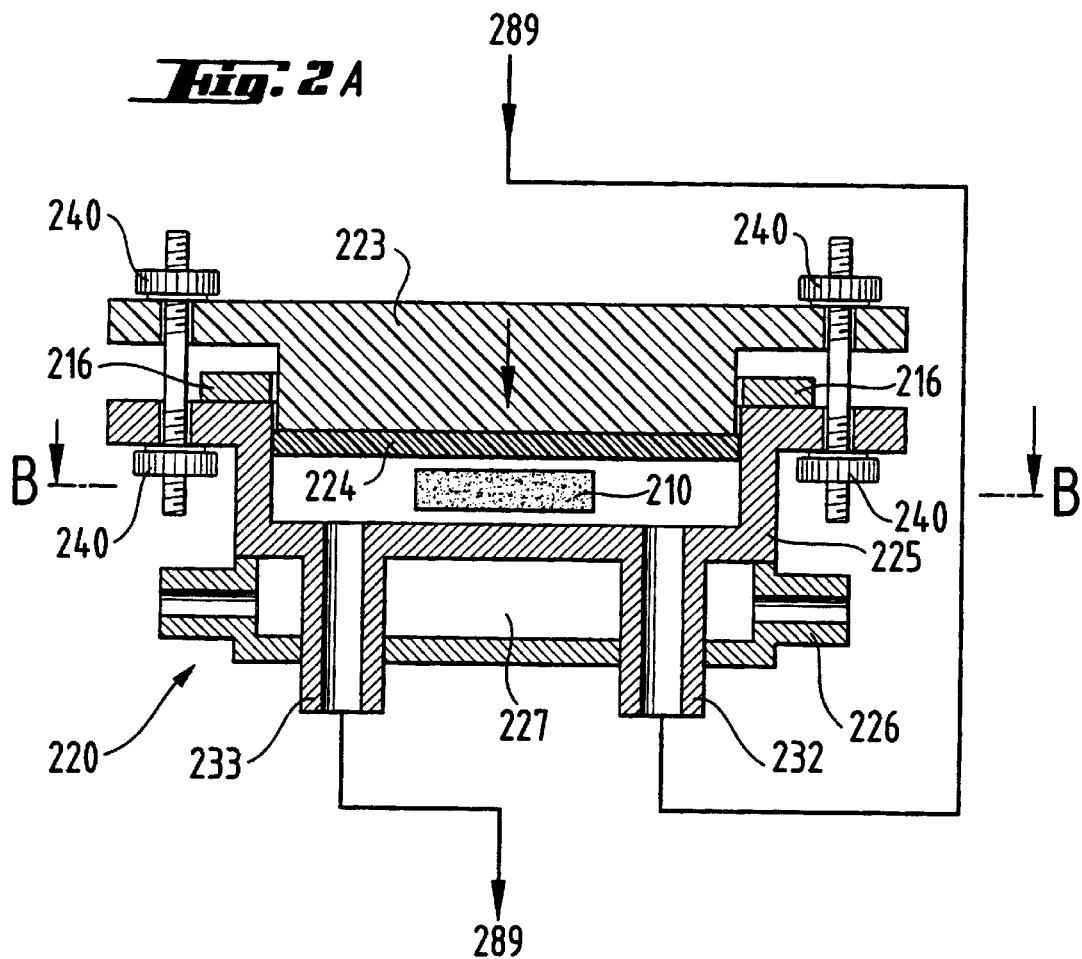
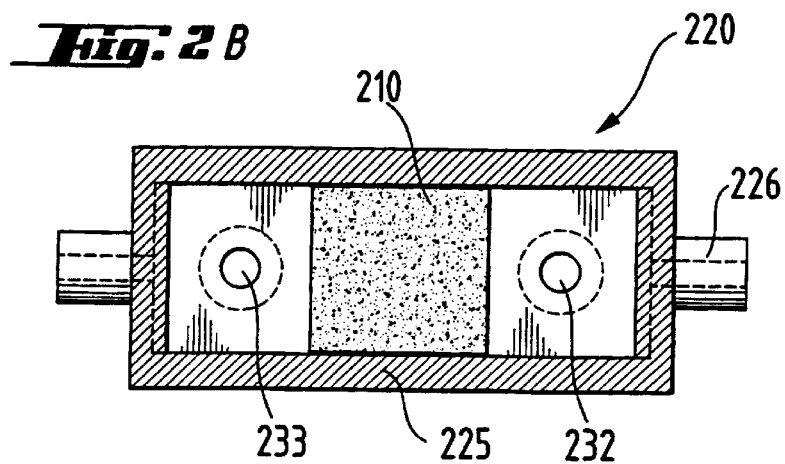

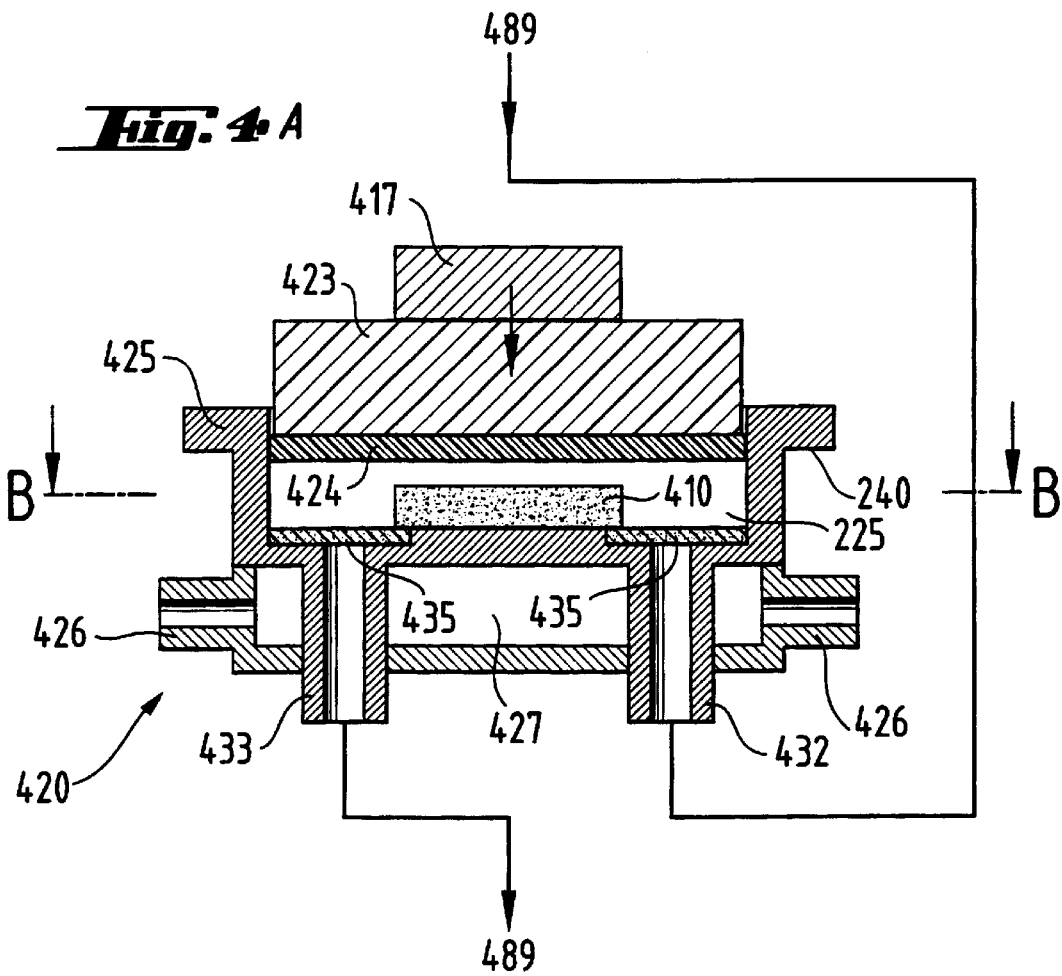
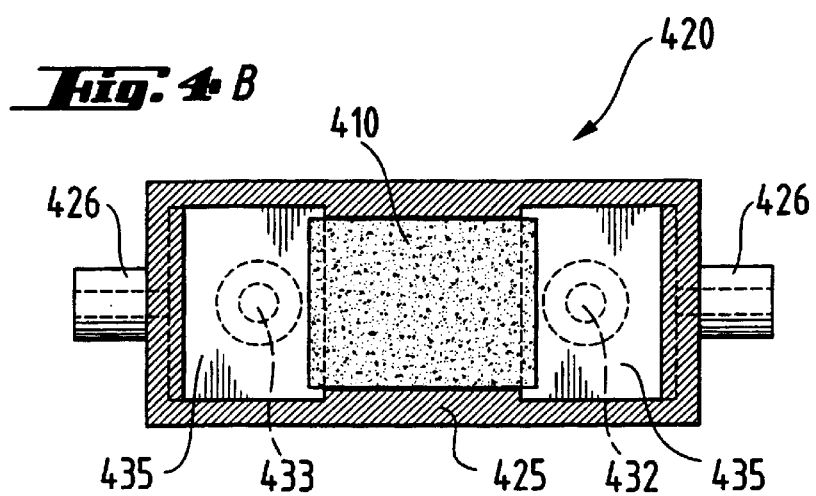

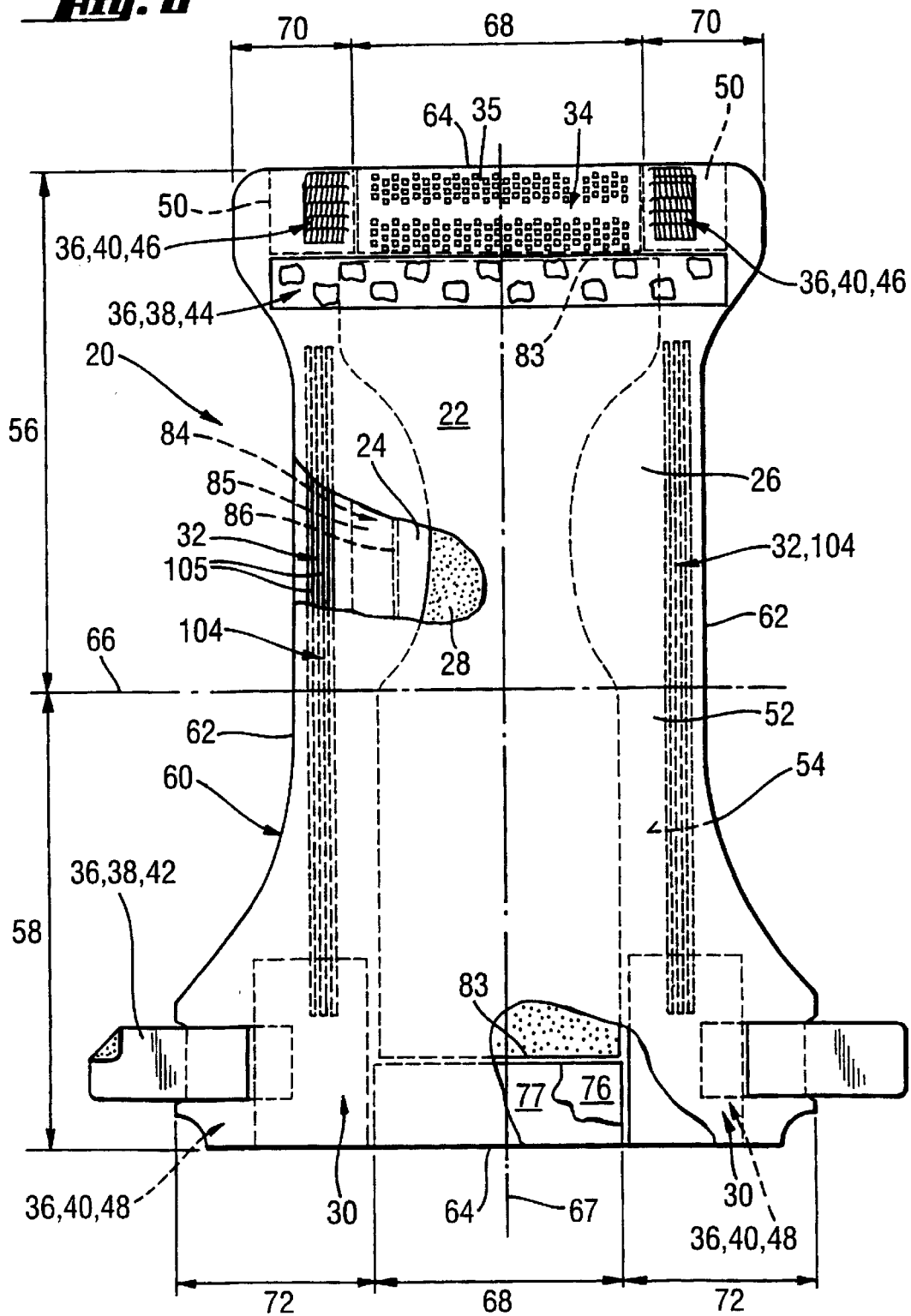

ABSORBENT ARTICLES WITH IMPROVED DISTRIBUTION PROPERTIES UNDER SUR-SATURATION

GENERAL FIELD OF THE INVENTION

The present invention relates to hygienic absorbent articles, such as disposable baby diapers, training pants, adult incontinence articles, feminine hygiene articles and the like, which comprise fluid distribution members exhibiting an improved performance for distributing liquid within such articles.

BACKGROUND/PRIOR ART

In the general field of disposable absorbent articles and structures, materials exhibiting specific fluid distribution properties are well known. Such materials became more and more relevant with the introduction of highly absorbent materials, also called Absorbent Gelling Materials or superabsorbent materials or shortly superabsorber, which do provide a good means for storing aqueous fluids such as urine, but do not enhance fluid transport, and even reduction of fluid transport can occur, when, sub-optimal designs and/or suboptimal materials are employed, and phenomena often referred to as "gel-blocking" take place. For example, in structures where the superabsorbent is homogeneously mixed with cellulose fibers, a certain critical concentration, which is strongly depending on the choice of the superabsorbent material, should not be exceeded in order to not deteriorate efficacy of the absorbent core.

As a consequence, a vast number of absorbent core designs have appeared with a separated functionality, such as by comprising not only liquid storage regions or materials, but also regions with specialized properties for enhanced acquisition and/or distribution of the fluid. Often, one region aimed at enhancing acquisition and distribution at the same time.

Initially, the requirements for a distribution material were not very high, and standard paper tissue materials such as used as wrapsheets in the cores and described for example in U.S. Pat. No. 3,952,745 (Duncan), were applied to also enhance the fluid distribution, as described in EP-0 343 941 (Reising) or U.S. Pat. No. 4,578,068 (Kramer).

Further developments can be exemplified by EP-A-0,397,110 (Latimer) disclosing an absorbent article comprising a surge management portion for improved fluid handling, having specific basis weights, acquisition times and residual wetness; U.S. Pat. No. 4,898,642 (Moore et al.) discloses specially twisted, chemically stiffened cellulosic fibers and absorbent structures made therefrom; EP-A-0,640,330 (Bewick-Sonntag et al.) discloses the use of such fibers in a specific arrangement with specific superabsorbent materials.

Further approaches aimed at improving the wicking properties of cellulose fiber based materials, such as U.S. Pat. Nos. 3,575,174 or 4,781,710, whereby parts of the structure are compressed to a higher density, thus creating smaller pores for increased wicking height for example along "wicking lines" or in closed mesh patterns.

As some of these materials did exhibit an undesired hard feel, methods for post formation treatments were well known to improve softness. "Post formation treatment" refers to the fact that—instead of or in addition to increasing softness during the making or formation of the tissue—the tissue is treated mechanically in a separate process step after forming and drying of the tissue, often just prior to further processing such as combining the tissue with other materials to form an absorbent core or article. Examples for such treatments are U.S. Pat. No. 5,117,540 (Walton) or U.S. Pat. No. 4,440,597 (Wells).

Other attempts to impact on the pore size of distribution materials is described in U.S. Pat. No. 5,244,482 (Hassenboehler), aiming at reducing maximum pore size by stretching a fibrous structure comprising meltable fibers in one direction and "freezing" the deformation by heat curing.

Also, special material composites were developed, aiming at a allowing to tailor the pore size and pore size distribution. Examples for such improvements are described in greater detail in U.S. Pat. No. 5,549,589 (Homey et al.) or in PCT application WO 97/38654 (Seger et al.). Both aim essentially at providing a resilient structure by using specially stiffened cellulosic fibers such as crosslinked cellulose softwood fibers, and by filling the large pores with small and thin cellulosic fibers such as eucalyptus fibers. Both applications further add means for providing sufficient integrity and strength to the structure, the first one (U.S. Pat. No. 5,549,589) by adding thermoplastic fibers and partially melt these, the second (WO 97/38654) by adding a chemical binder.

A further approach as disclosed in EP Application EP-A-0,810,078 (d'Acchioli et al.) uses a special post-formation mechanical treatment of webs, thereby imparting improved fluid handling properties such as described by higher liquid flux rates at certain wicking heights.

With the wish to improve the functionality of the absorbent articles, more specific requirements for distribution materials developed, such that porous materials were investigated in more depth. In order to improve the longitudinal fluid distribution, high surface area synthetic fibers were applied in absorbent structures, such as described in US Statuary Invention Registration H1511. Another class of materials are foamed structures, such as cellulosic foams such as commercially available by Spontex SA, France.

Other polymeric foams for being used in absorbent articles were disclosed in U.S. Pat. No. 5,268,224 (DesMarais), namely High Internal Phase polymerized materials, which can be used for storing liquids, and have at the same time the ability to avoid localized saturation, by spreading the stored fluid throughout the material.

However, all these investigations so far aimed at improving the wicking properties of the distribution materials such as flux, wicking height and wicking times, but failed to recognize the importance of the dewatering mechanism of the distribution materials by the liquid storage materials, especially when such materials are not fully saturated, such as can be relevant in absorbent articles between multiple loadings.

OBJECTS OF THE INVENTION

Henceforth, it is an object of the present invention to provide improved absorbent articles having an improved dewatering functionality of distribution members, especially under low saturation conditions.

It is another object of the present invention, to provide improved absorbent articles comprising materials which allow liquid to be transported throughout an absorbent article even being saturated to a low or moderate degree of saturation.

It is a further object of the present invention to provide such articles further comprising liquid storage materials having a good capillary sorption absorption performance.

SUMMARY

The present invention is an absorbent article containing a fluid distribution member, which has a relatively high permeability even at subsaturation conditions, and which has a lower Capillary Sorption Absorption Height at 50% of its capacity at 0 cm, which is higher than the Capillary Soprtion Desorption Height at 50% of its capacity at 0 cm of a fluid storage member in liquid communication with this distribution member in this article.

Thus, the distribution member has a permeability at 50% of its saturation, which is at least more than about 14%, preferably more than 18%, even more preferably more than 25% or even more than 35% of the permeability at 100% saturation.

Thus, the first fluid storage member has as CSAH 50 of more than about 15 cm, preferably of more than about 23 cm, even more preferably of more than about 27 cm, or even more than about 30 cm, and most preferably more than about 47 cm.

In a further preferred executions, the absorbent article comprises a fluid distribution member which has a permeability at 30% of its saturation k(30) which is more than about 3% of k(100), preferably more than about 5%, more preferably even more than about 10% of k(100).

In further preferred embodiments, the fluid distribution member has a CSDH 50 value of less than about 150 cm, more preferably less than about 100 cm, even more preferably less than about 75 cm, and most preferably less than about 50 cm.

In a specific preferred execution, the fluid distribution member comprises an open celled foam, which can expand upon wetting, and which further can re-collapse upon loosing liquid. In a particularly preferred execution, the distribution member comprises a hydrophilic, flexible polymeric foam structure of interconnected open-cells, even more preferably of the HIPE type.

In a further execution, the absorbent article has at least two liquid storage regions, whereby both liquid storage regions are in liquid communication with the fluid distribution member, wherein preferably at least one of said liquid storage regions comprises material exhibiting a Capillary Sorption Absorption Height at 50% of its maximum capacity (CSAH 50) of at least about 40 cm.

In a further aspect of the invention, the absorbent article having such distribution member can be described by a crotch region and one or more waist regions, whereby said crotch region has a lower ultimate fluid storage capability than said one or more waist regions together, which can be described by having less than 0.9 times the average ultimate fluid storage basis capacity of the absorbent core, more preferably even less than 0.5 times the average ultimate fluid storage basis capacity of the absorbent core, even more preferably less than 0.3 times the average ultimate fluid storage basis capacity of the absorbent core.

In a further aspect, the absorbent article has a crotch region having a sectional ultimate fluid storage capacity of less than 49% of the total core ultimate fluid storage capacity, preferably less than 41% of the total core ultimate fluid storage capacity, even more preferably less than 23% the total core ultimate fluid storage capacity.

In an even further aspect of the present invention, the absorbent article has an ultimate liquid storage material providing at least 80% of the total ultimate storage capacity of the absorbent core, preferably more than 90% of the total ultimate storage capacity of the absorbent core.

In an even further aspect of the present invention, the absorbent article has very little liquid absorbent capacity in the crotch region, preferably at least 50% of the of the crotch region are contain essentially no ultimate storage capacity.

Further, the absorbent article can have less than 50% of said ultimate storage capacity positioned forwardly from the crotch zone in the front half of the article, and more than 50% of said ultimate storage capacity positioned in the rear half of the article. Even more preferably, the absorbent article can have less than 33% of said ultimate storage capacity positioned forwardly from the crotch zone in the front half of the article, and more than 67% of said ultimate storage capacity are positioned in the rear half of the article.

BRIEF DESCRIPTION OF DRAWINGS

FIGS. 1 to 4 show different executions of the permeability test set up. FIGS. 1 and 2 relate to a simplified test. FIGS. 3 and 4 relate to a general test. FIGS. 1 and 3 relate to the measurement of the transplanar permeability, and FIGS. 2 and 4 to the in-plane permeability.

FIG. 6—Shows a diaper as example for an absorbent article

DETAILED DESCRIPTION

Figure 1:
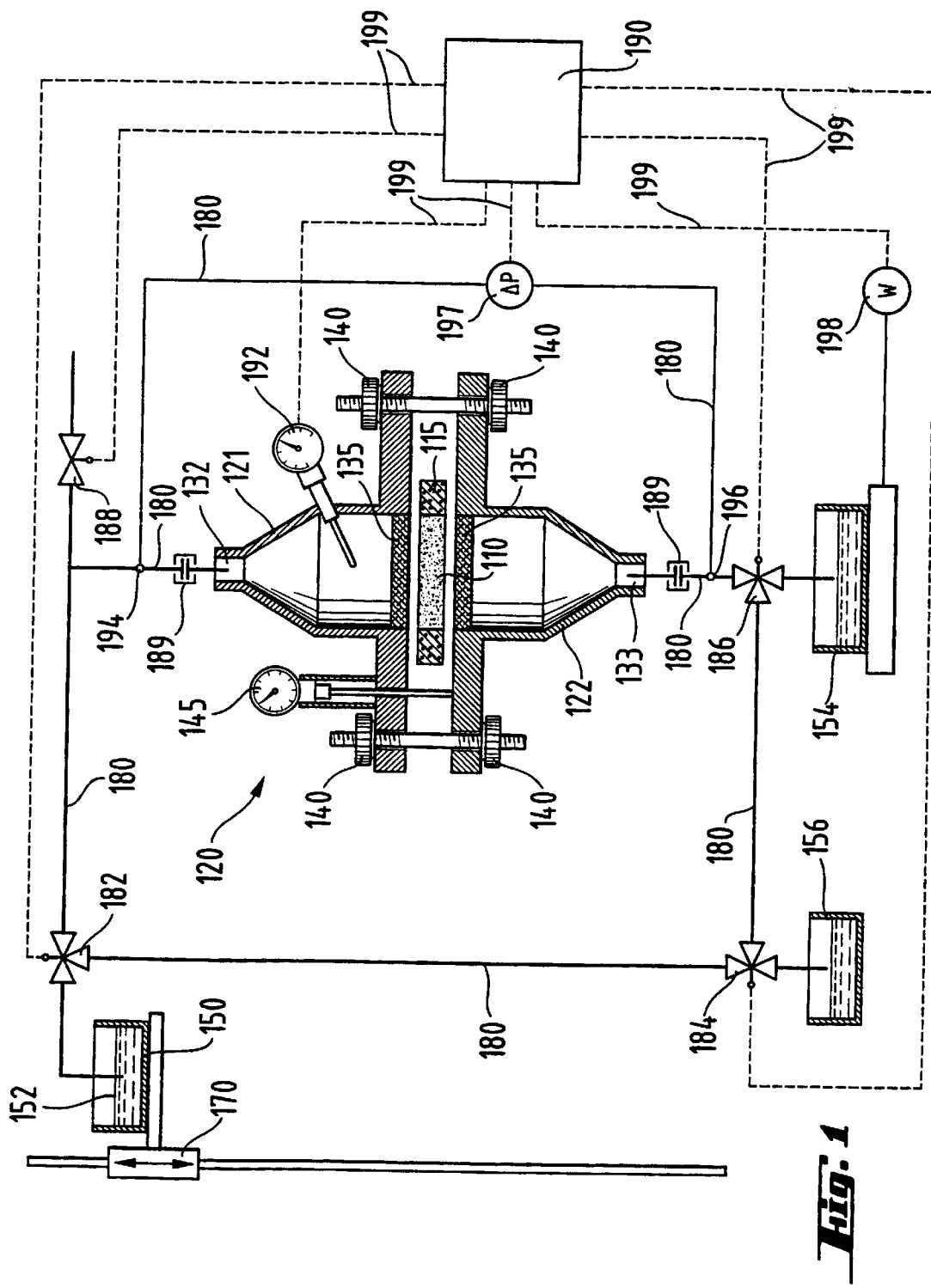

As used herein, the term "fluid handling member" refers to the components of the absorbent article that typically provide at least the fluid handling functionality. An absorbent article can comprise one or more of the various fluid handling members, such as one or more fluid acquisition member, one or more fluid distribution members and/or one or more fluid storage members. Each of these members can comprise on or more sub-elements, which can be homogeneous or not, i.e. each member can be made from one material or from several materials. For example, such members can be layers, optionally consisting of sub-layers, and or optionally having different composition, or density, or thickness.

Each of these members can have a specialized functionality, such primarily providing acquisition functionality or primarily providing fluid storage functionality. Alternatively, members can have multiple functionality, such as the very first "cellulose only" diapers wherein the cellulose fluff performed acquisition, distribution and ultimate storage functionality at the same time.

The "storage absorbent member" refers to the absorbent member(s) of the absorbent core that function primarily to ultimately store absorbed fluids.

A "fluid distribution member" in the meaning of the present invention is a member, which satisfies the requirements as laid out for the fluid distribution functionality, regardless whether the member also has some other fluid handling functionality.

A "fluid acquisition member" refers to parts or the absorbent core, which are primarily designed to receive the liquid as it reaches the absorbent article.

As used herein, the term "absorbent core" refers to the members of the absorbent article that are primarily responsible for fluid handling of the article, thus including the "fluid handling member(s)". As such, the absorbent core typically does not include the topsheet or backsheet of the absorbent article, though in certain instances the topsheet could be considered, for example, to provide specific fluid acquisition performance.

An absorbent core can be divided into "regions" of the core, wherein such "regions" can perform the functionality of one or more of the members as outlined above. Thus, an acquisition region can comprise an acquisition member (and also comprise other members), it can consist of an acquisition member (and nothing else), which can consist of an acquisition material. Or, an acquisition/distribution region can comprise both an acquisition member and an distribution member.

As used herein, the term "absorbent articles" refers to devices which absorb and contain body exudates, and, more specifically, refers to devices which are placed against or in proximity to the body of the wearer to absorb and contain the various exudates discharged from the body. As used herein, the term "body fluids" includes but is not limited to urine, menses, vaginal discharges, sweat and feces.

The term "disposable" is used herein to describe absorbent articles which are not intended to be laundered or otherwise restored or reused as an absorbent article (i.e., they are intended to be discarded after use and, preferably, to be recycled, composted or otherwise disposed of in an environmentally compatible manner).

As used herein, the term "Z-dimension" refers to the dimension orthogonal to the length and width of the member, core or article. The Z-dimension usually corresponds to the thickness of the member, core or article. As used herein, the term "X-Y dimension" refers to the plane orthogonal to the thickness of the member, core or article. The X-Y dimension usually corresponds to the length and width, respectively, of the member, core or article.

As used herein, the terms "region(s)" or "zone(s)" refer to portions or sections of the absorbent member. Thereby, the region(s) or zone(s) can be two-dimensional (front/back) or can be three-dimensional (like an acquisition region having—even if it were in the form of a layer—a three-dimensional extension).

As use herein, the term "layer" refers to an absorbent member whose primary dimension is X-Y, i.e., along its length and width. It should be understood that the term layer is not necessarily limited to single layers or sheets of material. Thus the layer can comprise laminates or combinations of several sheets or webs of the requisite type of materials. Accordingly, the term "layer" includes the terms "layers" and "layered".

For purposes of this invention, the term "upper" should be understood to refers to absorbent members, such as layers, that are nearest to the wearer of the absorbent article, and typically face the topsheet of an absorbent article; conversely, the term "lower" refers to absorbent members that are furthermost away from the wearer of the absorbent article and typically face the backsheet.

All percentages, ratios and proportions used herein are calculated by weight unless otherwise specified.

Absorbent Articles—General Description

An absorbent article generally comprises:
  an absorbent core or core structure (which comprises the improved fluid distribution members according to the present invention, and which may consist of substructures);
  a fluid pervious topsheet;
  a fluid impervious backsheet;
  optionally further features like closure elements or elastification.

FIG. 6 is a plan view of an exemplary embodiment of an absorbent article of the invention which is a diaper.

The diaper 20 is shown in FIG. 6 in its flat-out, uncontracted state (i.e. with elastic induced contraction pulled out except in the side panels wherein the elastic is left in its relaxed condition) with portions of the structure being cut-away to more clearly show the construction of the diaper 20 and with the portion of the diaper 20 which faces away from the wearer, the outer surface 52, facing the viewer. As shown in FIG. 6, the diaper 20 comprises a containment assembly 22 preferably comprising a liquid pervious topsheet 24, a liquid impervious backsheet 26 joined with the topsheet 24, and an absorbent core 28 positioned between the topsheet 24 and the backsheet 26; elasticized side panels 30; elasticized leg cuffs 32; an elastic waist feature 34; and a closure system comprising a dual tension fastening system generally multiply designated as 36. The dual tension fastening system 36 preferably comprises a primary fastening system 38 and a waist closure system 40. The primary fastening system 38 preferably comprises a pair of securement members 42 and a landing member 44. The waist closure system 40 is shown in FIG. 6 to preferably comprise a pair of first attachment components 46 and a second attachment component 48. The diaper 20 also preferably comprises a positioning patch 50 located subjacent each first attachment component 46.

The diaper 20 is shown in FIG. 6 to have an outer surface 52 (facing the viewer in FIG. 6), an inner surface 54 opposed to the outer surface 52, a first waist region 56, a second waist region 58 opposed to the first waist region 56, and a periphery 60 which is defined by the outer edges of the diaper 20 in which the longitudinal edges are designated 62 and the end edges are designated 64. The inner surface 54 of the diaper 20 comprises that portion of the diaper 20 which is positioned adjacent to the wearer's body during use (i.e. the inner surface 54 generally is formed by at least a portion of the topsheet 24 and other components joined to the topsheet 24). The outer surface 52 comprises that portion of the diaper 20 which is positioned away from the wearer's body (i.e. the outer surface 52 generally is formed by at least a portion of the backsheet 26 and other components joined to the backsheet 26). The first waist region 56 and the second waist region 58 extend, respectively, from the end edges 64 of the periphery 60 to the lateral centreline 66 of the diaper 20. The waist regions each comprise a central region 68 and a pair of side panels which typically comprise the outer lateral portions of the waist regions. The side panels positioned in the first waist region 56 are designated 70 while the side panels in the second waist region 58 are designated 72. While it is not necessary that the pairs of side panels or each side panel be identical, they are preferably mirror images one of the other. The side panels 72 positioned in the second waist region 58 can be elastically extensible in the lateral direction (i.e. elasticized side panels 30). (The lateral direction (x direction or width) is defined as the direction parallel to the lateral centreline 66 of the diaper 20; the longitudinal direction (y direction or length) being defined as the direction parallel to the longitudinal centreline 67; and the axial direction (Z direction or thickness) being defined as the direction extending through the thickness of the diaper 20).

FIG. 6 shows a specific of the diaper 20 in which the topsheet 24 and the backsheet 26 have length and width dimensions generally larger than those of the absorbent core 28. The topsheet 24 and the backsheet 26 extend beyond the edges of the absorbent core 28 to thereby form the periphery 60 of the diaper 20. The periphery 60 defines the outer perimeter or, in other words, the edges of the diaper 20. The periphery 60 comprises the longitudinal edges 62 and the end edges 64.

While each elasticized leg cuff 32 may be configured so as to be similar to any of the leg bands, side flaps, barrier cuffs, or elastic cuffs described above, it is preferred that each elasticized leg cuff 32 comprise at least an inner barrier cuff 84 comprising a barrier flap 85 and a spacing elastic member 86 such as described in the above-referenced U.S. Pat. No. 4,909,803. In a preferred embodiment, the elasticized leg cuff 32 additionally comprises an elastic gasketing cuff 104 with one or more elastic strands 105, positioned outboard of the barrier cuff 84 such as described in the above-references U.S. Pat. No. 4,695,278.

The diaper 20 may further comprise an elastic waist feature 34 that provides improved fit and containment. The elastic waist feature 34 at least extends longitudinally outwardly from at least one of the waist edges 83 of the absorbent core 28 in at least the central region 68 and generally forms at least a portion of the end edge 64 of the diaper 20. Thus, the elastic waist feature 34 comprises that portion of the diaper at least extending from the waist edge 83 of the absorbent core 28 to the end edge 64 of the diaper 20 and is intended to be placed adjacent the wearer's waist. Disposable diapers are generally constructed so as to have two elastic waist features, one positioned in the first waist region and one positioned in the second waist region.

The elasticized waist band 35 of the elastic waist feature 34 may comprise a portion of the topsheet 24, a portion of the backsheet 26 that has preferably been mechanically stretched and a bi-laminate material comprising an elastomeric member 76 positioned between the topsheet 24 and backsheet 26 and resilient member 77 positioned between backsheet 26 and elastomeric member 76.

This as well as other components of the diaper are given in more detail in WO 93/16669 which is incorporated herein by reference.

Absorbent Core

The absorbent core should be generally compressible, conformable, non-irritating to the wearer's skin, and capable of absorbing and retaining liquids such as urine and other certain body exudates. As shown in FIG. 6, the absorbent core has a garment surface ("lower" or "bottom" part), a body surface, side edges, and waist edges. The absorbent core may—in addition to the fluid distribution member according to the present invention—comprise a wide variety of liquid-absorbent or liquid handling materials commonly used in disposable diapers and other absorbent articles such as—but not limited to—comminuted wood pulp which is generally referred to as airfelt; meltblown polymers including coform; chemically stiffened, modified or cross-linked cellulosic fibers; tissue including tissue wraps and tissue laminates.

General examples for absorbent structures are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; EP-A-0 640 330 of Bewick-Sonntag et al.; U.S. Pat. No. 5,180,622 (Berg et al.); U.S. Pat. No. 5,102,597 (Roe et al.); U.S. Pat. No. 5,387,207 (LaVon). Such and similar structures might be adopted to be compatible with the requirements outlined below for being used as the absorbent core 28.

The absorbent core can be a unitary core structure, or it can be a combination of several absorbent structures, which in turn can consist of one or more sub-structures. Each of the structures or sub-structures can have an essentially two-dimensional extension (i.e. be a layer) or a three-dimensional shape.

Regions of Absorbent Articles

Generally, absorbent hygienic articles are intended for being worn around the lower end of the body torso. It is an essential design feature of these articles to cover the regions of the body where the discharges occur ("discharge regions"), which extend around the respective body openings. The respective zones of the absorbent article covering the discharge regions are correspondingly referred to as "loading zones". Thus during use, the articles are generally arranged on the wearer such that they extend (for a standing position of the wearer) from the crotch between the legs upwards, both in the front and the back of the wearer.

Generally, such articles have a length dimension exceeding their width dimension, whereby the article is worn such that the axis of the length dimension is aligned with the height direction of the wearer when standing, whilst the width direction of the article is aligned with a line extending from left to right of the wearer.

Because of the anatomy of the human wearer, the space between the legs of the wearer generally confines the space available for the article in this region. For good fit, an absorbent article should be designed such that it fits well in the crotch region. If the width of the article is excessively wide relative to the crotch width of the wearer, the article may be deformed, which might results in deteriorated performance, and reduced wearers comfort.

The point, where the article has its smallest width to fit best between the legs of the wearer then coincides with the point on the wearer, where the distance between the legs is the narrowest, and is—for the scope of the present invention—referred to as the "crotch point".

If the crotch point of an article is not obvious from its shape, it can be determined by placing the article on a wearer of the intended user group (e.g. a toddler) preferably in a standing position, and then placing an extensible filament around the legs in a figure eight configuration. The point in the article corresponding to the point of intersection of the filament is deemed to be the crotch point of the article and consequently also of the absorbent core being affixed within this article.

Whilst this crotch point of the article is often in the middle of the article (in longitudinal direction) this is not necessarily the case. It can very well be, that the part of the article which is intended to be worn in the front is smaller than the back (or rear) part—either in its length dimension, or width, or both, or surface area. Also, the crotch point does not need to be positioned in the middle of the absorbent core, in particular when the absorbent core is not placed longitudinally centred within the article.

The crotch region is the area surrounding the crotch point, so as to cover the respective body openings, respectively discharge regions. Unless otherwise mentioned, this region extends over a length of 50% of the total core length (which, in turn is defined as the distance between the front and rear waist edges of the core, which might be approximated by straight lines perpendicular to the longitudinal center line). If the crotch point is positioned in the middle of the article, then the crotch region starts (when counting from the front core edge) at 25% of total length and extends up to 75% of the total core length. Or, the front and the rear quarter of the length of the absorbent core do not belong to the crotch region, the rest does.

The crotch region length being 50% of the total absorbent core length has been derived for baby diapers, where it has been confirmed that this is a suitable means to describe the fluid handling phenomena. If the present invention is applied in articles having drastically different dimensions, it might become necessary to reduce these 50% (as in the case for Severe Incontinence articles) or to increase this ratio (as in the case for Ultra Light or Light Incontinence articles). In more general terms, this crotch region of the article should not extend much beyond the discharge region of the wearer.

If the crotch point is positioned offset from the mid-point of the article, the crotch region still covers 50% of the total article length (in longitudinal direction), however, not evenly distributed between front and back, but proportionally adjusted to this off-set.

As an example for an article having a total core length of 500 mm, and having a crotch point which is positioned centered, the crotch region will extend from 125 mm away from the front edge up to 375 mm away from front edge. Or, if the crotch point lies 50 mm offset towards the front core edge, (i.e. being 200 mm away from front core edge), the crotch region extends from 100 mm to 350 mm.

In general terms, for an article having a total core length of $L_c$, a crotch point being at a distance $L_{cp}$ away from the front core edge, and a crotch zone length of $L_{cz}$, the front edge of said crotch zone will be positioned at a distance $$L_{fecz} = L_{cp} * (1 - L_{cz}/L_c).$$

For example the absorbent article can be a baby diaper, for being worn by toddlers (i.e. of about 12 to 18 kg baby weight) whereby the size of the article in the trade is generally referred to as MAXI size. Then the article has to be able to receive and retain both fecal materials and urine, whereas for the context of the present invention the crotch region has to be capable to primarily receive urine loadings.

The total area and size of the crotch region is—of course—also depending on the respective width of the absorbent core, i.e. if the core is narrower in the crotch region than outside the crotch region, the crotch region has a smaller area (surface) than the remaining area of the absorbent core.

Whilst it can be contemplated, that the boundaries between crotch region and the rest of the article can also be curvilinear, they are approximated within the present description to be straight lines, perpendicular to the longitudinal axis of the article.

The "crotch region" is further confined by the width of the core in this respective region, and the "crotch region area" by the surface as being defined by the crotch region length and the respective width.

As a complementary element to the crotch region, the absorbent core also comprises at least one but mostly two waist region(s), extending towards the front and/or the rear of the absorbent core outside the crotch region.

Design Capacity and Ultimate Storage Capacity

In order to be able to compare absorbent articles for varying end use conditions, or differently sized articles, the "design capacity" has been found to be a suitable measure.

For example, babies are representing a typical usage group, but even within this group the amount of urine loading, frequency of loading, composition of the urine will vary widely from smaller babies (new-born babies) to toddlers on one side, but also for example among various individual babies.

Another user group may be larger children, still suffering from a certain form of incontinence.

Also, incontinent adults can use such articles, again with a wide range of loading conditions, generally referred to as light incontinence ranging up to severe incontinence.

Whilst the man skilled in the art will readily be able to transfer the teaching to other sizes for further discussion, focus will be put on the toddler sized babies. For such user, urine loadings of up to 75 ml per voiding, with on an average of four voidings per wearing period resulting in a total loading of 300 ml, and voiding rates of 15 ml/sec have been found to be sufficiently representative.

Henceforth, such articles being able to cope with such requirements should have the capability of picking up such amounts of urine, which will be referred to for the further discussion as "design capacity".

These amounts of fluids have to be absorbed by materials which can ultimately store the bodily fluids, or at least the aqueous parts of these, such that—if any—only little fluid is left on the surface of the article towards the wearers skin. The term "ultimate" refers in one respect to the situation as in the absorbent article at long wearing times, in the other respect to absorbent materials which reach their "ultimate" capacity when being equilibrated with their environment. This can be in such an absorbent article under real in-use conditions after long wearing times, or this also can be in a test procedure for pure materials or material composites. As many of the processes under consideration have asymptotic kinetic behavior, one skilled in the art will readily consider "ultimate" capacities to be reached when the actual capacity has reached a value sufficiently close to the asymptotic endpoint, e.g. relative to the equipment measurement accuracy.

As an absorbent article can comprise materials which are primarily designed to ultimately store fluids, and other materials which are primarily designed to fulfill other functions such as acquisition and/or distribution of the fluid, but may still have a certain ultimate storage capability, suitable core materials according to the present invention are described without attempting to artificially separate such functions. Nonetheless, the ultimate storage capacity can be determined for the total absorbent core, for regions thereof, for absorbent structures, or even sub-structures, but also for materials as being used in any of the previous.

As discussed in the above for varying the dimensions of the article, one skilled in the art will be able to readily adopt the appropriate design capacities for other intended user groups.

Materials for Being Used in Absorbent Cores

The absorbent core for the present invention can comprise fibrous materials to form fibrous web or fibrous matrices.

Fibers useful in the present invention include those that are naturally occurring fibers (modified or unmodified), as well as synthetically made fibers. Examples of suitable unmodified/modified naturally occurring fibers include cotton, Esparto grass, bagasse, kemp, flax, silk, wool, wood pulp, chemically modified wood pulp, jute, rayon, ethyl cellulose, and cellulose acetate. Suitable synthetic fibers can be made from polyvinyl chloride, polyvinyl fluoride, polytetrafluoroethylene, polyvinylidene chloride, polyacrylics such as ORLON®, polyvinyl acetate, polyethylvinyl acetate, non-soluble or soluble polyvinyl alcohol, polyolefins such as polyethylene (e.g., PULPEX®) and polypropylene, polyamides such as nylon, polyesters such as DACRON® or KODEL®, polyurethanes, polystyrenes, and the like. The fibers used can comprise solely naturally occurring fibers, solely synthetic fibers, or any compatible combination of naturally occurring and synthetic fibers. The fibers used in the present invention can be hydrophilic, or can be a combination of both hydrophilic and hydrophobic fibers.

For many absorbent cores or core structures according to the present invention, the use of hydrophilic fibers is preferred. Suitable hydrophilic fibers for use in the present invention include cellulosic fibers, modified cellulosic fibers, rayon, polyester fibers such as polyethylene terephthalate (e.g., DACRON®), hydrophilic nylon (HYDROFIL®), and the like. Suitable hydrophilic fibers can also be obtained by hydrophilizing hydrophobic fibers, such as surfactant-treated or silica-treated thermoplastic fibers derived from, for example, polyolefins such as polyethylene or polypropylene, polyacrylics, polyamides, polystyrenes, polyurethanes and the like.

Suitable wood pulp fibers can be obtained from many well-known chemical processes such as—but not limited to—the Kraft and sulfite processes. A further suitable type of fibers is chemically stiffened cellulose. As used herein, the term "chemically stiffened cellulosic fibers" means cellulosic fibers that have been stiffened by chemical means to increase the stiffness of the fibers under both dry and aqueous conditions. Such means can include the addition of a chemical stiffening agent that, for example, coats and/or impregnates the fibers. Such means can also include the stiffening of the fibers by altering the chemical structure, e.g., by crosslinking polymer chains.

Polymeric stiffening agents that can coat or impregnate the cellulosic fibers include: cationic modified starches having nitrogen-containing groups (e.g., amino groups) such as those available from National Starch and Chemical Corp., Bridgewater, N.J., USA; latexes; wet strength resins such as polyamide-epichlorohydrin resin (e.g., Kymene® 557H, Hercules, Inc. Wilmington, Del., USA), polyacrylamide resins described, for example, in U.S. Pat. No. 3,556,932 (Coscia et al), issued Jan. 19, 1971; commercially available polyacrylamides marketed by American Cyanamid Co., Stamford, Conn., USA, under the tradename Parez® 631 NC; urea formaldehyde and melamine formaldehyde resins, and polyethylenimine resins.

These fibers can also be stiffened by chemical reaction. For example, crosslinking agents can be applied to the fibers that, subsequent to application, are caused to chemically form intrafiber crosslink bonds. These crosslink bonds can increase the stiffness of the fibers. While the utilisation of intrafiber crosslink bonds to chemically stiffen the fiber is preferred, it is not meant to exclude other types of reactions for chemical stiffening of the fibers.

Fibers stiffened by crosslink bonds in individualised form (i.e., the individualised stiffened fibers, as well as process for their preparation) are disclosed, for example, in U.S. Pat. No. 3,224,926 (Bernardin), issued Dec. 21, 1965; U.S. Pat. No. 3,440,135 (Chung), issued Apr. 22, 1969; U.S. Pat. No. 3,932,209 (Chatterjee), issued Jan. 13, 1976; and U.S. Pat. No. 4,035,147 (Sangenis et al), issued Dec. 19, 1989; U.S. Pat. No. 4,898,642d (Moore et al), issued Feb. 6, 1990; and U.S. Pat. No. 5,137,537 (Herron et al), issued Aug. 11, 1992.

In currently preferred stiffened fibers, chemical processing includes intrafiber crosslinking with crosslinking agents while such fibers are in a relatively dehydrated, defibrated (i.e., individualised), twisted, curled condition. Suitable chemical stiffening agents are typically monomeric crosslinking agents including, especially $C_2$–$C_9$ polycarboxylic acids such as citric acid. Preferably, such stiffened fibers are twisted and curledas descibed in more details in U.S. Pat. No. 4,898,642.

These chemically stiffened cellulosic fibers have certain properties that make them particularly useful in certain absorbent structures according to the present invention, relative to unstiffened cellulosic fibers. In addition to being hydrophilic, these stiffened fibers have unique combinations of stiffness and resiliency.

In addition to or alternatively synthetic or thermoplastic fibers can comprised in the absorbent structures, such as being made from any thermoplastic polymer that can be melted at temperatures that will not extensively damage the fibers. Preferably, the melting point of this thermoplastic material will be less than about 190° C., and preferably between about 75° C. and about 175° C. In any event, the melting point of this thermoplastic material should be no lower than the temperature at which the thermally bonded absorbent structures, when used in absorbent articles, are likely to be stored. The melting point of the thermoplastic material is typically no lower than about 50° C.

The thermoplastic materials, and in particular the thermoplastic fibers, can be made from a variety of thermoplastic polymers, including polyolefins such as polyethylene (e.g., PULPEX®) and polypropylene, polyesters, copolyesters, polyvinyl acetate, polyamides, copolyamides, polystyrenes, polyurethanes and copolymers of any of the foregoing such as vinyl chloride/vinyl acetate, and the like. Suitable thermoplastic materials include hydrophobic fibers that have been made hydrophilic, such as surfactant-treated or silica-treated thermoplastic fibers derived from, for example, polyolefins such as polyethylene or polypropylene, polyacrylics, polyamides, polystyrenes, polyurethanes and the like. The surface of the hydrophobic thermoplastic fiber can be rendered hydrophilic by treatment with a surfactant, such as a nonionic or anionic surfactant, e.g., by spraying the fiber with a surfactant, by dipping the fiber into a surfactant or by including the surfactant as part of the polymer melt in producing the thermoplastic fiber. Upon melting and resolidification, the surfactant will tend to remain at the surfaces of the thermoplastic fiber. Suitable surfactants include nonionic surfactants such as Brij® 76 manufactured by ICI Americas, Inc. of Wilmington, Del., and various surfactants sold under Pegosperse® trademark by Glyco Chemical, Inc. of Greenwich, Conn. Besides nonionic surfactants, anionic surfactants can also be used. These surfactants can be applied to the thermoplastic fibers at levels of, for example, from about 0.2 to about 1 gram per square of centimetre of thermoplastic fiber.

Suitable thermoplastic fibers can be made from a single polymer (monocomponent fibers), or can be made from more than one polymer (e.g., bicomponent fibers). For example, "bicomponent fibers" can refer to thermoplastic fibers that comprise a core fiber made from one polymer that is encased within a thermoplastic sheath made from a different polymer. The polymer comprising the sheath often melts at a different, typically lower, temperature than the polymer comprising the core. As a result, these bicomponent fibers provide thermal bonding due to melting of the sheath polymer, while retaining the desirable strength characteristics of the core polymer.

Suitable bicomponent fibers for use in the present invention can include sheath/core fibers having the following polymer combinations: polyethylene/polypropylene, polyethylvinyl acetate/polypropylene, polyethylene/polyester, polypropylene/polyester, copolyester/polyester, and the like. Particularly suitable bicomponent thermoplastic fibers for use herein are those having a polypropylene or polyester core, and a lower melting copolyester, polyethylvinyl acetate or polyethylene sheath (e.g., DANAKLON®, CELBOND®) or CHISSO® bicomponent fibers). These bicomponent fibers can be concentric or eccentric. As used herein, the terms "concentric" and "eccentric" refer to whether the sheath has a thickness that is even, or uneven, through the cross-sectional area of the bicomponent fiber. Eccentric bicomponent fibers can be desirable in providing more compressive strength at lower fiber thicknesses. Suitable bicomponent fibers for use herein can be either uncrimped (i.e. bent). Bicomponent fibers can be crimped by typical textile means such as, for example, a stuffer boy method or the gear crimp method to achieve a predominantly two-dimensional or "flat" crimp.

In the case of thermoplastic fibers, their length can vary depending upon the particular melt point and other properties desired for these fibers. Typically, these thermoplastic fibers have a length from about 0.3 to about 7.5 cm long, preferably from about 0.4 to about 3.0 cm long. The properties, including melt point, of these thermoplastic fibers can also be adjusted by varying the diameter (caliper) of the fibers. The diameter of these thermoplastic fibers is typically defined in terms of either denier (grams per 9000 meters) or decitex (grams per 10,000 meters dtex). Depending on the specific arrangement within the structure, suitable thermoplastic fibers can have a decitex in the range from well below 1 decitex, such as 0.4 decitex to about 20 dtex.

Said fibrous materials may be used in an individualised form when the absorbent article is being produced, and an airlaid fibrous structure is formed on the line. Said fibers may also be used as a preformed fibrous web or tissue. These structures are then delivered to the production of the article essentially in endless or very long form (e.g. on a roll, spool) and will then be cut to the appropriate size. This can be done on each of such materials individually before these are combined with other materials to form the absorbent core, of when the core itself is cut and said materials are co-extensive with the core.

There is a wide variety of making such web, and such processes are very well known in the art.

With regard to fibers used for producing such webs, there is nearly no limitation in principle—though certain specific web forming and bonding processes might not be fully compatible with certain materials or fiber types.

When looking at individualised fibers as a starting material for making a web, these can be laid down in a fluid medium—if this is gaseous (air) such structures are generally referred to as "dry-laid", if it is liquid such structures are generally referred to as "wet-laid". "Wet-laying" is broadly used to produce paper tissues with a wide range of properties. This term is most commonly used with cellulosic materials, however, also synthetic fibers can be included.

"Dry-laying" is broadly used for non-woven webs, and often the carding process can be used to form such webs. Also the commonly known "air-laid tissues" fall under this category.

A molten polymer can be extruded into fibers which then can be formed directly into a web (i.e. omitting the process step of making individual fibers which then are formed into a web in a separate process step). The resulting structures are commonly referred to as non-wovens of the meltblown type or—if fibers are significantly more drawn—spunbonded webs.

Further, webs can also be formed by combining one or more of the other formation technologies.

In order to give certain strength and integrity properties to the web structures, these are generally bonded. The most broadly used technologies are (a) chemical bonding or (b) thermo bonding by melting a part of the web such. For the latter, the fibers can be compressed, resulting in distinct bonding points, which, for example for nonwoven materials, can cover a significant portion of the total area, values of 20% are not uncommon. Or—particularly useful for structures where low densities are desired—"air-through" bonding can be applied, where parts of the polymers e.g. the sheath material of a BiCo-fibers are molten by means of heated air passing through the (often air-laid) web.

After the webs are formed and bonded, these can be further treated to modify specific properties. This can be—as one of many possible examples—additional surfactant to render hydrophobic fibers more hydrophilic, or vice versa. Also, post formation mechanical treatment, such as disclosed in EP application 96108427.4 can be used to impart particularly useful properties to such materials.

In addition or alternatively to fibrous webs, the absorbent cores may comprise other porous materials, such as foams. Preferred foams are open-celled absorbent polymeric foam materials as being derived by polymerising a High Internal Phase Water-in-Oil Emulsion (hereafter referred to a HIPE). Such polymeric foams may be formed to provide the requisite storage properties, as well as the requisite distribution properties.

HIPE-derived foams which provide both the requisite distribution and storage properties for use herein are described in copending U.S. patent application Ser. No. 08/563,866 (DesMarais et al.), filed Nov. 25, 1995 (hereafter referred to as "'866 application"), the disclosure of which is hereby incorporated by reference; copending U.S. patent application Ser. No. 08/542,497, filed Oct. 13, 1995 (Dyer et al.); U.S. Pat. No. 5,387,207 (Dyer et al.), issued Feb. 7, 1995; and U.S. Pat. No. 5,260,345 (DesMarais et al.), issued Nov. 9, 1993; the disclosure of each of which is hereby incorporated by reference.

Polymeric foams useful in the present invention are those which are relatively open-celled. This means the individual cells of the foam are in complete, unobstructed communication with adjoining cells. The cells in such substantially open-celled foam structures have intercellular openings or "windows" that are large enough to permit ready fluid transfer from one cell to the other within the foam structure.

These substantially open-celled foam structures will generally have a reticulated character with the individual cells being defined by a plurality of mutually connected, three dimensionally branched webs. The strands of polymeric material making up these branched webs can be referred to as "struts." As used herein, a foam material is "open-celled" if at least 80% of the cells in the foam structure that are at least 1 micro meter in size are in fluid communication with at least one adjacent cell.

In addition to being open-celled, these polymeric foams are sufficiently hydrophilic to permit the foam to absorb aqueous fluids in the amounts specified hereafter. The internal surfaces of the foam structures are rendered hydrophilic by residual hydrophilizing surfactants left in the foam structure after polymerization, or by selected post-polymerization foam treatment procedures.

The polymeric foams can be prepared in the form of collapsed (i.e. unexpanded), polymeric foams that, upon contact with aqueous fluids, expand and absorb such fluids. See, for example, copending U.S. patent application Ser. No. 08/563,866 and U.S. Pat. No. 5,387,207. These collapsed polymeric foams are usually obtained by expressing the water phase from the polymerized HIPE foam through compressive forces, and/or thermal drying and/or vacuum dewatering. After compression, and/or thermal drying/vacuum dewatering, the polymeric foam is in a collapsed, or unexpanded state. Alternatively, such foams can be non-collapsible foams, such as those described copending U.S. patent application Ser. No. 081542,497 and U.S. Pat. No. 5,260,345.

Superabsorbent Polymers or Hydrogels

Optionally, and often preferably, the absorbent structures according to the present invention can comprise superabsorbent polymers, or hydrogels. The hydrogel-forming absorbent polymers useful in the present invention include a variety of substantially water-insoluble, but water-swellable polymers capable of absorbing large quantities of liquids. Such polymer materials are also commonly referred to as "hydrocolloids", or "superabsorbent" materials. These hydrogel-forming absorbent polymers preferably have a multiplicity of anionic, functional groups, such as sulfonic acid, and more typically carboxy, groups. Examples of polymers suitable for use herein include those which are prepared from polymerisable, unsaturated, acid-containing monomers.

Some non-acid monomers can also be included, usually in minor amounts, in preparing the hydrogel-forming absorbent polymers herein. Such non-acid monomers can include, for example, the water-soluble or water-dispersible esters of the acid-containing monomers, as well as monomers that contain no carboxylic or sulfonic acid groups at all. Examples for such well known materials are described e.g. in U.S. Pat. No. 4,076,663 (Masuda et al), issued Feb. 28, 1978, and in U.S. Pat. No. 4,062,817 (Westerman), issued Dec. 13, 1977.

Hydrogel-forming absorbent polymers suitable for the present invention contain carboxy groups. These polymers include hydrolysed starch-acrylonitrile graft copolymers, partially neutralised starch-acrylonitrile graft copolymers, starch-acrylic acid graft copolymers, partially neutralised starch-acrylic acid graft copolymers, saponified vinyl acetate-acrylic ester copolymers, hydrolysed acrylonitrile or acrylamide copolymers, slightly network crosslinked polymers of any of the foregoing copolymers, partially neutralised polyacrylic acid, and slightly network crosslinked polymers of partially neutralised polyacrylic acid. These polymers can be used either solely or in the form of a mixture of two or more different polymers. Examples of these polymer materials are disclosed in U.S. Pat. Nos. 3,661,875, 4,076,663, 4,093,776, 4,666,983, and 4,734,478.

Most preferred polymer materials for use in making hydrogel-forming particles are slightly network crosslinked polymers of partially neutralised polyacrylic acids and starch derivatives thereof. Most preferably, the hydrogel-forming particles comprise from about 50 to about 95%, preferably about 75%, neutralised, slightly network crosslinked, polyacrylic acid (i.e. poly (sodium acrylate/acrylic acid)).

As described above, the hydrogel-forming absorbent polymers are preferably slightly network crosslinked. Network crosslinking serves to render the polymer substantially water-insoluble and, in part, determines the absorptive capacity and extractable polymer content characteristics of the precursor particles and the resultant macrostructures. Processes for network crosslinking the polymers and typical network crosslinking agents are described in greater detail in the herein before-referenced U.S. Pat. No. 4,076,663, and in DE-A-4020780 (Dahmen).

The superabsorbent materials can be used in particulate form or in fibrous form and may also be combined other elements to form preformed structures.

Whilst the individual elements have been disclosed separately, and absorbent structure or substructure can be made by combining one or more of these elements.

Without intending a limiting effect, the following describes suitable combinations.

i) Particular Superabsorbent polymer (SAP) mixed with cellulosic or other fibers. The basic principle is well established and known, however, upon attempting to reduce thinness of the articles, higher and higher ratios of weight of SAP to fibers have been employed recently. Within this scope, combination of the SAP with binders such as hot-melt adhesives (such as disclosed in EP-A-0,695,541) or with meltable polymeric material (such as PE particles) can be a suitable tool to immobilise the SAP;

ii) SAP forming a substructure by interparticle crosslinks;

iii) Fibrous SAP being mixed with other fibers, or forming a fibrous SAP web;

iv) foam structures comprising differing in pore sizes etc.

Improved Absorbent Articles

After having described absorbent articles and suitable members, materials, structures, components or subcomponents in general terms, the following will describe the requirements for the fluid storage and fluid distribution members according to the present invention, as well as the materials suitable for being used in such members.

Improved Distribution Member

The requirements for the distribution members can be determined by either looking at the member or at the materials contained in said member. Henceforth, the requirements as laid out in the present description have to be satisfied for either the total member or for the respective materials therein.

Henceforth, distribution members or materials useful for such members according to the present invention can be described by the following important parameter:

First, the permeability at full saturation (k100) of the member or material. Conventional distribution materials have this permeability balanced so as to find the optimum between having little resistance to the fluid flow (i.e. high permeability) and sufficient capillary pressure so as to provide wicking properties, such as results from smaller pore sizes (i.e. lower permeability). The permeability at full saturation (k100) should generally be more than 1 Darcy (with 1 Darcy corresponding to $9.869* 10^{-13} m^2$), preferably more than 2 Darcy, or even 8 Darcy, or even more preferably more than 100 Darcy. The full saturation can be determined by the Capsorption test as described hereinafter as the maximum uptake, corresponding to the result Capillary Sorption Absorption Capacity at 0 cm height (CSAC 0).

Second, the dependency of the permeability on the degree of saturation. This property has not been considered in previous material design considerations, and conventional materials have a strongly sub-proportional behavior, i.e. the actual permeability at a degree of saturation of less than 100% is significantly lower than it would be for a linear correlation between actual permeability and saturation.

Thirdly, the Capillary Sorption Pressure, namely the Capillary Sorption Desorption pressure, such as measured in the Capillary Sorption Test as described hereinafter. This parameter describes the ability of the materials or members to release liquids, to satisfy their role as a distribution element in an absorbent article.

Additionally and often preferably, the distribution materials may satisfy the requirement of high fluid flux rates in the vertical wicking flux test as described herein after. Preferably, the materials provide at a wicking height of 15 cm a flux of at least 0.045 $g/cm^2/sec$, preferably more than 0.06 $g/cm^2/sec$, and even more preferably more than 0.10 $g/cm^2/sec$.

With careful selection of materials satisfying the right balance of the these parameter, important benefits can be realized for the absorbent structures and/or respective articles.

First, the liquid distribution materials are readily dewatered after they have been loaded such as with a urine gush. This is relevant so as to allow these materials to be ready for receiving a subsequent loading as it often occurs in real use.

Second, these materials allow a more even liquid distribution of liquids, even at loads which are relatively small compared to the design capacity. This is even more important for designs which aim at maintaining an improved fit on the wearer by avoiding high liquid accumulation in certain regions of the article, but rather aim for an even distribution of the liquid stored.

Thirdly, if the materials also satisfy the high flux requirements, the liquid can be well and quickly distributed even against gravity. This becomes particularly relevant, if the ultimate storage of the fluid is intended to be distant to the loading zone or area. These materials are therefore especially useful in core designs such as described in PCT Application U.S. Ser. No. 97/05046 filed on Mar. 27, 1997.

The permeability of the materials or members are determined by the permeability tests as described hereinafter.

Without wishing to be bound by the theory, it is believed, that the actual permeability k{S} has a dependency from the degree of saturation, which for many relevant systems can be approximated by the following equation (see also "Dynamics of fluids in porous media" by J. Bear, Haifa, publ. Dover Publications, Inc., New York, 1988, esp. pages 461ff, 491ff):

$$k\{S\}=k\{100\}*\{S^{SDP}\}$$

wherein k denotes the permeability in units of Darcy; and SDP represents the dimensionless exponent or Saturation Dependency Parameter describing the sub-proportional behavior. S denotes the degree of saturation, ranging from 0 to 1, wherein the value of 1 corresponds to full saturation (i.e. 100% saturation) under zero external and/or capillary pressure).

Conventional design criteria for distribution materials focused on high values for permeability at saturation (k100), which of course could lead to structures having little or no wicking capability, thus being suitable as acquisition material, wherein essentially the "free flow regime" should be controlled, but not for distribution materials. Such materials would have very poor transport properties under wicking conditions, such as transporting against gravity. Such extreme properties are found in conventional acquisition materials, though distribution material such as described in European Patent Application EP-A-0,809,991 provide a combination of a wicking ability and free flow control—but still under full saturation conditions.

Materials according to the present invention exhibit a permeability k(100) of at least 1 Darcy, preferably at least 2 Darcy. Higher values for the permeability provide an even less reduced resistance to the fluid transport, and are preferred as long as this is achieved without violating the further requirements as laid out herein. In particular, materials having a permeability of more than 8 Darcy or even more than 100 Darcy can be very suitable.

As can be seen from the equation, a higher value for the SDP parameter describes systems with a stronger sub-proportional behavior—if the SDP were equal to one, a linear relation would exist. Conventional distribution materials exhibit a strong sub-proportional behavior, such as can be described by SDP having values of 3 or more. For such a value, the permeability at 50% saturation is only 12.5% of the permeability at 100% saturation, thus also the ability for receiving and distributing further liquid load is dramatically reduced.

Henceforth, materials according to the present invention have a SDP value of less than 3, preferably less than 2.75, even more preferably less than 2.5, and values of less than 2 are even better. Such values correspond to a permeability at 50% saturation of more than 14% of the permeability at 100% saturation, preferably more than about 18%, even more preferably more than about 25% and values of more than 35% are even better. Such values correspond to a permeability at 30% saturation of more than about 3.5% of the permeability at 100% saturation, preferably more than about 5%, even more preferably more than about 10%.

The simplified permeability test as laid out hereinafter can measure the "trans-planar" permeability, i.e. the permeability in the thickness dimension of the sample as determined, and—with a modified sample cell—also the "in-plane" permeability. For a number of materials, such as isotropically foamed foams, the trans-planar and the in-plane permeability will be essentially identical. This Simplified Permeability Test provides a simple test set up to measure permeability for two special conditions: Either the permeability can be measured for a wide range of porous materials (such as non-wovens made of synthetic fibres, or cellulosic structures) at 100% saturation, or for materials, which reach different degrees of saturation with a proportional change in caliper without being filled with air (respectively the outside vapour phase) for which the permeability at varying degrees of saturation can readily be measured at various thicknesses.

For example the described collapsible foams exhibit a thickness or caliper, which is dependent on the degree of fluid load or saturation, i.e. they have a certain thickness at saturation, which is being reduced upon removal of fluid, as the foam pores are of such a size, that they collapse upon removal of liquid from them. Conversely, a certain caliper can be set to define a certain degree of loading. Thus, such materials the Simplified Permeability Test can be readily applied to determine the dependency of the permeability on the saturation.

The General Permeability Test as described hereinafter is useful for determining the dependency of the permeability on the saturation for porous materials in the general sense, such as fibrous webs or structures, or foams which maintain their pore size essentially independent of the degree of wetting.

A further important requirement for the materials or members according to the present invention is their ability to release the fluid to a storage medium. This reflects the fact, that the distribution materials or members should not retain the liquid for too long times, but only for the time that is required to transport he fluid to the appropriate storage material of member.

A suitable parameter to describe this property is the Capillary Sorption Desorption pressure, as determined via the member's ability to receive and to release fluid at varying capillary pressures, herein determined in units of water column height ("capillary height"), which are generally encountered when the member is positioned in an absorbent article. The Capillary Sorption Absorbent Capacity test (also referred to herein as the Capsorption test) measures the amount of test fluid per gram of an absorbent member or material that is taken up or released when the material or member is placed at varying heights on a capillary sorption apparatus. The Capillary Sorption Absorbent Capacity test is described in greater detail in the Test Methods section below, yielding the Capillary Sorption Desorption Height at which the material has released 50% of the amount of fluid at 0 cm sorption height (CSDH 50).

Materials useful in the context of the present invention should have a CSDH 50 of less than 150 cm, preferably less than 100 cm, even more preferably less than 75 cm or even less than 50 cm.

Materials particularly useful for being used for the present invention are hydrophilic, flexible polymeric foam structures of interconnected open-cells.

For such foams, the mechanical strength of the foam can be such that, upon giving up its liquid, the foam collapses under the capillary pressures involved. The collapse process reduces the effective foam capacity by a substantial factor related to the density of the foam, as is described hereinafter. The collapse, if relatively uniform throughout the structure, also reduces the amount of liquid held in place at the point of liquid insult. In this regard, the strength of the foams is less than the capillary pressure exerted by the foams such that the foams will collapse when the aqueous liquids are removed by the storage component of the core. Capillary pressure is controlled herein primarily by adjusting foam cell size (which relates inversely to surface area per unit volume). Strength is controlled by the combination of crosslink density and foam density, which can be expressed as crosslink density per unit volume as defined hereinafter. The type of crosslinker and other comonomers can also be influential.

Polymeric foams useful herein are those which are relatively open-celled. The cells in such substantially open-celled foam structures have intercellular openings or "windows" that are large enough to permit ready liquid transfer from one cell to the other within the foam structure.

These substantially open-celled foam structures will generally have a reticulated character with the individual cells being defined by a plurality of mutually connected, three dimensionally branched webs. The strands of polymeric material making up these branched webs can be referred to as "struts." For purposes of the present invention, a foam material is "open-celled" if at least 80% of the cells in the foam structure that are at least 1 µm in size are in fluid communication with at least one adjacent cell.

In addition to being open-celled, these polymeric foams are sufficiently hydrophilic to permit the foam to absorb aqueous liquids. The internal surfaces of the foam structures are rendered hydrophilic by residual hydrophilizing surfactants and/or salts left in the foam structure after polymerization, or by selected post-polymerization foam treatment procedures, as described hereafter.

The extent to which these polymeric foams are "hydrophilic" can be quantified by the "adhesion tension" value exhibited when in contact with an absorbable test liquid. The adhesion tension exhibited by these foams can be determined experimentally using a procedure where weight uptake of a test liquid, e.g., synthetic urine, is measured for a sample of known dimensions and capillary suction specific surface area. Such a procedure is described in greater detail in the Test Methods section of U.S. Pat. No. 5,387,207 (Dyer et al.) issued Feb. 7, 1995, which is incorporated by reference. Foams which are useful as distribution materials of the present invention are generally those which exhibit an adhesion tension value of from about 15 to about 65 dynes/cm, more preferably from about 20 to about 65 dynes/cm, as determined by capillary suction uptake of synthetic urine having a surface tension of 65±5 dynes/cm.

An important aspect of these foams is their glass transition temperature (Tg). The Tg represents the midpoint of the transition between the glassy and rubbery states of the polymer. Foams that have a higher Tg than the temperature of use can be very strong but can also be very rigid and potentially prone to fracture. Such foams also tend to creep under stress and be poorly resilient when used at temperatures colder than the Tg of the polymer. The desired combination of mechanical properties, specifically strength and resilience, typically necessitates a fairly selective range of monomer types and levels to achieve these desired properties.

For distribution foams useful for the present invention, the Tg should be as low as possible, so long as the foam has acceptable strength. Accordingly, monomers are selected as much as possible that provide corresponding homopolymers having lower Tg's.

The shape of the glass transition region of the polymer can also be important, i.e., whether it is narrow or broad as a function of temperature. This glass transition region shape is particularly relevant where the in-use temperature (usually ambient or body temperature) of the polymer is at or near the Tg. For example, a broader transition region can mean transition is incomplete at in-use temperatures. Typically, if the transition is incomplete at the in-use temperature, the polymer will evidence greater rigidity and will be less resilient. Conversely, if the transition is completed at the in-use temperature, then the polymer will exhibit faster recovery from compression. Accordingly, it is desirable to control the Tg and the breadth of the transition region of the polymer to achieve the desired mechanical properties. Generally, it is preferred that the Tg of the polymer be at least about 10° C. lower than the in-use temperature. (The Tg and the width of the transition region are derived from the loss tangent vs. temperature curve from a dynamic mechanical analysis (DMA) measurement, as described in U.S. Pat. No. 5,563,179 (Stone et al.) issued Oct. 8, 1996.)

Polymeric foams useful for the present invention can be described by a number of parameter.

Foams useful for the present invention are able to wick aqueous liquids to a significant height against the force of gravity, e.g., at least about 15 cm. The column of liquid held within the foam exerts a significant contractile capillary pressure. At a height determined by both the strength of the foam (in compression) and the surface area per unit volume of the foam, the foam will collapse. This heigh is the Capillary Collapse Pressure (CCP) expressed in cm at which 50% of the volume of the foam at zero head pressure is lost. Preferred distribution foams useful for the present invention will have a CCP of at least about 15 cm, more preferably at least about 20 cm, still more preferably at least about 25 cm. Typically, preferred distribution foams will have a capillary collapse pressure of from about 15 cm to about 50 cm, more preferably from about 20 cm to about 45 cm, still more preferably from about 25 to about 40 cm.

A feature that can be useful in defining preferred polymeric foams is the cell structure. Foam cells, and especially cells that are formed by polymerizing a monomer-containing oil phase that surrounds relatively monomer-free water-phase droplets, will frequently be substantially spherical in shape. These spherical cells are connected to each other by openings, which are referred to hereafter as holes between cells. Both the size or "diameter" of such spherical cells and the diameter of the openings (holes) between the cells are commonly used for characterizing foams in general. Since the cells, and holes between the cells, in a given sample of polymeric foam will not necessarily be of approximately the same size; average cell and hole sizes, i.e., average cell and hole diameters, will often be specified.

Cell and hole sizes are parameters that can impact a number of important mechanical and performance features of the, including the liquid wicking properties of these foams, as well as the capillary pressure that is developed within the foam structure. A number of techniques are available for determining the average cell and hole sizes of foams. A useful technique involves a simple measurement based on the scanning electron photomicrograph of a foam sample. The foams useful as absorbents for aqueous liquids in accordance with the present invention will preferably have a number average cell size of from about 20 μm to about 60 μm, and typically from about 30 μm to about 50 μm, and a number average hole size of from about 5 μm to about 15 μm, and typically from about 8 μm to about 12 μm.

"Capillary suction specific surface area" is a measure of the test-liquid-accessible surface area of the polymeric network accessible to the test liquid. Capillary suction specific surface area is determined both by the dimensions of the cellular units in the foam and by the density of the polymer, and is thus a way of quantifying the total amount of solid surface provided by the foam network to the extent that such a surface participates in absorbency.

For purposes of this invention, capillary suction specific surface area is determined by measuring the amount of capillary uptake of a low surface tension liquid (e.g., ethanol) which occurs within a foam sample of a known mass and dimensions. A detailed description of such a procedure for determining foam specific surface area via the capillary suction method is set forth in the Test Methods section of U.S. Pat. No. 5,387,207 supra. Any reasonable alternative method for determining capillary suction specific surface area can also be utilized.

Distribution foams useful for the present invention will preferably have a capillary suction specific surface area of at least about 0.01 $m^2$/ml, more preferably at least about 0.03 $m^2$/ml. Typically, the capillary suction specific surface area is in the range from about 0.01 to about 0.20 $m^2$/ml, preferably from about 0.03 to about 0.10 $m^2$/ml, most preferably from about 0.04 to about 0.08 $m^2$/ml.

"Foam density" (i.e., in grams of foam per cubic centimeter of foam volume in air) is specified herein on a dry basis. The density of the foam, like capillary suction specific surface area, can influence a number of performance and mechanical characteristics of absorbent foams. These include the absorbent capacity for aqueous liquids and the compression deflection characteristics. Foam density will vary according to the state of the foam. Foams in the collapsed state obviously have higher density than the same foam in the fully expanded state. In general, foams in the collapsed state useful for the present invention have a dry density of about 0.11 g/$cm^3$.

Any suitable gravimetric procedure that will provide a determination of mass of solid foam material per unit volume of foam structure can be used to measure foam density. For example, an ASTM gravimetric procedure described more fully in the Test Methods section of U.S. Pat. No. 5,387,207 supra is one method that can be employed for density determination. Foam density pertains to the weight per unit volume of a washed foam free of emulsifiers, fillers, surface treatments such as salts, and the like. The foams useful for the present invention will preferably have dry densities of from about 8 mg/$cm^3$ to about 77 mg/$cm^3$, more preferably from about 11 mg/$cm^3$ to about 63 mg/$cm^3$ still more preferably from about 13 mg/$cm^3$ to about 48 mg/$cm^3$.

Foams useful for the present invention can be obtained by polymerizing a specific type of water-in-oil emulsion or HIPE having a relatively small amount of an oil phase and a relatively greater amount of a water phase. This process comprises the steps of:

A) forming a water-in-oil emulsion at a specified temperature and under specified shear mixing from:
 1) an oil phase comprising:
  a) from about 85 to about 98% by weight of a monomer component capable of forming a copolymer having a Tg of about 35° C. or lower, the monomer component comprising:
   i) from about 30 to about 80% by weight of at least one substantially water-insoluble monofunctional monomer capable of forming an atactic amorphous polymer having a Tg of about 25° C. or lower;
   ii) from about 5 to about 40% by weight of at least one substantially water-insoluble monofunctional comonomer capable of imparting toughness about equivalent to that provided by styrene;
   iii) from about 5 to about 30% by weight of a first substantially water-insoluble, polyfunctional crosslinking agent selected from divinyl benzenes, trivinylbenzenes, divinyltoluenes, divinylxylenes, divinyinaphthalenes divinylalkylbenzenes, divinylphenanthrenes, divinylbiphenyls, divinyldiphenyl-methanes, divinylbenzyls, divinylphenylethers, divinyldiphenylsulfides, divinylfurans, divinylsulfide, divinyl sulfone, and mixtures thereof; and
   iv) from 0 to about 15% by weight of a second substantially water-insoluble, polyfunctional crosslinking agent selected from polyfunctional acrylates, methacrylates, acrylamides, methacryl-amides, and mixtures thereof; and
  b) from about 2 to about 15% by weight of an emulsifier component which is soluble in the oil phase and which is suitable for forming a stable water-in-oil emulsion, the emulsion component comprising: (i) a primary emulsifier having at least about 40% by weight emulsifying components selected from diglycerol monoesters of linear unsaturated $C_{16}$–$C_{22}$ fatty acids, diglycerol monoesters of branched $C_{16}$–$C_{24}$ fatty acids, diglycerol monoaliphatic ethers of branched $C_{16}$–$C_{24}$ alcohols, diglycerol monoaliphatic ethers of linear unsaturated $C_{16}$–$C_{22}$ fatty alcohols, diglycerol monoaliphatic ethers of linear saturated $C_{12}$–$C_{14}$ alcohols, sorbitan monoesters of linear unsaturated $C_{16}$–$C_{22}$ fatty acids, sorbitan monoesters of branched $C_{16}$–$C_{24}$ fatty acids, and mixtures thereof; or (ii) the combination a primary emulsifier having at least 20% by weight of these emulsifying components and certain secondary emulsifiers in a weight ratio of primary to secondary emulsifier of from about 50:1 to about 1:4; and
 2) a water phase comprising an aqueous solution containing: (i) from about 0.2 to about 20% by weight of a water-soluble electrolyte; and (ii) an effective amount of a polymerization initiator;
 3) a volume to weight ratio of water phase to oil phase in the range of from about 12:1 to about 125:1; and
B) polymerizing the monomer component in the oil phase of the water-in-oil emulsion to form a polymeric foam material; and
C) optionally dewatering the polymeric foam material.

The process allows the formation of these absorbent foams that are capable of distributing liquids as a result of having carefully balanced properties as described herein.

These properties are achieved by careful selection of crosslinker and monomer types and levels and emulsion formation parameters, specifically the amount of shear mixing, the temperature, and the water-to-oil ratio (which translates into the final density of the dry foam).

Polymeric foams useful for the present invention can be prepared by polymerization of certain water-in-oil emulsions having a relatively high ratio of water phase to oil phase commonly known in the art as "HIPEs". Polymeric foam materials which result from the polymerization of such emulsions are referred to hereafter as "HIPE foams". A detailed description of the general preparation of such HIPEs is given in U.S. Pat. Nos. 5,563,179 and 5,387,207, infra.

The relative amounts of the water and oil phases used to form the HIPEs are, among many other parameters, important in determining the structural, mechanical and performance properties of the resulting polymeric foams. In particular, the ratio of water to oil ("W:O ratio") in the emulsion varies inversely with ultimate foam density and can influence the cell size and capillary suction specific surface area of the foam and dimensions of the struts that form the foam. The emulsions used to prepare the HIPE foams useful for this invention will generally have a volume to weight ratio of water phase to oil phase in the range of from about 12:1 to about 125:1, and most typically from about 15:1 to about 90:1. Particularly preferred foams can be made from HIPEs having ratios of from about 20:1 to about 75:1.

The major portion of the oil phase of the HIPEs will comprise monomers, comonomers and crosslinking agents such as those enumerated in U.S. Pat. No. 5,387,207 infra. It is essential that these monomers, comonomers and crosslinking agents be substantially water-insoluble so that they are primarily soluble in the oil phase and not the water phase. Use of such substantially water-insoluble monomers ensures that HIPEs of appropriate characteristics and stability will be realized. It is, of course, highly preferred that the monomers, comonomers and crosslinking agents used herein be of the type such that the resulting polymeric foam is suitably non-toxic and appropriately chemically stable. These monomers, comonomers and cross-linking agents should preferably have little or no toxicity if present at very low residual concentrations during post-polymerization foam processing and/or use.

Another essential component of the oil phase is an emulsifier component that permits the formation of stable HIPEs. This emulsifier component comprises a primary emulsifier and optionally a secondary emulsifier, such as those enumerated in U.S. Pat. No. 5,387,207 infra.

The oil phase used to form the HIPEs comprises from about 85 to about 98% by weight monomer component and from about 2 to about 15% by weight emulsifier component. Preferably, the oil phase will comprise from about 90 to about 98% by weight monomer component and from about 3 to about 10% by weight emulsifier component. The oil phase also can contain other optional components. One such optional component is an oil soluble polymerization initiator of the general type well known to those skilled in the art, such as described in U.S. Pat. No. 5,290,820 (Bass et al.), issued Mar. 1, 1994, which is incorporated by reference. Another preferred optional component is an antioxidant such as a Hindered Amine Light Stabilizer (HALS) and Hindered Phenolic Stabilizers (HPS) or any other antioxidant compatible with the initiator system to be employed. Other optional components include plasticizers, fillers, colorants, chain transfer agents, dissolved polymers, and the like.

The discontinuous water internal phase of the HIPE is generally an aqueous solution containing one or more dissolved components such as those enumerated in U.S. Pat. No. 5,387,207 infra. One essential dissolved component of the water phase is a water-soluble electrolyte. The dissolved electrolyte minimizes the tendency of the monomers, comonomers and crosslinkers that are primarily oil soluble to also dissolve in the water phase.

This, in turn, is believed to minimize the extent to which polymeric material fills the cell windows at the oil/water interfaces formed by the water phase droplets during polymerization. Thus, the presence of electrolyte and the resulting ionic strength of the water phase is believed to determine whether and to what degree the resulting preferred polymeric foams can be open-celled.

The HIPEs will also typically contain a polymerization initiator. Such an initiator component is generally added to the water phase of the HIPEs and can be any conventional water-soluble free radical initiator. These include peroxygen compounds such as sodium, potassium and ammonium persulfates, hydrogen peroxide, sodium peracetate, sodium percarbonate and the like. Conventional redox initiator systems can also be used. Such systems are formed by combining the foregoing peroxygen compounds with reducing agents such as sodium bisulfite, L-ascorbic acid or ferrous salts.

The initiator can be present at up to about 20 mole percent based on the total moles of polymerizable monomers present in the oil phase. More preferably, the initiator is present in an amount of from about 0.001 to about 10 mole percent based on the total moles of polymerizable monomers in the oil phase.

The polymer forming the HIPE foam structure will preferably be substantially free of polar functional groups. This means the polymeric foam will be relatively hydrophobic in character. These hydrophobic foams can find utility where the absorption of hydrophobic liquids is desired. Uses of this sort include those where an oily component is mixed with water and it is desired to separate and isolate the oily component, such as in the case of marine oil spills.

When these foams are to be used as absorbents for aqueous liquids such as juice spills, milk, and the like for clean up and/or bodily liquids such as urine, they generally require further treatment to render the foam relatively more hydrophilic. Hydrophilization of the foam, if necessary, can generally be accomplished by treating the HIPE foam with a hydrophilizing surfactant in a manner described in U.S. Pat. No. 5,387,207 infra.

These hydrophilizing surfactants can be any material that enhances the water wettability of the polymeric foam surface. They are well known in the art, and can include a variety of surfactants, preferably of the nonionic type, such as those enumerated in U.S. Pat. No. 5,387,207 infra.

Another material that is typically incorporated into the HIPE foam structure is a hydratable, and preferably hygroscopic or deliquescent, water soluble inorganic salt. Such salts include, for example, toxicologically acceptable alkaline earth metal salts. Salts of this type and their use with oil-soluble surfactants as the foam hydrophilizing surfactant is described in greater detail in U.S. Pat. No. 5,352,711 (DesMarais), issued Oct. 4, 1994, the disclosure of which is incorporated by reference. Preferred salts of this type include the calcium halides such as calcium chloride that, as previously noted, can also be employed as the water phase electrolyte in the HIPE.

Hydratable inorganic salts can easily be incorporated by treating the foams with aqueous solutions of such salts.

These salt solutions can generally be used to treat the foams after completion of, or as part of, the process of removing the residual water phase from the just-polymerized foams. Treatment of foams with such solutions preferably deposits hydratable inorganic salts such as calcium chloride in residual amounts of at least about 0.1% by weight of the foam, and typically in the range of from about 0.1 to about 12%.

Treatment of these relatively hydrophobic foams with hydrophilizing surfactants (with or without hydratable salts) will typically be carried out to the extent necessary to impart suitable hydrophilicity to the foam. Some foams of the preferred HIPE type, however, are suitably hydrophilic as prepared, and can have incorporated therein sufficient amounts of hydratable salts, thus requiring no additional treatment with hydrophilizing surfactants or hydratable salts. In particular, such preferred HIPE foams include those where certain oil phase emulsifiers previously described and calcium chloride are used in the HIPE. In those instances, the internal polymerized foam surfaces will be suitably hydrophilic, and will include residual water-phase liquid containing or depositing sufficient amounts of calcium chloride, even after the polymeric foams have been dewatered to a practicable extent.

Foam preparation typically involves the steps of: 1) forming a stable high internal phase emulsion (HIPE); 2) polymerizing/curing this stable emulsion under conditions suitable for forming a solid polymeric foam structure; 3) optionally washing the solid polymeric foam structure to remove the original residual water phase from the polymeric foam structure and, if necessary, treating the polymeric foam structure with a hydrophilizing surfactant and/or hydratable salt to deposit any needed hydrophilizing surfactant/hydratable salt, and 4) thereafter dewatering this polymeric foam structure. The procedure is described more fully in U.S. Pat. No. 5,387,207 supra.

In order to use respective materials in absorbent structures, these materials can be combined with other elements so as to creating an Fluid handling member, which comprises materials according to the description as laid out in the above.

Storage Absorbent Member Requirements

As described in the above the distribution members exhibit certain desorption properties, which have to be matched by the absorption properties of the absorbent storage members or materials.

Thus, the storage absorbent members suitable for the present invention exhibit high capillary suction capacities. For purposes of the present disclosure, this high suction capacity is measured in terms of the member's ability to uptake fluid at certain capillary heights, which are generally encountered when the member is positioned in an absorbent article. The Capillary Sorption Absorbent Capacity test (also referred to herein as the Capsorption test) measures the amount of test fluid per gram of absorbent storage member that is taken up when the storage member is placed at varying heights on a capillary sorption apparatus. The Capillary Sorption Absorbent Capacity test is described in greater detail in the Test Methods section below.

In one aspect, the high capillary suction capacity storage absorbent member suitable for the present invention has a capillary sorption absorbent capacity (CSAC) at a height of 35 cm of at least about 15 g/g, preferably at least about 18/g, more preferably at least about 20 g/g, still more preferably at least about 22 g/g. Typically, these storage absorbent members will have a capillary sorption absorbent capacity at a height of 35 cm of from about 15 g/g to about 60 g/g, more typically from about 18 g/g to about 50 g/g, still more typically from about 20 g/g to about 40 g/g.

In another aspect, the high capillary suction capacity storage absorbent member can have a CSAC at a height of 50 cm of at least about 8 g/g, preferably at least about 11 g/g, more preferably at least about 15 g/g, still more preferably at least about 19 g/g. Typically, these storage absorbent members will have a CSAC at a height of 50 cm of from about 8 g/g to about 40 g/g, more typically from about 11 g/g to about 35 g/g, still more typically from about 15 g/g to about 30 g/g.

In still another aspect, the high capillary suction capacity storage absorbent member has a CSAC at a height of 80 cm of at least about 6 g/g, preferably at least about 9 g/g, more preferably at least about 12 g/g, still more preferably at least about 15 g/g. Typically, these storage absorbent members will have a capillary sorption absorbent capacity at a height of 80 cm of from about 6 g/g to about 35 g/g, more typically from about 9 g/g to about 30 g/g, still more typically from about 12 g/g to about 25 g/g.

In yet another aspect, the high capillary suction capacity storage absorbent member has a CSAC at a height of 100 cm of at least about 5 g/g, preferably at least about 7 g/g, more preferably at least about 10 g/g, still more preferably at least about 14 g/g. Typically, these storage absorbent members will have a capillary sorption absorbent capacity at a height of 100 cm of from about 5 g/g to about 30 g/g, more typically from about 7 g/g to about 25 g/g, still more typically from about 10 g/g to about 20 g/g.

Though not a requirement, particularly preferred storage absorbent members will have an initial effective uptake rate at 200 cm of at least about 3 g/g/hr, more preferably at least about 4 g/g/hr, and most preferably at least about 8 g/g/hr. Typically, the effective uptake rate at 200 cm will be from about 3 to about 15 g/g/hr, more typically from about 4 to about 12 g/g/hr, still more typically from about 8 to about 12 g/g/hr.

While the above minimum capillary suction capacities are important to the storage absorbent members of the present invention, these members will also preferably, though not necessarily, have a capillary sorption absorbent capacity at zero head pressure (i.e., at 0 cm in the Capsorption test) of at least about 15 g/g. In another preferred aspect, the storage absorbent members will concurrently exhibit the required g/g uptake at least two suction heights discussed above. That is, for example, preferred storage absorbent members will have 2 or more of the following properties: (i) a capillary sorption absorbent capacity (CSAC) at a height of 35 cm of at least about 10 g/g, preferably at least about 13 g/g, more preferably at least about 20 g/g, still more preferably at least about 22 g/g; (ii) a CSAC at a height of 50 cm of at least about 8 g/g, preferably at least about 11 g/g, more preferably at least about 15 g/g, still more preferably at least about 19 g/g; (iii) a CSAC at a height of 80 cm of at least about 6 g/g, preferably at least about 9 g/g, more preferably at least about 12 g/g, still more preferably at least about 15 g/g; (iv) a CSAC at a height of 100 cm of at least about 5 g/g, preferably at least about 7 g/g, more preferably at least about 10 g/g, still more preferably at least about 14 g/g.

A yet another way to describe storage absorbent members suitable for the invention is that the high capillary suction storage absorbent member needs to have a high medium absorption pressure The medium absorption pressure of material is defined as the pressure for which the material has a capillary absorption efficiency of 50% and is measured in the capillary absorption test described in the test method section, by determining the height at which the material will achieve 50% of it's maximum absorption capacity in this test, and is referred to as CSAH 50.

Preferred storage absorbent members suitable for the present invention are high capillary suction capacity storage absorbent members having a capillary sorption absorbent capacity at a height of 0 cm of at least about 15 g/g, preferably at least about 20 g/g, more preferably at least about 25g/g, most preferably at least about 35 g/g and having a medium capillary absorption height CSAH 50 of at least 35 cm, preferably at least 45 cm, more preferably at least 60 cm, most preferably at least 80 cm.

Materials to Achieve Storage Absorbent Member Requirements

High Surface Area Materials

The storage absorbent members useful for the present invention preferably comprise a high surface area material. It is this high surface area material that provides, either itself or in combination with other elements such as hydrogel-forming absorbent polymer, the members with high capillary sorption absorbent capacity. As discussed herein, high surface area materials are described, at least in one regard, in terms of their capillary sorption absorbent capacity (measured without hydrogel-forming polymer if present in the member or any other optional material contained in the actual storage absorbent member, such as adhesives, bonding agents, etc.). It is recognized that materials having high surface areas may have uptake capacities at very high suction heights (e.g., 100 cm or higher). This allows the high surface area materials to provide one or both of the following functions: i) a capillary pathway of liquid to the other absorbents, such as osmotic absorbents, and/or ii) additional absorbent capacity. Thus, while the high surface area materials may be described in terms of their surface area per weight or volume, Applicants herein alternatively use capillary sorption absorbent capacity to describe the high surface area material because capillary sorption absorbent capacity is a performance parameter that generally will provide the absorbent members for the present invention with the requisite suction capabilities to provide improved absorbent articles. It will be recognized that certain high surface area materials, e.g. glass microfibers, will themselves not exhibit particularly high capillary sorption absorbent capacity at all heights, especially very high heights (e.g., 100 cm and higher). Nonetheless, such materials may provide the desired capillary pathway of liquid to the hydrogel-forming absorbent polymer or other absorbents to provide the requisite capillary sorption absorbent capacities, even at relatively high heights.

Any material having sufficient capillary sorption absorbent capacity will be useful in the storage absorbent members of the present invention. In this regard, the term "high surface area material" refers to any material that itself (i.e., as measured without the osmotic absorbent or any other optional material that makes up the storage absorbent member) exhibits one or more of the following capillary sorption absorbent capacities: (I) A capillary sorption absorbent capacity of at least about 2 g/g at a suction height of 100 cm, preferably at least about 3 g/g, still more preferably at least about 4 g/g, and still more preferably at least about 6 g/g, at a height of 100 cm; (II) A capillary sorption absorbent capacity at a height of 35 cm of at least about 5 g/g, preferably at least about 8 g/g, more preferably at least about 12 g/g; (III) A capillary sorption absorbent capacity at a height of 50 cm of at least about 4 g/g, preferably at least about 7 g/g, more preferably at least about 9 g/g; (IV) A capillary sorption absorbent capacity at a height of 140 cm of at least about 1 g/g, preferably at least about 2 g/g, more preferably at least about 3 g/g, still more preferably at least about 5 g/g; or (V) A capillary sorption absorbent capacity at a height of 200 cm of at least about 1 g/g, preferably at least about 2 g/g, more preferably at least about 3 g/g, still more preferably at least about 5 g/g.

In one embodiment, the high surface area material will be fibrous (hereafter referred to as "high surface area fibers") in character, so as to provide a fibrous web or fibrous matrix when combined with the other absorbent such as hydrogel-forming absorbent polymer or other osmotic absorbent. Alternatively, and in a particularly preferred embodiment, the high surface area material will be an open-celled, hydrophilic polymeric foam (hereafter referred to as "high surface area polymeric foams" or more generally as "polymeric foams"). These materials are described in detail below.

High Surface Area Fibers

High surface area fibers useful in the present invention include those that are naturally occurring (modified or unmodified), as well as synthetically made fibers. The high surface area fibers have surface areas much greater than fibers typically used in absorbent articles, such as wood pulp fibers. The high surface area fibers used in the present invention will desirably be hydrophilic. As used herein, the term "hydrophilic" describes fibers, or surfaces of fibers, that are wettable by aqueous liquids (e.g., aqueous body liquids) deposited on these fibers. Hydrophilicity and wettability are typically defined in terms of contact angle and the surface tension of the liquids and solids involved. This is discussed in detail in the American Chemical Society publication entitled Contact Angle, Wettability and Adhesion, edited by Robert F. Gould (Copyright 1964). A fiber, or surface of a fiber, is said to be wetted by a liquid (i.e., hydrophilic) when either the contact angle between the liquid and the fiber, or its surface, is less than 90°, or when the liquid tends to spread spontaneously across the surface of the fiber, both conditions normally co-existing. Conversely, a fiber or surface is considered to be hydrophobic if the contact angle is greater than 90° and the liquid does not spread spontaneously across the surface of the fiber. The hydrophilic character of the fibers useful herein may be inherent in the fibers, or the fibers may be naturally hydrophobic fibers that are treated to render them hydrophilic. Materials and methods for providing hydrophilic character to naturally hydrophobic fibers are well known.

High surface area fibers useful herein will have capillary suction specific surface areas in the same range as the polymeric foams described below. Typically, however, high surface area fibers are characterized in terms of the well known BET surface area.

High surface area fibers useful herein include glass microfibers such as, for example, glass wool available from Evanite Fiber Corp. (Corvallis, Oreg.). Glass microfibers useful herein will typically have fiber diameters of not more than about 0.8 µm, more typically from about 0.1 µm to about 0.7 µm. These microfibers will have surface areas of at least about 2 m²/g, preferably at least about 3 m²/g. Typically, the surface area of glass microfibers will be from about 2 m²/g to about 15 m²/g. Representative glass microfibers for use herein are those available from Evanite Fiber Corp. as type 104 glass fibers, which have a nominal fiber diameter of about 0.5 µm. These glass microfibers have a calculated surface area of about 3.1 m²/g.

Another type of high surface area fibers useful herein are fibrillated cellulose acetate fibers. These fibers (referred to herein as "fibrets") have high surface areas relative to cellulose-derived fibers commonly employed in the absorbent article art. Such fibrets have regions of very small diameters, such that their particle size width is typically from about 0.5 to about 5 μm. These fibrets typically have aggregate surface areas of about 20 m²/g. Representative fibrets useful as the high surface area materials herein are available from Hoechst Celanese Corp. (Charlotte, N.C.) as cellulose acetate Fibrets®. For a detailed discussion of fibrets, including their physical properties and methods for their preparation, see "Cellulose Acetate Fibrets: A Fibrillated Pulp With High Surface Area", Smith, J. E., Tappi Journal, December 1988, p. 237; and U.S. Pat. No. 5,486,410 (Groeger et al.) issued Jan. 23, 1996; the disclosure of each of which is incorporated by reference herein.

In addition to these fibers, the skilled artisan will recognize that other fibers well known in the absorbency art may be modified to provide high surface area fibers for use herein. Representative fibers that may be modified to achieve high surface areas required by the present invention are disclosed in U.S. Pat. No. 5,599,335, supra (see especially columns 21–24).

Regardless of the nature of the high surface area fibers utilized, the fibers and the other absorbent material such as the osmotic absorbent will be discrete materials prior to combination. As used herein, the term "discrete" means that the high surface area fibers and the other absorbents are each formed prior to being combined to form the storage absorbent member. In other words, the high surface area fibers are not formed subsequent to mixing with the other absorbent (e.g., hydrogel-forming absorbent polymer), nor is the other absorbent formed after combination with the high surface area fibers. Combining of the discrete respective components ensures that the high surface area fibers will have the desired morphology and, more importantly, the desired surface area.

High Surface Area Polymeric Foams

The high surface area polymeric foams useful herein are described in some respects below in terms of their physical properties. To measure certain of these properties, it is necessary to perform analysis on the foam in sheet form. Thus, insofar as a foam is used in particulate form and is prepared from a previously formed sheet, physical property measurements will be conducted on the sheet foam (i.e., prior to forming particulates). Where the foam is formed in situ into particles (or beads) during the polymerization process, a similar foam (in terms of chemical composition, cell size, W:O ratio, etc.) can be formed into sheets for the purpose of making such measurements.

High surface area polymeric foams useful in the high capillary suction storage absorbent members of the present invention are known in the art. Particularly preferred foams are those obtained by polymerizing a high internal phase water-in-oil emulsion, such as those described in U.S. Pat. Nos. 5,387,207 and 5,650,222. Other particularly preferred polymeric foams are described in more detail in co-pending U.S. patent application Ser. No. 09/042,429, filed Mar. 13, 1998 by T. DesMarais et al. titled "HIGH Suction Polymeric Foam Materials" (P&G Case 7052), ) and co-pending U.S. patent application Ser. No. 09,042,418, filed Mar. 13, 1998 by T. DesMarais et al. titled "Absorbent Materials for Distributing Aqueous Liquids" (P&G Case 7051), the disclosure of each of which is incorporated by reference herein. (Specific preferred foams described in one or both of these copending applications are described in the Examples section below.) Polymeric foams useful herein are those which are relatively open-celled. This means many of the individual cells of the foam are in unobstructed communication with adjoining cells. The cells in such relatively open-celled foam structures have intercellular openings or "windows" that are large enough to permit ready liquid transfer from one cell to the other within the foam structure.

These relatively open-celled foam structures will generally have a reticulated character with the individual cells being defined by a plurality of mutually connected, three dimensionally branched webs. The strands of polymeric material making up these branched webs can be referred to as "struts." For purposes of the present invention, a most preferred foam material will have at least about 80% of the cells in the foam structure that are at least 1 μm in size in liquid communication with at least one adjacent cell.

In addition to being open-celled, these polymeric foams are sufficiently hydrophilic to permit the foam to absorb aqueous liquids. The internal surfaces of the foam structures are rendered hydrophilic by residual hydrophilizing surfactants left in the foam structure after polymerization, or by selected post-polymerization foam treatment procedures, as described hereafter.

The extent to which these polymeric foams are "hydrophilic" can be quantified by the "adhesion tension" value exhibited when in contact with an absorbable test liquid. The adhesion tension exhibited by these foams can be determined experimentally using a procedure where weight uptake of a test liquid, e.g., synthetic urine, is measured for a sample of known dimensions and capillary suction specific surface area. Such a procedure is described in greater detail in the Test Methods section of U.S. Pat. No. 5,387,207, infra. Foams which are useful high surface area materials in the present invention are generally those which exhibit an adhesion tension value of from about 15 to about 65 dynes/cm, more preferably from about 20 to about 65 dynes/cm, as determined by capillary absorption of synthetic urine having a surface tension of 65±5 dynes/cm.

The polymeric foams useful herein are preferably prepared in the form of collapsed (i.e., unexpanded), polymeric foams that, upon contact with aqueous liquids, absorb such liquids and expand when the amount absorbed lowers the combined capillary pressure plus confining pressure to below the expansion pressure (described below) of the foam. These collapsed polymeric foams are usually obtained by expressing the water phase from the polymerized HIPE foam through compressive forces, and/or thermal drying and/or vacuum dewatering. After compression, and/or thermal drying/vacuum dewatering, these polymeric foams are in a collapsed, or unexpanded state.

Figure 3:
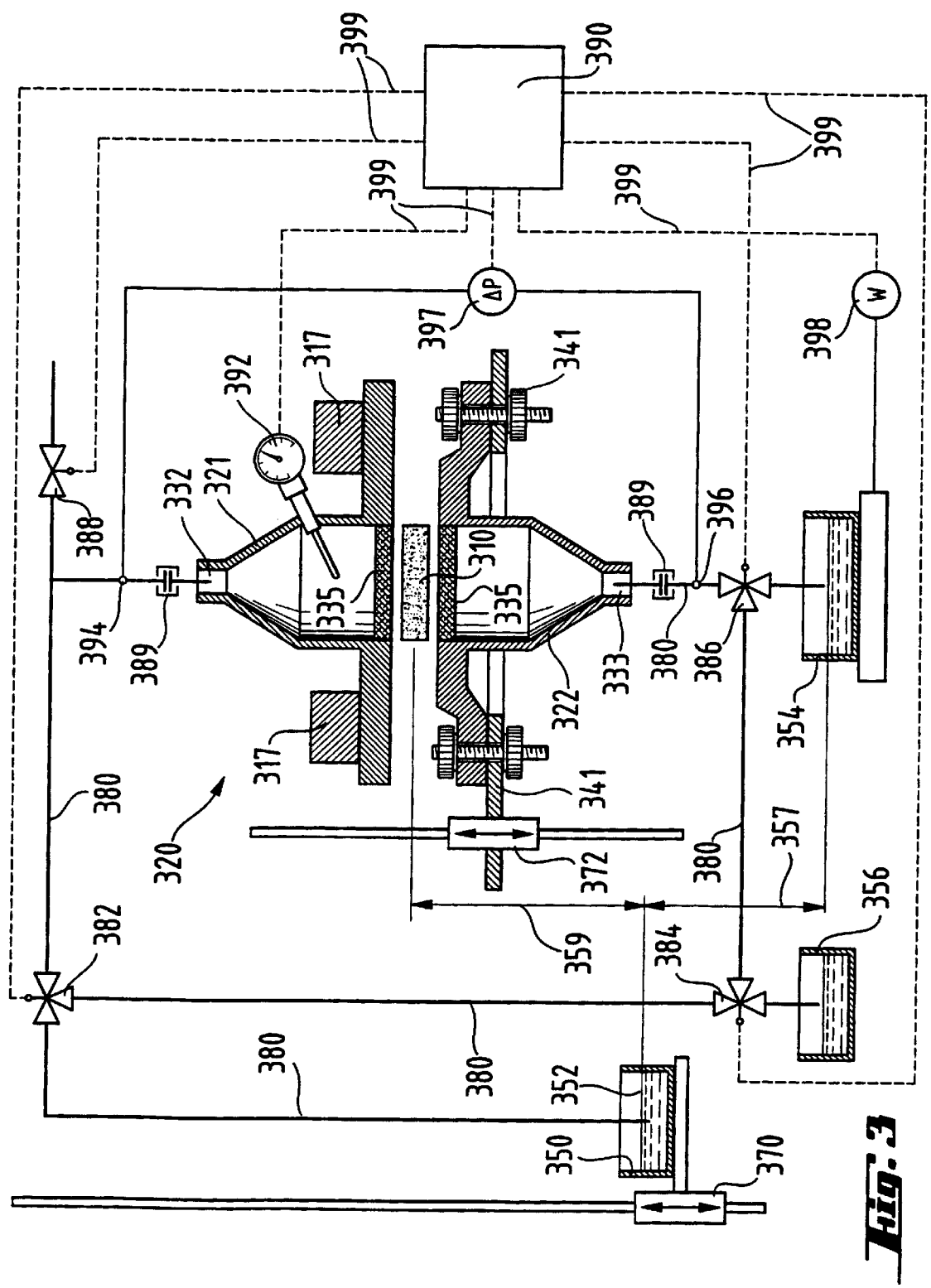
Figure 5A:
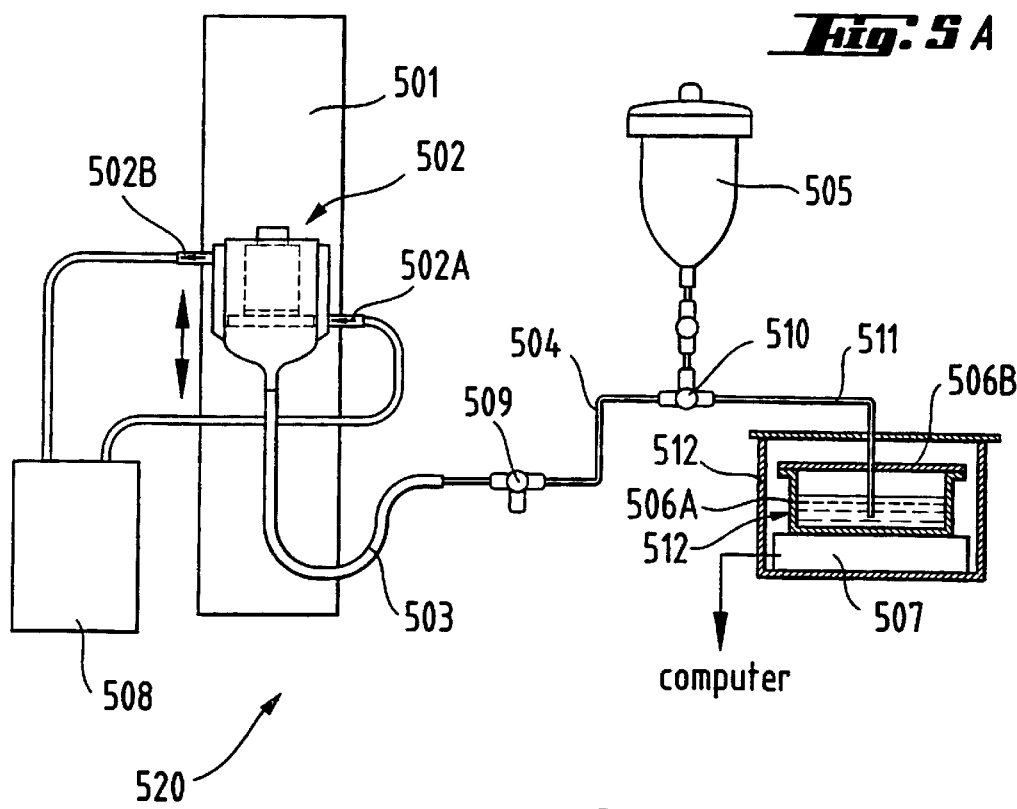
FIG. 5—Shows the Capillary Sorption test stand (Capsorption)
Figure 5D:
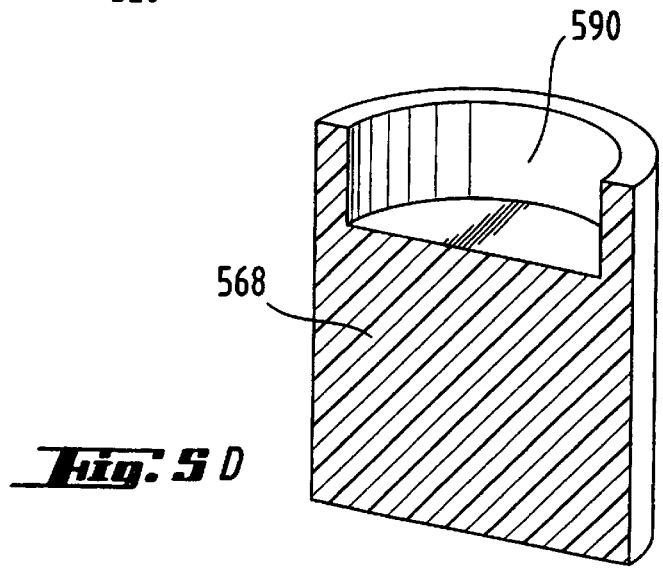
Figure 5B:
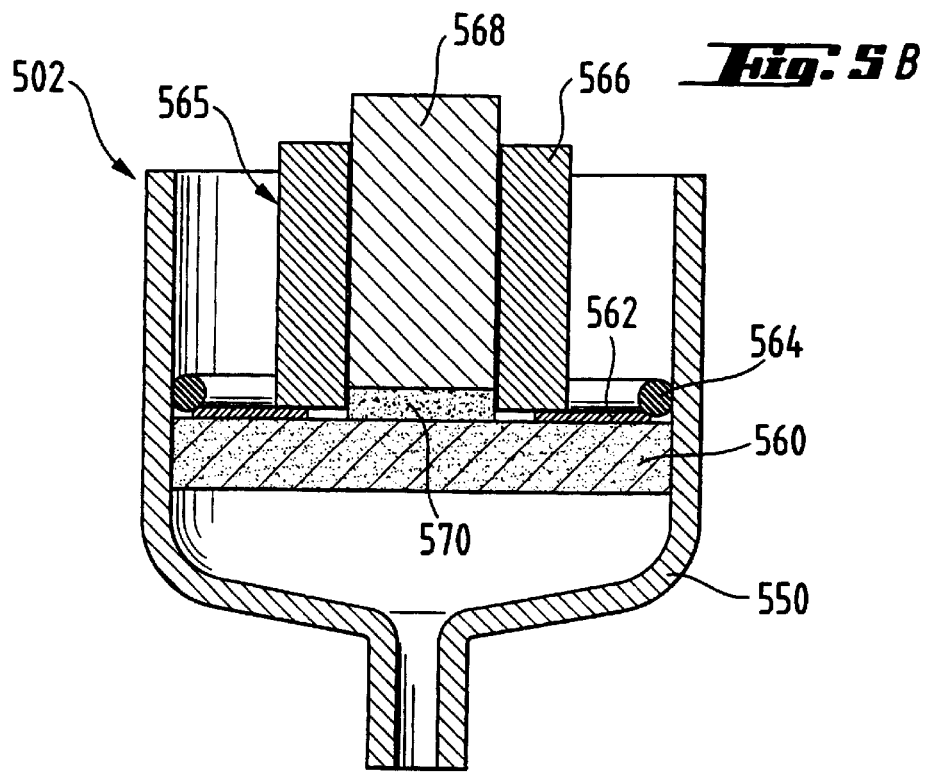
Figure 5C:
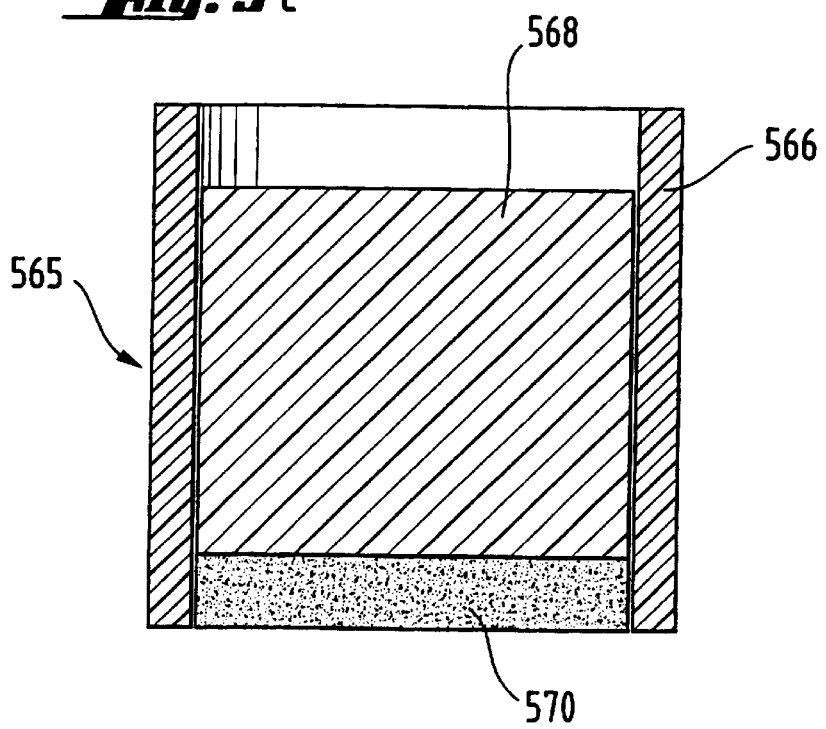

The cellular structure of a representative collapsed HIPE foam from which water has been expressed by compression is shown in the photomicrograph of FIGS. 3 and 4 of U.S. Pat. No. 5,650,222, discussed above. As shown in these figures, the cellular structure of the foam is distorted, especially when compared to the expanded HIPE foam structures shown in FIGS. 1 and 2 of the '222 patent. As can also be seen in FIGS. 3 and 4 of the '222 patent, the voids or pores (dark areas) in the collapsed foam structure have been flattened or elongated. (It is noted that the foams depicted in the '222 patent are in sheet form; as discussed below, while foams in sheet forms are useful herein, in a preferred embodiment, the foam will be in particulate form.) The cellular structure of another HIPE-derived foam (in its expanded state) useful herein is depicted in FIGS. 3 and 4 herein. The preparation of this particular foam and related foams are described herein in Examples 2 through 4, and these very high surface area foams are described in more detail in co-pending U.S. patent application Ser. No. 09,042,429, filed Mar. 13, 1998 by T. DesMarais et al. titled "High Suction Polymeric Foam Materials" (P&G Case 7052), ) and co-pending U.S. patent application Ser. No 09,042,418, filed Mar. 13, 1998 by T. DesMarais et al. titled "Absorbent Materials for Distributing Aqueous Liquids" (P&G Case 7051), the disclosure of each of which is incorporated by reference herein.

Following compression and/or thermal drying/vacuum dewatering, the collapsed polymeric foam may reexpand when wetted with aqueous liquids. Surprisingly, these polymeric foams remain in this collapsed, or unexpanded, state for significant periods of time, e.g., up to at least about 1 year. The ability of these polymeric foams to remain in this collapsed/unexpanded state is believed to be due to capillary forces, and in particular the capillary pressures developed within the foam structure. As used herein, "capillary pressures" refers to the pressure differential across the liquid/air interface due to the curvature of meniscus within the narrow confines of the pores in the foam. [See Chatterjee, "Absorbency," *Textile Science and Technology*, Vol. 7, 1985, p. 36.]

After compression, and/or thermal drying/vacuum dewatering to a practicable extent, these polymeric foams have residual water that includes both the water of hydration associated with the hygroscopic, hydrated salt incorporated therein, as well as free water absorbed within the foam. This residual water (assisted by the hydrated salts) is believed to exert capillary pressures on the resulting collapsed foam structure. Collapsed polymeric foams of the present invention can have residual water contents of at least about 4%, typically from about 4 to about 40%, by weight of the foam when stored at ambient conditions of 72° F. (22° C.) and 50% relative humidity. Preferred collapsed polymeric foams have residual water contents of from about 5 to about 30% by weight of the foam.

A key parameter of these foams is their glass transition temperature. The Tg represents the midpoint of the transition between the glassy and rubbery states of the polymer. Foams that have a higher Tg than the temperature of use can be very strong but will also be rigid and potentially prone to fracture. Such foams also typically take a long time to recover to the expanded state when wetted with aqueous liquids colder than the Tg of the polymer after having been stored in the collapsed state for prolonged periods. The desired combination of mechanical properties, specifically strength and resilience, typically necessitates a fairly selective range of monomer types and levels to achieve these desired properties.

For foams useful in the present invention, the Tg should be as low as possible, so long as the foam has acceptable strength at in-use temperatures. Accordingly, monomers are selected as much as possible that provide corresponding homopolymers having lower Tg's. It has been found that the chain length of the alkyl group on the acrylate and methacrylate comonomers can be longer than would be predicted from the Tg of the homologous homopolymer series. Specifically, it has been found that the homologous series of alkyl acrylate or methacrylate homopolymers have a minimum Tg at a chain length of 8 carbon atoms. By contrast, the minimum Tg of the copolymers of the present invention occurs at a chain length of about 12 carbon atoms. (While the alkyl substituted styrene monomers can be used in place of the alkyl acrylates and methacrylates, their availability is currently extremely limited).

The shape of the glass transition region of the polymer can also be important, i.e., whether it is narrow or broad as a function of temperature. This glass transition region shape is particularly relevant where the in-use temperature (usually ambient or body temperature) of the polymer is at or near the Tg. For example, a broader transition region can mean an incomplete transition at in-use temperatures. Typically, if the transition is incomplete at the in-use temperature, the polymer will evidence greater rigidity and will be less resilient. Conversely, if the transition is completed at the in-use temperature, then the polymer will exhibit faster recovery from compression when wetted with aqueous liquids. Accordingly, it is desirable to control the Tg and the breadth of the transition region of the polymer to achieve the desired mechanical properties. Generally, it is preferred that the Tg of the polymer be at least about 10° C. lower than the in-use temperature. (The Tg and the width of the transition region are derived from the loss tangent vs. temperature curve from a dynamic mechanical analysis (DMA) measurement, as described in the Test Methods section of U.S. Pat. No. 5,650,222).

While the high surface area materials in general have been described in terms of their capillary sorption absorbent capacity, the high surface area polymeric foams useful herein may also be described in terms of their capillary suction specific surface area (hereafter referred to as "CSSSA"). In general, CSSSA is a measure of the test-liquid-accessible surface area of the polymeric network forming a particular foam per unit mass of the bulk foam material (polymer structural material plus solid residual material). Capillary suction specific surface area is determined both by the dimensions of the cellular units in the foam and by the density of the polymer, and is thus a way of quantifying the total amount of solid surface provided by the foam network to the extent that such a surface participates in absorbency. For purposes of characterizing the foams useful herein, CSSSA is measured on a sheet of the foam in question, even where the foam is in particle form when incorporated in a storage absorbent member.

The CSSSA of a foam is particularly relevant to whether the foam will provide the requisite capillary suction for use in preparing storage absorbent members of the present invention. This is because the capillary pressure developed within the foam structure is proportional to the capillary suction specific surface area. In addition, the CSSSA is relevant to whether adequate capillary pressures are developed within the foam structure to keep it in a collapsed state until wetted with aqueous liquids. Assuming other factors such as the foam density and adhesion tension are constant, this means that, as the CSSSA is increased (or decreased), the capillary pressure within the foam structure also increases (or decreases) proportionately.

For purposes of the present invention, CSSSA is determined by measuring the amount of capillary uptake of a low surface tension liquid (e.g., ethanol) which occurs within a foam sample of a known mass and dimensions. A detailed description of such a procedure for determining foam specific surface area is set forth in the Test Methods section of U.S. Pat. No. 5,387,207, which is incorporated by reference. Any reasonable alternative method for determining CSSSA can also be utilized.

The collapsed polymeric foams of the present invention useful as absorbents are those that have a CSSSA of at least about 3 $m^2/g$. Typically, the CSSSA is in the range from about 3 to about 30 $m^2/g$, preferably from about 4 to about 17 $m^2/g$, most preferably from about 5 to about 15 $m^2/g$. Foams having such CSSSA values (with expanded state densities of from about 0.010 to about 0.033 $g/cm^3$) will generally possess an especially desirable balance of absorbent capacity, liquid-retaining and liquid-wicking or distribution characteristics for aqueous liquids such as urine. In addition, foams having such CSSSA can develop a sufficient capillary pressure to keep the foam in a collapsed, unexpanded state until wetted with such aqueous liquids.

As discussed above, for particularly preferred collapsable polymeric foams, in their collapsed state the capillary pressures developed within the foam structure at least equal the forces exerted by the elastic recovery or modulus of the compressed polymer. In other words, the capillary pressure necessary to keep the collapsed foam relatively thin is determined by the countervailing force exerted by the compressed polymeric foam as it tries to "spring back." The elastic recovery tendency of polymeric foams can be estimated from stress-strain experiments where the expanded foam is compressed to about ⅙ (17%) of its original, expanded thickness and then held in this compressed state until a relaxed stress value is measured. Alternatively, and for the purposes of the present invention, the relaxed stress value is estimated from measurements on the polymeric foam in its collapsed state when in contact with aqueous liquids, e.g., water. This alternative relaxed stress value is hereafter referred to as the "expansion pressure" of the foam. The expansion pressure for collapsed polymeric foams of the present invention is about 50 kiloPascals (kPa) or less and typically from about 7 to about 40 kPa. A detailed description of a procedure for estimating the expansion pressure of foams is set forth in the Test Methods section of U.S. Pat. No. 5,387,207.

Another important property of the high surface area polymeric foams useful in the present invention is their free absorbent capacity. "Free absorbent capacity" (or "FAC") is the total amount of test liquid (synthetic urine) which a given foam sample will absorb into its cellular structure per unit mass of solid material in the sample. To be especially useful in the storage absorbent members of the present invention, the polymeric foams should have a free absorbent capacity of from about 30 to about 100 ml, preferably from about 30 to about 75 ml of synthetic urine per gram of dry foam material. The procedure for determining the free absorbent capacity of the foam is described hereafter in the Test Methods section of U.S. Pat. No. 5,650,222.

Upon exposure to aqueous liquids, preferred collapsed polymeric foams absorb the liquids and expand. The polymeric foams, in their expanded state, absorb more liquid than most other foams. The "expansion factor" for these foams is at least about 4×, i.e. the thickness of the foam in its expanded state is at least about 4 times the thickness of the foam in its collapsed state. The collapsed foams preferably have an expansion factor in the range of from about 4× to about 15×, more preferably from about 5× to about 10×.

For the purposes of the present invention, the relationship between expanded and collapsed thickness for compressively dewatered foams can be empirically predicted from the following equation:

$$\text{thickness}_{expanded} = \text{thickness}_{collapsed} \times ((0.133 \times \text{W:O ratio}) \pm 2)$$

where:
  $\text{thickness}_{expanded}$ is the thickness of the foam in its expanded state;
  $\text{thickness}_{collapsed}$ is the thickness of the foam in its collapsed state;
  and W:O ratio is the water-to-oil ratio of the HIPE from which the foam is made. Thus, a typical polymeric foam made from an emulsion with a water-to-oil ratio of 60:1 would have a predicted expansion factor of 8.0, i.e., an expanded thickness 8 times the collapsed thickness of the foam.

The procedure for measuring the expansion factor is described hereafter in the Test Methods section of U.S. Pat. No. 5,650,222.

A relevant mechanical feature of the high surface area polymeric foams useful in the present invention is their strength in their expanded state, as determined by resistance to compression deflection (RTCD). The RTCD exhibited by the foams herein is a function of the polymer modulus, as well as the density and structure of the foam network. The polymer modulus is, in turn, determined by: a) the polymer composition; b) the conditions under which the foam is polymerized (for example, the completeness of polymerization obtained, specifically with respect to crosslinking); and c) the extent to which the polymer is plasticized by residual material, e.g., emulsifiers, left in the foam structure after processing.

To be useful as the high surface area portion of the absorbent members of the present invention, the polymeric foams should be suitably resistant to deformation or compression by forces encountered in use. Foams which do not possess sufficient foam strength in terms of RTCD may provide the requisite capillary suction capacity under no-load conditions but will not provide those capacities under the compressive stress caused by the motion and activity of the user of the absorbent articles that contain the foam.

The RTCD exhibited by the polymeric foams useful in the present invention can be quantified by determining the amount of strain produced in a sample of saturated foam held under a certain confining pressure for a specified temperature and period of time. The method for carrying out this particular type of test is described hereafter in the Test Methods section of U.S. Pat. No. 5,650,222. Foams useful herein will preferably exhibit a RTCD such that a confining pressure of 5.1 kPa produces a strain of typically about 90% or less compression of the foam structure when it has been saturated to its free absorbent capacity with synthetic urine having a surface tension of 65±5 dynes/cm. Preferably the strain produced under such conditions will be in the range from about 1 to about 90%, more preferably from about 1 to about 25%, still more preferably from about 2 to about 10%, still more preferably from about 2 to about 5%.

The high surface area polymeric foams useful herein can be also be described in terms of their vertical hang sorption height (hereafter "VHSH"). The VHSH height at X % is the height in cm where X % of the 0 cm capacity (or FAC) is retained in the foam. A typical value of importance is the VHSH at 90%, though in principle X may be any value. The most reproducible measure for VHSH is achieved at X=90%, within the experience of the inventors. It will be obvious to one skilled in the art that this single point value does not fully express the shape of the curve obtained in a plot of capacity vs. height. The single point however serves as a practical point of comparison for the foams useful herein. In this regard, the foams will typically have an equilibrium 90% VHSH of at least about 20 cm, preferably at least about 40 cm, still more preferably at least about 60 cm, still more preferably at least about 70 cm and still more preferably at least about 80 cm. Typically, preferred polymeric foams will have a 90% VHSH of from about 20 to about 90 cm, more typically from about 60 to about 90 cm, more typically from about 70 to about 90 cm, still more typically from, about 80 to about 90 cm. The method for measuring 90% VHSH is described in detail in the Test Methods section below. As indicated, where the high surface area polymeric foam is in particulate form when combined with the other absorbent, such as an osmotic absorbent, 90% VHSH is measured on the corresponding foam in sheet form (i.e., prior to forming particulates). Where the foam is formed into particles (or beads) during the polymerization process, a similar foam can be formed into sheets for assessing the foam's 90% VHSH.

Foam cells, and especially cells that are formed by polymerizing a monomer-containing oil phase that surrounds relatively monomer-free water-phase droplets, will frequently be substantially spherical in shape. The size or "diameter" of such spherical cells is a commonly used parameter for characterizing foams in general. Since cells in a given sample of polymeric foam will not necessarily be of approximately the same size, an average cell size, i.e., average cell diameter, will often be specified.

A number of techniques are available for determining the average cell size of foams. The most useful technique, however, for determining cell size in foams involves a simple measurement based on the scanning electron photomicrograph of a foam sample.

The cell size measurements given herein are based on the number average cell size of the foam in its expanded state, e.g., as shown in FIG. 1 of U.S. Pat. No. 5,650,222. The foams useful in accordance with the present invention will preferably have a number average cell size of about 80 $\mu$m or less, and typically from about 5 to about 50 $\mu$m. "Foam density" (i.e., in grams of foam per cubic centimeter of foam volume in air) is specified herein on a dry basis. The amount of absorbed water-soluble residual materials, e.g., residual salts and liquid left in the foam, for example, after HIPE polymerization, washing and/or hydrophilization, is disregarded in calculating and expressing foam density. Foam density does include, however, other water-insoluble residual materials such as emulsifiers present in the polymerized foam. Such residual materials can, in fact, contribute significant mass to the foam material.

Any suitable gravimetric procedure that will provide a determination of mass of solid foam material per unit volume of foam structure can be used to measure foam density. For example, an ASTM gravimetric procedure described more fully in the Test Methods section of U.S. Pat. No. 5,387,207 (Dyer et al.) issued Feb. 7, 1995, supra, is one method that can be employed for density determination. In their collapsed state, polymeric foams useful in the present invention have dry basis density values (exclusive of any residual salts and or water) in the range of from about 0.1 to about 0.2 g/cm$^3$, preferably from about 0.11 to about 0.19 g/cm$^3$, and most preferably from about 0.12 to about 0.17 g/cm$^3$. In their expanded state, polymeric foams useful herein will have dry basis density values in the range of from about 0.01 to about 0.033 g/cm$^3$, preferably from about 0.013 to about 0.033 g/cm$^3$.

Vertical wicking, i.e., liquid wicking in a direction opposite from gravitational force, is a desirable performance attribute for polymeric foams useful herein. For the purposes of this invention, vertical wicking rate is reflective of the permeability of the material, and thus, the ability of the material to deliver liquid to the other absorbent, such as a hydrogel-forming absorbent polymer or other osmotic absorbent.

Vertical wicking rate is determined by measuring the time taken for a colored test liquid (e.g., synthetic urine) in a reservoir to wick a vertical distance of 5 cm through a test strip of foam of specified size. The vertical wicking procedure is described in greater detail in the Test Methods section of U.S. Pat. No. 5,387,207, but is performed at 31° C., instead of 37° C. To be especially useful in absorbent members for absorbing urine, the foams useful herein will preferably wick synthetic urine (65±5 dynes/cm) to a height of 5 cm in no more than about 15 minutes. More preferably, the preferred foam absorbents of the present invention wick synthetic urine to a height of 5 cm in no more than about 10 minutes.

The vertical wicking absorbent capacity test measures the amount of test liquid per gram of absorbent foam that is held within each one in. (2.54 cm) vertical section of the same standard size foam sample used in the vertical wicking test. Such a determination is generally made after the sample has been allowed to vertically wick test liquid to equilibrium (e.g., after about 18 hours). Like the vertical wicking test, the vertical wicking absorbent capacity test is described in greater detail in the Test Methods section of U.S. Pat. No. 5,387,207 (Dyer et al.) issued Feb. 7, 1995, supra. High vertical wicking absorbent capacities at high heights are theoretically equivalent to high capillary sorption absorbent capacities at high heights. Since the sheet form of the foams useful herein is amenable to the former test and the former test is more easily and cheaply performed, the data from the former test are recommended as the means of characterizing this important parameter of the foams of this invention.

While high capillary suction foams may be in sheet form when combined with other absorbent such as osmotic absorbent (e.g., hydrogel-forming absorbent polymer), in a particularly preferred embodiment, the polymeric foam will be in particle form and will be mixed with particles of hydrogel-forming polymer to provide a blend. That is, while the foam may initially be prepared in sheet form, these sheets may be processed to provide particles of foam, which are then combined with the hydrogelling polymer. As discussed above, the foams useful herein, and processes for their preparation, are described in great detail in U.S. Pat. Nos. 5,387,207, 5,650,222, co-pending U.S. patent application Ser. No. 09/042,429, filed Mar. 13,1998 by T. DesMarais et al. titled "High Suction Polymeric Foam Materials" (P&G Case 7052), and co-pending U.S. patent application Ser. No. 09/042,418, filed Mar. 13, 1998 by T. DesMarais et al. titled "Absorbent Materials for Distributing Aqueous Liquids" (P&G Case 7051). Foam particles may be prepared by first forming a sheet of foam per the teachings of these references, followed by mechanical processing the foam to provide particles (e.g., pulverizing, cutting, chopping, etc.) of the desired dimension. Alternatively, foam particles may be prepared directly from emulsion in the form of polymeric microbeads, as described in U.S. Pat. No. 5,653,922, issued Aug. 5, 1997 to Li et al., and U.S. Pat. No. 5,583,162, issued Dec. 10, 1996 to Li et al., the disclosure of each of which is incorporated by reference herein. Specific embodiments for making polymer foam/hydrogel-forming polymer blends are discussed in more detail below.

Applicants have also found that the high surface area foams may optionally comprise a fluid so as to provide increased transfer of urine to the other absorbent or osmotic absorbent of the storage absorbent member. The pre-wetting fluid partially fills the polymeric foam and, without wishing to be held to a particular theory, increases the uptake rate of the foam. Ideally, polymeric foam comprising pre-wetting fluid(s) should be shelf stable, with sufficiently low water activity to prevent microbial growth and prevent evaporative water loss and not migrate out of the foam over time. Water can be used as a pre-wetting fluid to provide the absorption performance but may not by itself meet the other requirements.

Hydrogel-Forming Absorbent Polymers

The storage absorbent members of the present invention further preferably comprise at least one hydrogel-forming absorbent polymer (also referred to as hydrogel-forming polymer). Hydrogel-forming polymers useful in the present invention include a variety of water-insoluble, but water-swellable polymers capable of absorbing large quantities of liquids. Such hydrogel-forming polymers are well known in the art and any of these materials are useful in the high capillary suction absorbent members of the present invention.

Hydrogel-forming absorbent polymers materials are also commonly referred to as "hydrocolloids," or "superabsorbent" materials and can include polysaccharides such as carboxymethyl starch, carboxymethyl cellulose, and hydroxypropyl cellulose; nonionic types such as polyvinyl alcohol, and polyvinyl ethers; cationic types such as polyvinyl pyridine, polyvinyl morpholinione, and N,N-dimethylaminoethyl or N,N-diethylaminopropyl acrylates and methacrylates, and the respective quaternary salts thereof. Typically, hydrogel-forming absorbent polymers useful in the present invention have a multiplicity of anionic, functional groups, such as sulfonic acid, and more typically carboxy, groups. Examples of polymers suitable for use herein include those which are prepared from polymerizable, unsaturated, acid-containing monomers. Thus, such monomers include the olefinically unsaturated acids and anhydrides that contain at least one carbon to carbon olefinic double bond. More specifically, these monomers can be selected from olefinically unsaturated carboxylic acids and acid anhydrides, olefinically unsaturated sulfonic acids, and mixtures thereof. As indicated above, the nature of the hydrogel-forming absorbent polymer is not critical to the members of the present invention. Nonetheless, the selection of the optimal polymeric material may enhance the performance characteristics of the present members. The disclosure that follows describes preferred properties of the absorbent polymers useful herein. These properties should not be interpreted as limitations; rather, they merely indicate the progression that has occurred in the absorbent polymer art over the past several years.

Some non-acid monomers can also be included, usually in minor amounts, in preparing the hydrogel-forming absorbent polymers herein. Such non-acid monomers can include, for example, the water-soluble or water-dispersible esters of the acid-containing monomers, as well as monomers that contain no carboxylic or sulfonic acid groups at all. Optional non-acid monomers can thus include monomers containing the following types of functional groups: carboxylic acid or sulfonic acid esters, hydroxyl groups, amide-groups, amino groups, nitrile groups, quaternary ammonium salt groups, aryl groups (e.g., phenyl groups, such as those derived from styrene monomer). These non-acid monomers are well-known materials and are described in greater detail, for example, in U.S. Pat. No. 4,076,663 (Masuda et al.), issued Feb. 28, 1978, and in U.S. Pat. No. 4,062,817 (Westerman), issued Dec. 13, 1977, both of which are incorporated by reference.

Olefinically unsaturated carboxylic acid and carboxylic acid anhydride monomers include the acrylic acids typified by acrylic acid itself, methacrylic acid, ethacrylic acid, α-chloroacrylic acid, a-cyanoacrylic acid, β-methylacrylic acid (crotonic acid), α-phenylacrylic acid, β-acryloxypropionic acid, sorbic acid, α-chlorosorbic acid, angelic acid, cinnamic acid, p-chlorocinnamic acid, β-sterylacrylic acid, itaconic acid, citroconic acid, mesaconic acid, glutaconic acid, aconitic acid, maleic acid, fumaric acid, tricarboxyethylene and maleic acid anhydride.

Olefinically unsaturated sulfonic acid monomers include aliphatic or aromatic vinyl sulfonic acids such as vinylsulfonic acid, allyl sulfonic acid, vinyl toluene sulfonic acid and styrene sulfonic acid; acrylic and methacrylic sulfonic acid such as sulfoethyl acrylate, sulfoethyl methacrylate, sulfopropyl acrylate, sulfopropyl methacrylate, 2-hydroxy-3-methacryloxypropyl sulfonic acid and 2-acrylamide-2-methylpropane sulfonic acid.

Preferred hydrogel-forming absorbent polymers for use in the present invention contain carboxy groups. These polymers include hydrolyzed starch-acrylonitrile graft copolymers, partially neutralized hydrolyzed starch- acrylonitrile graft copolymers, starch-acrylic acid graft copolymers, partially neutralized starch-acrylic acid graft copolymers, saponified vinyl acetate-acrylic ester copolymers, hydrolyzed acrylonitrile or acrylamide copolymers, slightly network crosslinked polymers of any of the foregoing copolymers, partially neutralized polyacrylic acid, and slightly network crosslinked polymers of partially neutralized polyacrylic acid. These polymers can be used either solely or in the form of a mixture of two or more different polymers. Examples of these polymer materials are disclosed in U.S. Pat. Nos. 3,661,875, 4,076,663, 4,093,776, 4,666,983, and 4,734,478.

Most preferred polymer materials for use in making the hydrogel-forming absorbent polymers are slightly network crosslinked polymers of partially neutralized polyacrylic acids and starch derivatives thereof. Most preferably, the hydrogel-forming absorbent polymers comprise from about 50 to about 95%, preferably about 75%, neutralized, slightly network crosslinked, polyacrylic acid (i.e., poly (sodium acrylate/acrylic acid)). Network crosslinking renders the polymer substantially water-insoluble and, in part, determines the absorptive capacity and extractable polymer content characteristics of the hydrogel-forming absorbent polymers. Processes for network crosslinking these polymers and typical network crosslinking agents are described in greater detail in U.S. Pat. No. 4,076,663.

While the hydrogel-forming absorbent polymer is preferably of one type (i.e., homogeneous), mixtures of polymers can also be used in the present invention. For example, mixtures of starch-acrylic acid graft copolymers and slightly network crosslinked polymers of partially neutralized polyacrylic acid can be used in the present invention.

The hydrogel-forming polymer component may also be in the form of a mixed-bed ion-exchange composition comprising a cation-exchange hydrogel-forming absorbent polymer and an anion-exchange hydrogel-forming absorbent polymer. Such mixed-bed ion-exchange compositions are described in, e.g., PCT Publication WO 99/34843 by Hird, et al. (P&G Case 6975—titled "Absorbent Polymer Compositions Having High Sorption Capacities Under an Applied Pressure"); PCT Publication WO 99/34841 by Ashraf, et al. (P&G Case 6976—titled "Absorbent Polymer Compositions with High Sorption Capacity and High Fluid Permeability Under an Applied Pressure"); and U.S. Pat. No. 6,121,509, filed Jan. 7, 1998 by Ashraf, et al. (P&G Case 6977—titled "Absorbent Polymer Compositions Having High Sorption Capacities Under an Applied Pressure and Improved Intergrity in the Swollen State"); the disclosure of each of which is incorporated herein by reference.

The hydrogel-forming absorbent polymers useful in the present invention can have a size, shape and/or morphology varying over a wide range. These polymers can be in the form of particles that do not have a large ratio of greatest dimension to smallest dimension (e.g., granules, pulverulents, interparticle aggregates, interparticle crosslinked aggregates, and the like) and can be in the form of fibers, sheets, films, foams, flakes and the like. The hydrogel-forming absorbent polymers can also comprise mixtures with low levels of one or more additives, such as for example powdered silica, surfactants, glue, binders, and the like. The components in this mixture can be physically and/or chemically associated in a form such that the hydrogel-forming polymer component and the nonhydrogel-forming polymer additive are not readily physically separable.

The hydrogel-forming absorbent polymers can be essentially non-porous (i.e., no internal porosity) or have substantial internal porosity.

For particles as described above, particle size is defined as the dimension determined by sieve size analysis. Thus, for example, a particle that is retained on a U.S.A. Standard Testing Sieve with 710 micron openings (e.g., No. 25 U.S. Series Alternate Sieve Designation) is considered to have a size greater than 710 microns; a particle that passes through a sieve with 710 micron openings and is retained on a sieve with 500 micron openings (e.g., No. 35 U.S, Series Alternate Sieve Designation) is considered to have a particle size between 500 and 710 $\mu$m; and a particle that passes through a sieve with 500 micron openings is considered to have a size less than 500 $\mu$m. The mass median particle size of a given sample of hydrogel-forming absorbent polymer particles is defined as the particle size that divides the sample in half on a mass basis, i.e., one-half of the sample by weight will have a particle size less than the mass median size and one-half of the sample will have a particle size greater than the mass median size. A standard particle-size plotting method (wherein the cumulative weight percent of the particle sample retained on or passed through a given sieve size opening is plotted versus sieve size opening on probability paper) is typically used to determine mass median particle size when the 50% mass value does not correspond to the size opening of a U.S.A. Standard Testing Sieve. These methods for determining particle sizes of the hydrogel-forming absorbent polymer particles are further described in U.S. Pat. No. 5,061,259 (Goldman et al.), issued Oct. 29, 1991, which is incorporated by reference.

For particles of hydrogel-forming absorbent polymers useful in the present invention, the particles will generally range in size from about 1 to about 2000 $\mu$m, more preferably from about 20 to about 1000 $\mu$m. The mass median particle size will generally be from about 20 to about 1500 $\mu$m, more preferably from about 50 $\mu$m to about 1000 $\mu$m, and even more preferably from about 100 to about 800 $\mu$m.

Where relatively high concentrations (e.g. 40%, 60%, or greater, by weight) of hydrogel forming absorbent polymer are utilized in the absorbent members of the present invention, still other properties of the absorbent polymer may be relevant. In such embodiments, the materials may have one or more of the properties described by U.S. Pat. No. 5,562,646, issued Oct. 8, 1996 to Goldman et al. and U.S. Pat. No. 5,599,335, issued Feb. 4, 1997 to Goldman et al., the disclosure of each of which is incorporated by reference herein.

The basic hydrogel-forming absorbent polymer can be formed in any conventional manner. Typical and preferred processes for producing these polymers are described in U.S. Reissue Patent 32,649 (Brandt et al.), issued Apr. 19, 1988, U.S. Pat. No. 4,666,983 (Tsubakimoto et al.), issued May 19, 1987, and U.S. Pat. No. 4,625,001 (Tsubakimoto et al.), issued Nov. 25, 1986, all of which are incorporated by reference.

Preferred methods for forming the basic hydrogel-forming absorbent polymer are those involving aqueous solution or other solution polymerization methods. As described in the above-referenced U.S. Patent Reissue 32,649, aqueous solution polymerization involves the use of an aqueous reaction mixture to carry out polymerization. The aqueous reaction mixture is then subjected to polymerization conditions which are sufficient to produce in the mixture, substantially water-insoluble, slightly network crosslinked polymer. The mass of polymer formed can then be pulverized or chopped to form individual particles.

More specifically, the aqueous solution polymerization method for producing the hydrogel-forming absorbent polymer comprises the preparation of an aqueous reaction mixture in which to carry out the polymerization. One element of such a reaction mixture is the acid group-containing monomer that will form the "backbone" of the hydrogel-forming absorbent polymer to be produced. The reaction mixture will generally comprise about 100 parts by weight of the monomer. Another component of the aqueous reaction mixture comprises a network crosslinking agent. Network crosslinking agents useful in forming the hydrogel-forming absorbent polymer according to the present invention are described in more detail in the above-referenced U.S. Reissue Pat. No. 32,649, U.S. Pat. Nos. 4,666,983, and 4,625,001. The network crosslinking agent will generally be present in the aqueous reaction mixture in an amount of from about 0.001 mole percent to about 5 mole percent based on the total moles of monomer present in the aqueous mixture (about 0.01 to about 20 parts by weight, based on 100 parts by weight of the monomer). An optional component of the aqueous reaction mixture comprises a free radical initiator including, for example, peroxygen compounds such as sodium, potassium, and ammonium persulfates, caprylyl peroxide, benzoyl peroxide, hydrogen peroxide, cumene hydroperoxides, tertiary butyl diperphthalate, tertiary butyl perbenzoate, sodium peracetate, sodium percarbonate, and the like. Other optional components of the aqueous reaction mixture comprise the various non-acidic co-monomers, including esters of the essential unsaturated acidic functional group-containing monomers or other co-monomers containing no carboxylic or sulfonic acid functionalities at all.

The aqueous reaction mixture is subjected to polymerization conditions which are sufficient to produce in the mixture substantially water-insoluble, but water-swellable, hydrogel-forming absorbent slightly network crosslinked polymers. The polymerization conditions are also discussed in more detail in the three above-referenced patents. Such polymerization conditions generally involve heating (thermal activation techniques) to a polymerization temperature from about 0° to about 100° C., more preferably from about 5° to about 40° C. Polymerization conditions under which the aqueous reaction mixture is maintained can also include, for example, subjecting the reaction mixture, or portions thereof, to any conventional form of polymerization activating irradiation. Radioactive, electronic, ultraviolet, or electromagnetic radiation are alternative conventional polymerization techniques.

The acid functional groups of the hydrogel-forming absorbent polymer formed in the aqueous reaction mixture are also preferably neutralized. Neutralization can be carried out in any conventional manner that results in at least about 25 mole percent, and more preferably at least about 50 mole percent, of the total monomer utilized to form the polymer being acid group-containing monomers that are neutralized with a salt-forming cation. Such salt-forming cations include, for example, alkali metals, ammonium, substituted ammonium and amines as discussed in further detail in the above-references U.S. Reissue Pat. No. 32,649.

While it is preferred that the particulate versions of hydrogel-forming absorbent polymer be manufactured using an aqueous solution polymerization process, it is also possible to carry out the polymerization process using multi-phase polymerization processing techniques such as inverse emulsion polymerization or inverse suspension polymerization procedures. In the inverse emulsion polymerization or inverse suspension polymerization procedures, the aqueous reaction mixture as described before is suspended in the form of tiny droplets in a matrix of a water-immiscible, inert organic solvent such as cyclohexane. The resultant particles of hydrogel-forming absorbent polymer are generally spherical in shape. Inverse suspension polymerization procedures are described in greater detail in U.S. Pat. No. 4,340,706 (Obaysashi et al.), issued Jul. 20, 1982, U.S. Pat. No. 4,506,052 (Flesher et al.), issued Mar. 19, 1985, and U.S. Pat. No. 4,735,987 (Morita et al.), issued Apr. 5, 1988, all of which are incorporated by reference.

Surface crosslinking of the initially formed polymers is a preferred process for obtaining hydrogel-forming absorbent polymers having relatively high porosity hydrogel-layer ("PHL"), performance under pressure ("PUP") capacity and saline flow conductivity ("SFC") values, which may be beneficial in the context of the present invention. Suitable general methods for carrying out surface crosslinking of hydrogel-forming absorbent polymers according to the present invention are disclosed in U.S. Pat. No. 4,541,871 (Obayashi), issued Sep. 17, 1985; published PCT application WO92/16565 (Stanley), published Oct. 1, 1992, published PCT application WO90/08789 (Tai), published Aug. 9, 1990; published PCT application WO93/05080 (Stanley), published Mar. 18, 1993; U.S. Pat. No. 4,824,901 (Alexander), issued Apr. 25, 1989; U.S. Pat. No. 4,789,861 (Johnson), issued Jan. 17, 1989; U.S. Pat. No. 4,587,308 (Makita), issued May 6, 1986; U.S. Pat. No. 4,734,478 (Tsubakimoto), issued Mar. 29, 1988; U.S. Pat. No. 5,164,459 (Kimura et al.), issued Nov. 17, 1992; published German patent application 4,020,780 (Dahmen), published Aug. 29, 1991; and published European patent application 509,708 (Gartner), published Oct. 21, 1992; all of which are incorporated by reference. See also, U.S. Pat. No. 5,562,646 (Goldman et al.), issued Oct. 8, 1996, and U.S. Pat. No. 5,599,335 (Goldman et al.), issued Feb. 4, 1997.

The hydrogel-forming absorbent polymer particles prepared according to the present invention are typically substantially dry. The term "substantially dry" is used herein to mean that the particles have a liquid content, typically water or other solution content, less than about 50%, preferably less than about 20%, more preferably less than about 10%, by weight of the particles. In general, the liquid content of the hydrogel-forming absorbent polymer particles is in the range of from about 0.01% to about 5% by weight of the particles. The individual particles can be dried by any conventional method such as by heating. Alternatively, when the particles are formed using an aqueous reaction mixture, water can be removed from the reaction mixture by azeotropic distillation. The polymer-containing aqueous reaction mixture can also be treated with a dewatering solvent such as methanol. Combinations of these drying procedures can also be used. The dewatered mass of polymer can then be chopped or pulverized to form substantially dry particles of the hydrogel-forming absorbent polymer.

Combination of High Capillary Suction Materials

Whilst materials as described in the above can satisfy the requirements as such (e.g. a pure hydrogel forming material, or a pure foam material), preferred members for being used as storage absorbent member comprise two or more of the materials. This allows often to utilize materials which on their own do not satisfy the criteria, but the combination does.

The principle function of such fluid storage members is to absorb the discharged body fluid either directly or from other absorbent members (e.g., fluid acquisition/distribution members), and then retain such fluid, even when subjected to pressures normally encountered as a result of the wearer's movements.

Thus, high capillary suction absorbent members can be made by combination of hydrogel forming materials with high surface area materials.

The amount of hydrogel-forming absorbent polymer contained in the absorbent member may vary significantly. Furthermore, the concentration of hydrogel may vary throughout a given member. In other words, a member may have regions of relatively higher and relatively lower hydrogel concentration.

In measuring the concentration of hydrogel-forming absorbent polymer in a given region of an absorbent member, the percent by weight of the hydrogel-forming polymer relative to the combined weight of hydrogel-forming polymer and any other components (e.g., fibers, polymeric foams, etc.) that are present in the region containing the hydrogelling polymer is used. With this in mind, the concentration of the hydrogel-forming absorbent polymers in a given region of an absorbent member of the present invention can be at least about 50%, at least about 60%, at least about 70%, or at least about 80%, by total weight of the absorbent member.

Notwithstanding the fact that regions of an absorbent member may comprise relatively high concentrations of hydrogel-forming absorbent polymer, where the high surface area material is fibrous in nature, the aggregate concentration of absorbent polymer in a given absorbent member (i.e., total weight of the hydrogel-forming absorbent polymer divided by the total weight of the absorbent member×100%) will be up to about 75% by weight, preferably up to about 70% by weight, more preferably up to about 65% by weight. Then, with these high surface area fiber-containing members, the concentration of the hydrogel-forming absorbent polymer will be from about 10 to about 75% by weight, more typically from about 15 to about 70% by weight, still more typically from about 20 to about 65% by weight.

In those embodiments where the high surface area material is a polymeric foam, the absorbent members will preferably comprise at least about 1% by weight (on an aggregate basis), more preferably at least about 10% by weight, more preferably at least about 15% by weight, still more preferably at least about 20% by weight, polymeric foam. Typically, such storage absorbent members will comprise from about 1 to about 98% by weight, more typically from about 10 to about 90% by weight, still more typically from about 15 to about 85% by weight, and still more typically from about 20 to about 80% by weight, of the polymeric foam material. As discussed above, these weight % ranges are based on the aggregate weights of the respective materials in an absorbent member; it is recognized that regions of the absorbent member may contain greater and lesser amounts of the materials.

Of course, the relative levels of the absorbent polymer and high surface area material will be dictated by, for example, the absorptive capacity of the hydrogel-forming absorbent polymer, the specific high surface area material used, the nature of the high surface area material (e.g., sheet or particle foam, particle size), etc. In this regard, although high levels of hydrogel-forming absorbent polymer provide absorbent members for making thin absorbent articles, to achieve the requisite level of capillary suction discussed above, there must be sufficient high surface area material to provide such suction capacity. Thus, where relatively higher capillary suction foam is used, higher levels of hydrogel-forming polymer may be employed. Conversely, where relatively lower capillary suction fibers are used, somewhat lower leves of hydrogel-forming polymer will be employed.

(Of course, where both high surface area fibers and polymeric foams are employed, the level of total high surface area material may vary, again depending on the relative concentration of each of these materials.) It is the difference in capillary sorption capacity between the polymeric foams and high surface area fibers described above that accounts for the different ranges of hydrogel-forming polymer to be used in a given absorbent member.

As another example of a material that will provide integrity of the mixture, in absorbent members comprising a blend of hydrogel-forming polymer and high surface area fibers and/or particulate polymeric foam, the member can comprise a thermoplastic material. Upon melting, at least a portion of this thermoplastic material migrates to the intersections of the respective member components, typically due to interparticle or interfiber capillary gradients. These intersections become bond sites for the thermoplastic material. When cooled, the thermoplastic materials at these intersections solidify to form the bond sites that hold the matrix of materials together.

Optional thermoplastic materials useful herein can be in any of a variety of forms including particulates, fibers, or combinations of particulates and fibers. Thermoplastic fibers are a particularly preferred form because of their ability to form numerous bond sites. Suitable thermoplastic materials can be made from any thermoplastic polymer that can be melted at temperatures that will not extensively damage the materials that comprise absorbent member. Preferably, the melting point of this thermoplastic material will be less than about 190° C., and preferably between about 75° C. and about 175° C. In any event, the melting point of this thermoplastic material should be no lower than the temperature at which the thermally bonded absorbent structures, when used in absorbent articles, are likely to be stored. The melting point of the thermoplastic material is typically no lower than about 50° C.

The thermoplastic materials, and in particular the thermoplastic fibers, can be made from a variety of thermoplastic polymers, including polyolefins such as polyethylene (e.g., PULPEX®) and polypropylene, polyesters, copolyesters, polyvinyl acetate, polyethylvinyl acetate, polyvinyl chloride, polyvinylidene chloride, polyacrylics, polyamides, copolyamides, polystyrenes, polyurethanes and copolymers of any of the foregoing such as vinyl chloride/vinyl acetate, and the like. One preferred thermoplastic binder fiber is PLEXAFIL® polyethylene microfibers (made by DuPont) that are also available as an about 20% blend with 80% cellulosic fibers sold under the tradename KITTYHAWK® (made by Weyerhaeuser Co.) Depending upon the desired characteristics for the resulting thermally bonded absorbent member, suitable thermoplastic materials include hydrophobic fibers that have been made hydrophilic, such as surfactant-treated or silica-treated thermoplastic fibers derived from, for example, polyolefins such as polyethylene or polypropylene, polyacrylics, polyamides, polystyrenes, polyurethanes and the like. The surface of the hydrophobic thermoplastic fiber can be rendered hydrophilic by treatment with a surfactant, such as a nonionic or anionic surfactant, e.g., by spraying the fiber with a surfactant, by dipping the fiber into a surfactant or by including the surfactant as part of the polymer melt in producing the thermoplastic fiber. Upon melting and resolidification, the surfactant will tend to remain at the surfaces of the thermoplastic fiber. Suitable surfactants include nonionic surfactants such as Brij® 76 manufactured by ICI Americas, Inc. of Wilmington, Del., and various surfactants sold under the Pegosperse® trademark by Glyco Chemical, Inc. of Greenwich, Conn. Besides nonionic surfactants, anionic surfactants can also be used. These surfactants can be applied to the thermoplastic fibers at levels of, for example, from about 0.2 to about 1 g. per sq. of centimeter of thermoplastic fiber.

Suitable thermoplastic fibers can be made from a single polymer (monocomponent fibers), or can be made from more than one polymer (e.g., bicomponent fibers). As used herein, "bicomponent fibers" refers to thermoplastic fibers that comprise a core fiber made from one polymer that is encased within a thermoplastic sheath made from a different polymer. The polymer comprising the sheath often melts at a different, typically lower, temperature than the polymer comprising the core. As a result, these bicomponent fibers provide thermal bonding due to melting of the sheath polymer, while retaining the desirable strength characteristics of the core polymer.

Suitable bicomponent fibers for use in the present invention can include sheath/core fibers having the following polymer combinations: polyethylene/polypropylene, polyethylvinyl acetate/polypropylene, polyethylene/polyester, polypropylene/polyester, copolyester/polyester, and the like. Particularly suitable bicomponent thermoplastic fibers for use herein are those having a polypropylene or polyester core, and a lower melting copolyester, polyethylvinyl acetate or polyethylene sheath (e.g., DANAKLON®, CELBOND® or CHISSO® bicomponent fibers). These bicomponent fibers can be concentric or eccentric. As used herein, the terms "concentric" and "eccentric" refer to whether the sheath has a thickness that is even, or uneven, through the cross-sectional area of the bicomponent fiber. Eccentric bicomponent fibers can be desirable in providing more compressive strength at lower fiber thicknesses. Suitable bicomponent fibers for use herein can be either uncrimped (i.e. unbent) or crimped (i.e. bent). Bicomponent fibers can be crimped by typical textile means such as, for example, a stuffer box method or the gear crimp method to achieve a predominantly two-dimensional or "flat" crimp.

In the case of thermoplastic fibers, their length can vary depending upon the particular melt point and other properties desired for these fibers. Typically, these thermoplastic fibers have a length from about 0.3 to about 7.5 cm long, preferably from about 0.4 to about 3.0 cm long, and most preferably from about 0.6 to about 1.2 cm long. The properties, including melt point, of these thermoplastic fibers can also be adjusted by varying the diameter (caliper) of the fibers. The diameter of these thermoplastic fibers is typically defined in terms of either denier (grams per 9000 meters) or decitex (grams per 10,000 meters). Suitable bicomponent thermoplastic fibers can have a decitex in the range from about 1.0 to about 20, preferably from about 1.4 to about 10, and most preferably from about 1.7 to about 3.3.

The compressive modulus of these thermoplastic materials, and especially that of the thermoplastic fibers, can also be important. The compressive modulus of thermoplastic fibers is affected not only by their length and diameter, but also by the composition and properties of the polymer or polymers from which they are made, the shape and configuration of the fibers (e.g., concentric or eccentric, crimped or uncrimped), and like factors. Differences in the compressive modulus of these thermoplastic fibers can be used to alter the properties, and especially the density characteristics, of the respective absorbent members during preparation of the absorbent core.

Other Fluid Handling Member Components and Materials

Storage absorbent members according to the present invention can include other optional components that can be present in absorbent webs. For example, a reinforcing scrim can be positioned within the storage absorbent member, or between the respective absorbent members of the absorbent core. Such reinforcing scrims should be of such configuration as to not form interfacial barriers to liquid transfer, especially if positioned between the respective absorbent members of the absorbent core. In addition, several binders may be used to provide dry and wet integrity to the absorbent core and/or the absorbent storage member itself. In particular, hydrophilic glue fibers may be used to provide bonds between the high surface area materials and the other absorbent such as osmotic absorbent material. This is in particular critical for particulate high surface area materials. It is preferred that the amount of binder used is as low as possible, so as not to impair the capillary sorption properties of the absorbent member. However, the skilled artisan will recognize that there are also binders that may enhance the capillary sorption properties of the absorbent member such as fiberized hydrophilic glue with sufficiently high surface area. In this case, the high surface area hydrophilic glue may provide both the liquid handling function and the integrity function, in one material. Also, the respective absorbent member, or the entire absorbent core, can be enveloped within a liquid pervious sheet, such as a tissue paper sheet, to obviate user concern regarding loose particulate absorbent polymer, as long as the capillary continuity is not disturbed.

Other optional components that can be included are materials to control odor, contain fecal matter, etc. Also, any absorbent member comprising particulate osmotic absorbent or high surface area material, or the entire absorbent core, can be enveloped within a liquid pervious sheet, such as a tissue paper sheet, to obviate user concern regarding loose particulate absorbent polymer.

When integrity is introduced via a binder material, suitable binders are melt-blown adhesives such as those described in U.S. Pat. No. 5,560,878, issued Oct. 1, 1996 to Dragoo et al., the disclosure of which is incorporated herein by reference. Processes for combining melt-blown adhesives with the requisite hydrogel-forming polymer and high surface area material is also described in detail in the '878 patent.

EXAMPLES

Samples 1, 2, 3-HIPEs as Distribution Material

The following Samples A.5 to A.7 are of the polymeric foam type, and are prepared as described generally in the Examples section of U.S. Pat. No. 5,563,179, supra. Generally, this process comprises appropriate mixing of an aqueous phase containing selected salts with an oil phase containing selected monomers and emulsifiers. The aqueous phase typically contains an initiator such as potassium persulfate and inorganic salt such as calcium chloride. The oil phase typically contains a blend of monomers such as 2-ethylhexylacrylate and crosslinking monomers such as divinyl benzene (which contains ethyl styrene as an impurity) and 1,6-hexanedioldiacrylate. Adjuvants such as antioxidants, opacifying agents, pigments, dyes, fillers, and other generally unreactive chemicals, can also be added to either phase.

The separate streams of the oil phase and water phase (typically heated to between about 30° and about 90° C.) are fed to a dynamic mixing apparatus. Thorough mixing of the combined streams in the dynamic mixing apparatus is achieved by means of a pin impeller. The ratio of the aqueous phase and the oil phase, referred to as the "water-to-oil ratio", or W:O, is used to control the density of the ultimate foam produced. A detailed description of the apparatus and the procedures for establishing the initial HIPE formation is described in more detail in the Examples section of U.S. Pat. No. 5,563,179, supra.

Once the apparatus set-up is filled, agitation is begun in the dynamic mixer, with the impeller turning at a specified RPM. The flow rate of the water phase is then steadily increased to a rate of 44.1 cm$^3$/sec in a time period of about 30 sec. and the oil phase flow rate is reduced to 1.25 g/sec over a time period of about 1 min. The back pressure created by the dynamic and static mixers at this point is typically between about 3 and about 8 PSI (about 21 to about 55 kPa). The impeller speed is then adjusted to the desired RPM over a period of 120 sec. The system back pressure responds to this adjustment and remains constant thereafter.

The HIPE from the static mixer is collected in a round polypropylene tub, 17 in. (43 cm) in. diameter and 7.5 in. (10 cm) high, with a concentric insert made of Celcon plastic. The insert is 5.0 in. (12.7 cm) in diameter at its base and 4.75 in. (12 cm) in diameter at its top and is 6.75 in. (17.1 cm) high. The HIPE-containing tubs are kept in a room maintained at 65° C. for 18 hours to cure and provide a polymeric HIPE foam.

The cured HIPE foam is removed from the tubs. The foam at this point contains residual water phase (containing dissolved emulsifiers, electrolyte, initiator residues, and initiator). The foam is sliced with a sharp reciprocating saw blade into sheets of desired thickness. These sheets are then subjected to compression in a series of 2 porous nip rolls equipped with vacuum which gradually reduces the residual water phase content of the foam to about 2 times (2×) the weight of the polymerized monomers. At this point, the sheets are then resaturated with a 4% CaCl$_2$ solution at 60° C., are squeezed in a series of 3 porous nip rolls equipped with vacuum to a water phase content of about 2×. The CaCl$_2$ content of the foam is between 2 and 10%.

The HIPE foam is then dried in air for about 16 hours or thermally dried continuously. Such drying reduces the moisture content to about 4–20% by weight of polymerized material.

Sample 1

Anhydrous calcium chloride (36.32 kg) and potassium persulfate (189 g) are dissolved in 378 liters of water. This provides the water phase stream to be used in a continuous process for forming a HIPE emulsion.

To a monomer combination comprising distilled divinylbenzene (39% divinylbenzene and 61% ethyl styrene) (2640 g), 2-ethylhexyl acrylate (4720 g), and hexanedioldiacrylate (640 g) is added a diglycerol monooleate emulsifier (480 g), ditallow dimethyl ammonium methyl suflate (80 g), and Tinuvin 765 (20 g). The diglycerol monooleate emulsifier (Grindsted Products; Brabrand, Denmark) comprises approximately 81% diglycerol monooleate, 1% other diglycerol monoesters, 3% polyols, and 15% other polyglycerol esters, imparts a minimum oil/water interfacial tension value of approximately 2.7 dyne/cm and has an oil/water critical aggregation concentration of approximately 2.8 wt %. After mixing, this combination of materials is allowed to settle overnight. No visible residue is formed and all of the mixture is withdrawn and used as the oil phase in a continuous process for forming a HIPE emulsion.

Separate streams of the oil phase (25° C.) and water phase (53°–55° C.) are fed to a dynamic mixing apparatus. Thorough mixing of the combined streams in the dynamic mixing apparatus is achieved by means of a pin impeller. The pin impeller comprises a cylindrical shaft of about 36.5 cm in length with a diameter of about 2.9 cm. The shaft holds 6 rows of pins, 3 rows having 33 pins and 3 rows having 34 pins, each of the three pins at each level disposed at an angle of 120° to each other, with the next level down disposed at 60° to its neighboring level with each level separated by 0.03 mm, each pin having a diameter of 0.5 cm extending outwardly from the central axis of the shaft to a length of 2.3 cm. The pin impeller is mounted in a cylindrical sleeve which forms the dynamic mixing apparatus, and the pins have a clearance of 1.5 mm from the walls of the cylindrical sleeve.

A minor portion of the effluent exiting the dynamic mixing apparatus is withdrawn and enters a recirculation zone, as shown in the Figure in co-pending U.S. patent application Ser. No. 08/716,510 (T. A. DesMarais), filed Sep. 17, 1996 (herein incorporated by reference). The Waukesha pump in the recirculation zone returns the minor portion to the entry point of the oil and water phase flow streams to the dynamic mixing zone.

A spiral static mixer is mounted downstream from the dynamic mixing apparatus to provide back pressure in the dynamic mixing apparatus and to provide improved incorporation of components into the HIPE that is eventually formed. The static mixer (TAH Industries Model 100-812) has 12 elements with a 1 inch (2.5 cm) outside diameter. A hose is mounted downstream from the static mixer to facilitate delivery of the emulsion to the device used for curing. Optionally an additional static mixer is used to provide addition back pressure to keep the hose filled. The optional static mixer can be a 1 inch (2.5 cm) pipe, 12 element mixer (McMaster-Carr Model 3529K53).

The combined mixing and recirculation apparatus set-up is filled with oil phase and water phase at a ratio of 4 parts water to 1 part oil. The dynamic mixing apparatus is vented to allow air to escape while filling the apparatus completely. The flow rates during filling are 7.57 g/sec oil phase and 30.3 cm$^3$/sec water phase.

Once the apparatus set-up is filled, agitation is begun in the dynamic mixer, with the impeller turning at 850 RPM and recirculation is begun at a rate of about 30 cm$^3$/sec. The flow rate of the water phase is then steadily increased to a rate of 151.3 cm$^3$/sec over a time period of about 1 min., and the oil phase flow rate is reduced to 2.52 g/sec over a time period of about 3 min. The recirculation rate is steadily increased to about 150 cm$^3$/sec during the latter time period. The back pressure created by the dynamic zone and static mixers at this point is about 4.9 PSI (33.8 kPa), which represents the total pressure drop of the system. The Waukesha pump speed is then steadily decreased to a yield a recirculation rate of about 75 cm$^3$/sec.

The HIPE flowing from the static mixer at this point is collected in a round polyethylene tub, 40 in. (102 cm) in diameter and 12.5 in (31.8 cm) high, with removable sides, much like a springform pan used in cooking cakes. A pipe-like polyethylene insert 12.5 in (31.8 cm) in diameter at its base is firmly affixed to the center of the base and is 12.5 in (31.8 cm) high. The HIPE-containing tubs are kept in a room maintained at 65° C. for 18 hours to bring about polymerization and form the foam.

The cured HIPE foam is removed from the curing tubs. The foam at this point has residual water phase (containing dissolved emulsifiers, electrolyte, initiator residues, and initiator) about 55–65 times (55–65×) the weight of polymerized monomers. The foam is sliced with a sharp reciprocating saw blade into sheets which are 0.2 inches (5.1 mm) in thickness. These sheets are then subjected to compression in a series of 2 porous nip rolls equipped with vacuum which gradually reduce the residual water phase content of the foam to about 3 times (3×) the weight of the polymerized material. At this point, the sheets are then resaturated with a 4% CaCl$_2$ solution at 60° C., are squeezed in a series of 3 porous nip rolls equipped with vacuum to a water phase content of about 1.5–2×. The CaCl$_2$ content of the foam is between 6 and 10%.

The foam remains compressed after the final nip at a thickness of about 0.027 in. (0.069 cm). The foam is then dried in air for about 16 hours. Such drying reduces the moisture content to about 9–17% by weight of polymerized material. At this point, the foam sheets are very drapeable.

Sample 2

Anhydrous calcium chloride (36.32 kg) and potassium persulfate (189 g) are dissolved in 378 liters of water. This provides the water phase stream to be used in a continuous process for forming a HIPE emulsion.

To a monomer combination comprising distilled divinylbenzene (42.4% divinylbenzene and 57.6% ethyl styrene) (2640 g), 2-ethylhexyl acrylate (4400 g), and hexanedioldiacrylate (960 g) is added a diglycerol monooleate emulsifier (640 g), ditallow dimethyl ammonium methyl suflate (80 g), and Tinuvin 765 (20 g). The diglycerol monooleate emulsifier (Grindsted Products; Brabrand, Denmark) comprises approximately 81% diglycerol monooleate, 1% other diglycerol monoesters, 3% polyols, and 15% other polyglycerol esters, imparts a minimum oil/water interfacial tension value of approximately 2.7 dyne/cm and has an oil/water critical aggregation concentration of approximately 2.8 wt %. After mixing, this combination of materials is allowed to settle overnight. No visible residue is formed and all of the mixture is withdrawn and used as the oil phase in a continuous process for forming a HIPE emulsion.

Separate streams of the oil phase (25° C.) and water phase (75°–77° C.) are fed to a dynamic mixing apparatus. Thorough mixing of the combined streams in the dynamic mixing apparatus is achieved by means of a pin impeller. The pin impeller comprises a cylindrical shaft of about 36.5 cm in length with a diameter of about 2.9 cm. The shaft holds 6 rows of pins, 3 rows having 33 pins and 3 rows having 34 pins, each of the three pins at each level disposed at an angle of 120° to each other, with the next level down disposed at 60° to its neighboring level with each level separated by 0.03 mm, each pin having a diameter of 0.5 cm extending outwardly from the central axis of the shaft to a length of 2.3 cm. The pin impeller is mounted in a cylindrical sleeve which forms the dynamic mixing apparatus, and the pins have a clearance of 1.5 mm from the walls of the cylindrical sleeve.

A minor portion of the effluent exiting the dynamic mixing apparatus is withdrawn and enters a recirculation zone, as shown in the Figure in co-pending U.S. patent application Ser. No. 08/716,510 (T. A. DesMarais), filed Sep. 17, 1996 (herein incorporated by reference). The Waukesha pump in the recirculation zone returns the minor portion to the entry point of the oil and water phase flow streams to the dynamic mixing zone.

A spiral static mixer is mounted downstream from the dynamic mixing apparatus to provide back pressure in the dynamic mixing apparatus and to provide improved incorporation of components into the HIPE that is eventually formed. The static mixer (TAH Industries Model 101-212) normally has 12 elements with a 1.5 inch (3.8 cm) outside diameter, but 7 inches (17.8 cm) were removed to fit in the equipment space. A hose is mounted downstream from the static mixer to facilitate delivery of the emulsion to the device used for curing. Optionally an additional static mixer is used to provide addition back pressure to keep the hose filled. The optional static mixer can be the same as the first without modification.

The combined mixing and recirculation apparatus set-up is filled with oil phase and water phase at a ratio of 4 parts water to 1 part oil. The dynamic mixing apparatus is vented to allow air to escape while filling the apparatus completely. The flow rates during filling are 7.57 g/sec oil phase and 30.3 cm$^3$/sec water phase.

Once the apparatus set-up is filled, agitation is begun in the dynamic mixer, with the impeller turning at 800 RPM and recirculation is begun at a rate of about 30 cm$^3$/sec. The flow rate of the water phase is then steadily increased to a rate of 151.3 cm$^3$/sec over a time period of about 1 min., and the oil phase flow rate is reduced to 2.52 g/sec over a time period of about 3 min. The recirculation rate is steadily increased to about 150 cm$^3$/sec during the latter time period. The back pressure created by the dynamic zone and static mixers at this point is about 4.2 PSI (29 kPa), which represents the total pressure drop of the system.

The HIPE flowing from the static mixer at this point is collected in a round polyethylene tub, 40 in. (102 cm) in diameter and 12.5 in (31.8 cm) high, with removable sides, much like a springform pan used in cooking cakes. A pipe-like polyethylene insert 12.5 in (31.8 cm) in diameter at its base is firmly affixed to the center of the base and is 12.5 in (31.8 cm) high. The HIPE-containing tubs are kept in a room maintained at 65° C. for 18 hours to bring about polymerization and form the foam.

The cured HIPE foam is removed from the curing tubs. The foam at this point has residual water phase (containing dissolved emulsifiers, electrolyte, initiator residues, and initiator) about 58–62 times (58–62×) the weight of polymerized monomers. The foam is sliced with a sharp reciprocating saw blade into sheets which are 0.2 inches (5.1 mm) in thickness. These sheets are then subjected to compression in a series of 2 porous nip rolls equipped with vacuum which gradually reduce the residual water phase content of the foam to about 6 times (6×) the weight of the polymerized material. At this point, the sheets are then resaturated with a 1.5% CaCl$_2$ solution at 60° C., are squeezed in a series of 3 porous nip rolls equipped with vacuum to a water phase content of about 2×. The CaCl$_2$ content of the foam is between 3 and 6%.

The foam remains compressed after the final nip at a thickness of about 0.047 in. (0.071 cm). The foam is then dried in air for about 16 hours. Such drying reduces the moisture content to about 9–17% by weight of polymerized material. At this point, the foam sheets are very drapeable.

Sample 3

Anhydrous calcium chloride (36.32 kg) and potassium persulfate (189 g) are dissolved in 378 liters of water. This provides the water phase stream to be used in a continuous process for forming a HIPE emulsion.

To a monomer combination comprising distilled divinylbenzene (42.4% divinylbenzene and 57.6% ethyl styrene) (2640 g), 2-ethylhexyl acrylate (4400 g), and hexanedioldiacrylate (960 g) is added a diglycerol monooleate emulsifier (640 g), ditallow dimethyl ammonium methyl suflate (80 g), and Tinuvin 765 (40 g). The diglycerol monooleate emulsifier (Grindsted Products; Brabrand, Denmark) comprises approximately 81% diglycerol monooleate, 1% other diglycerol monoesters, 3% polyols, and 15% other polyglycerol esters, imparts a minimum oil/water interfacial tension value of approximately 2.7 dyne/cm and has an oil/water critical aggregation concentration of approximately 2.8 wt %. After mixing, this combination of materials is allowed to settle overnight. No visible residue is formed and all of the mixture is withdrawn and used as the oil phase in a continuous process for forming a HIPE emulsion.

Separate streams of the oil phase (25° C.) and water phase (75°–77° C.) are fed to a dynamic mixing apparatus. Thorough mixing of the combined streams in the dynamic mixing apparatus is achieved by means of a pin impeller. The pin impeller comprises a cylindrical shaft of about 21.6 cm in length with a diameter of about 1.9 cm. The shaft holds 6 rows of pins, one level with 3 rows having 21 pins and another level with 3 rows having 21 pins, each of the three pins at each level disposed at an angle of 120° to each other, with the next level down disposed at 60° to its neighboring level with each level separated by 0.03 mm, each having a diameter of 0.5 cm extending outwardly from the central axis of the shaft to a length of 1.4 cm. The pin impeller is mounted in a cylindrical sleeve which forms the dynamic mixing apparatus, and the pins have a clearance of 3 mm from the walls of the cylindrical sleeve.

A minor portion of the effluent exiting the dynamic mixing apparatus is withdrawn and enters a recirculation zone, as shown in the Figure in co-pending U.S. patent application Ser. No. 08/716,510 (T. A. DesMarais), filed Sep. 17, 1996 (herein incorporated by reference). The Waukesha pump in the recirculation zone returns the minor portion to the entry point of the oil and water phase flow streams to the dynamic mixing zone.

A spiral static mixer is mounted downstream from the dynamic mixing apparatus to provide back pressure in the dynamic mixing apparatus and to provide improved incorporation of components into the HIPE that is eventually formed. The static mixer (TAH Industries Model 070-821), modified by cutting off 2.4 inches (6.1 cm) of its original length) is 14 inches (35.6 cm) long with a 0.5 inch (1.3 cm) outside diameter.

The combined mixing and recirculation apparatus set-up is filled with oil phase and water phase at a ratio of 4 parts water to 1 part oil. The dynamic mixing apparatus is vented to allow air to escape while filling the apparatus completely. The flow rates during filling are 1.89 g/sec oil phase and 7.56 cm$^3$/sec water phase.

Once the apparatus set-up is filled, agitation is begun in the dynamic mixer, with the impeller turning at 1000 RPM and recirculation is begun at a rate of about 8 cm$^3$/sec. The flow rate of the water phase is then steadily increased to a rate of 45.4 cm$^3$/sec over a time period of about 1 min., and the oil phase flow rate is reduced to 0.6 g/sec over a time period of about 3 min. The recirculation rate is steadily increased to about 45 cm$^3$/sec during the latter time period. The back pressure created by the dynamic zone and static mixers at this point is about 2.9 PSI (20 kPa), which represents the total pressure drop of the system.

The HIPE flowing from the static mixer at this point is collected in a round polypropylene tub, 17 in. (43 cm) in diameter and 7.5 in (10 cm) high, with a concentric insert made of Celcon plastic. The insert is 5 in (12.7 cm) in diameter at its base and 4.75 in (12 cm) in diameter at its top and is 6.75 in (17.1 cm) high. The HIPE-containing tubs are kept in a room maintained at 65° C. for 18 hours to bring about polymerization and form the foam.

The cured HIPE foam is removed from the curing tubs. The foam at this point has residual water phase (containing dissolved emulsifiers, electrolyte, initiator residues, and initiator) about 70–80 times (70–80×) the weight of polymerized monomers. The foam is sliced with a sharp reciprocating saw blade into sheets which are 0.185 inches (4.7 mm) in thickness. These sheets are then subjected to compression in a series of 2 porous nip rolls equipped with vacuum which gradually reduce the residual water phase content of the foam to about 3 times (3×) the weight of the polymerized material. At this point, the sheets are then resaturated with a 1.5% $CaCl_2$ solution at 60° C., are squeezed in a series of 3 porous nip rolls equipped with vacuum to a water phase content of about 2×. The $CaCl_2$ content of the foam is between 3 and 5%.

The foam remains compressed after the final nip at a thickness of about 0.031 in. (0.079 cm). The foam is then dried in air for about 16 hours. Such drying reduces the moisture content to about 9–17% by weight of polymerized material. At this point, the foam sheets are very drapeable.

High Capillary Suction Storage Member (Samples S . . . )

Sample S.1

Storage Absorbent Member Comprising Glass Microfibers

This example describes a high capillary suction absorbent member comprising hydrogel-forming absorbent polymer and high surface area glass micro fibers as formed using a wet end forming process for increased density and structural organization over conventional air deposition processes. In order to construct such a hydrogel-forming absorbent polymer containing member which approaches a homogeneous distribution of absorbent polymer in the glass micro fiber matrix, the following procedure is followed.

A mixture of 4.0 gms of ASAP 2300 (available from Chemdal LTD, a subsidiary of American Colloid Co., Arlington Heights, Ill.; also available from The Procter & Gamble Co., Paper Technology Division, Cincinnati, Ohio) and 4.0 gms of glass micro fiber (available as "Q-FIBERS, Code 108, 110 Bulk" from Manville Sales Corp., Denver, Colo.) are combined in an explosion resistant 3-gallon Commercial grade Warner blender with approximately 500 ml of 3A alcohol (95% ethanol, 5% methanol), or Isopropanol, or similar liquids which will not degrade nor absorb into the structure or composition of the involved polymers. The mixture is stirred on low speed for approximately 5 min. The mixture is poured into a 6 in.×6 in. "Paper Formation Box" with an 80 mesh Nylon Forming Wire (available from Appleton Mfg. Div., Productive Solutions, Inc., Neenah, Wis.) at the bottom of the upper portion of the Formation Box. Liquid level is brought to about 8 in (about 20.3 cm) above the screen with addition of 3A alcohol, or appropriate solution. A paddle is used to mix the solution thoroughly in the top of the Formation box before liquid evacuation. A valve is opened below the forming wire and liquid is drained rapidly to ensure a uniform deposition on the forming wire. The screen is removed from the "Formation box", pulled across a vacuum source for removal of loosely held liquid, and allowed to air dry overnight in a desiccator containing a desiccant (such as DRIERITE, Sigme Chem. Co., St. Louis, Mo. 63178) to ensure uniform moisture content. Once dry, the absorbent member is removed from the forming screen. A 5.4 cm cylindrical-shaped structure is arch-punched from the member for measurement of capillary sorption absorbent capacity.

Sample S.2

Preparation of High Surface Area Foam from a HIPE

Anhydrous calcium chloride (36.32 kg) and potassium persulfate (189 g) are dissolved in 378 liters of water. This provides the water phase stream to be used in a continuous process for forming a HIPE emulsion.

To a monomer combination comprising distilled divinylbenzene (42.4% divinylbenzene and 57.6% ethyl styrene) (2640 g), 2-ethylhexyl acrylate (4400 g), and hexanedioldiacrylate (960 g) is added a diglycerol monooleate emulsifier (480 g), ditallow dimethyl ammonium methyl sulfate (80 g), and Tinuvin 765 (20 g). The diglycerol monooleate emulsifier (Grindsted Products; Brabrand, Denmark) comprises approximately 81% diglycerol monooleate, 1% other diglycerol monoesters, 3% polyols, and 15% other polyglycerol esters, imparts a minimum oil/water interfacial tension value of approximately 2.7 dyne/cm and has an oil/water critical aggregation concentration of approximately 2.8 wt %. After mixing, this combination of materials is allowed to settle overnight. No visible residue is formed and all of the mixture is withdrawn and used as the oil phase in a continuous process for forming a HIPE emulsion.

Separate streams of the oil phase (25° C.) and water phase (53°–55° C.) are fed to a dynamic mixing apparatus. Thorough mixing of the combined streams in the dynamic mixing apparatus is achieved by means of a pin impeller. The pin impeller comprises a cylindrical shaft of about 36.5 cm in length with a diameter of about 2.9 cm. The shaft holds 6 rows of pins, 3 rows having 33 pins and 3 rows having 34 pins, each of the three pins at each level disposed at an angle of 120° to each other, with the next level down disposed at 60° to its neighboring level with each level separated by 0.03 mm, each having a diameter of 0.5 cm extending outwardly from the central axis of the shaft to a length of 2.3 cm. The pin impeller is mounted in a cylindrical sleeve which forms the dynamic mixing apparatus, and the pins have a clearance of 1.5 mm from the walls of the cylindrical sleeve.

A minor portion of the effluent exiting the dynamic mixing apparatus is withdrawn and enters a recirculation zone, as shown in the Figure of co-pending U.S. patent application Ser. No. 08/716,510, filed Sep. 17, 1996 by DesMarais, the disclosure of which is incorporated by reference herein. The Waukesha pump in the recirculation zone returns the minor portion to the entry point of the oil and water phase flow streams to the dynamic mixing zone.

The static mixer (TAH Industries Model 100-812) has 12 elements with a 1 in. (2.5 cm) outside diameter. A hose is mounted downstream from the static mixer to facilitate delivery of the emulsion to the device used for curing. Optionally an additional static mixer is used to provide addition back pressure to keep the hose filled. The optional static mixer can be a 1 in. (2.5 cm) pipe, 12 element mixer (McMaster-Carr, Aurora, Ohio, Model 3529K53).

The combined mixing and recirculation apparatus set-up is filled with oil phase and water phase at a ratio of 4 parts water to 1 part oil. The dynamic mixing apparatus is vented to allow air to escape while filling the apparatus completely. The flow rates during filling are 7.57 g/sec oil phase and 30.3 $cm^3$/sec water phase.

Once the apparatus set-up is filled, agitation is begun in the dynamic mixer, with the impeller turning at 1750 RPM and recirculation is begun at a rate of about 30 $cm^3$/sec. The flow rate of the water phase is then steadily increased to a rate of 151.3 $cm^3$/sec over a time period of about 1 min., and the oil phase flow rate is reduced to 3.03 g/sec over a time period of about 3 min. The recirculation rate is steadily increased to about 150 $cm^3$/sec during the latter time period. The back pressure created by the dynamic zone and static mixers at this point is about 19.9 PSI (137 kPa), which represents the total pressure drop of the system. The Waukesha pump (Model 30) speed is then steadily decreased to a yield a recirculation rate of about 75 cm³/sec.

The HIPE flowing from the static mixer at this point is collected in a round polyethylene tub, 40 in. (102 cm) in diameter and 12.5 in. (31.8 cm) high, with removable sides, much like a springform pan used in cooking cakes. A pipe-like polyethylene insert 12.5 in. (31.8 cm) in diameter at its base is firmly affixed to the center of the base and is 12.5 in. (31.8 cm) high. The HIPE-containing tubs are kept in a room maintained at 65° C. for 18 hours to effect polymerization and form the foam.

The cured HIPE foam is removed from the curing tubs. The foam at this point has residual water phase (containing dissolved emulsifiers, electrolyte, initiator residues, and initiator) about 48–52 times (48–52×) the weight of polymerized monomers. The foam is sliced with a sharp reciprocating saw blade into sheets which are 0.185 inches (4.7 mm) in thickness. These sheets are then subjected to compression in a series of 2 porous nip rolls equipped with vacuum which gradually reduce the residual water phase content of the foam to about 6 times (6×) the weight of the polymerized material. At this point, the sheets are then resaturated with a 1.5% $CaCl_2$ solution at 60° C., are squeezed in a series of 3 porous nip rolls equipped with vacuum to a water phase content of about 4×. The $CaCl_2$ content of the foam is between 8 and 10%.

The foam remains compressed after the final nip at a thickness of about 0.021 in. (0.053 cm). The foam is then dried in air for about 16 hours. Such drying reduces the moisture content to about 9–17% by weight of polymerized material. At this point, the foam sheets are very drapeable and "thin-after-drying".

Sample S.3

Preparation of High Surface Area Foam from a HIPE

The water and oil phase streams to be used in a continuous process for forming a HIPE emulsion is prepared according to Sample S.2. Separate streams of the oil phase (25° C.) and water phase (53°–55° C.) are fed to a dynamic mixing apparatus as detailed in Sample S.2.

Once the apparatus set-up is filled, agitation is begun in the dynamic mixer, with the impeller turning at 1700 RPM and recirculation is begun at a rate of about 30 cm³/sec. The flow rate of the water phase is then steadily increased to a rate of 151.3 cm³/sec over a time period of about 1 min., and the oil phase flow rate is reduced to 3.36 g/sec over a time period of about 3 min. The recirculation rate is steadily increased to about 150 cm³/sec during the latter time period. The back pressure created by the dynamic zone and static mixers at this point is about 19.7 PSI (136 kPa), which represents the total pressure drop of the system. The Waukesha pump speed is then steadily decreased to a yield a recirculation rate of about 75 cm³/sec.

The HIPE flowing from the static mixer at this point is collected and cured into a polymeric foam as detailed in Sample S.2.

The cured HIPE foam is removed from the curing tubs. The foam at this point has residual water phase (containing dissolved emulsifiers, electrolyte, initiator residues, and initiator) about 43–47 times (43–47×) the weight of polymerized monomers. The foam is sliced with a sharp reciprocating saw blade into sheets which are 0.185 inches (4.7 mm) in thickness. These sheets are then subjected to compression in a series of 2 porous nip rolls equipped with vacuum which gradually reduce the residual water phase content of the foam to about 6 times (6×) the weight of the polymerized material. At this point, the sheets are then resaturated with a 1.5% $CaCl_2$ solution at 60° C., are squeezed in a series of 3 porous nip rolls equipped with vacuum to a water phase content of about 4×. The $CaCl_2$ content of the foam is between 8 and 10%.

The foam remains compressed after the final nip at a thickness of about 0.028 in. (0.071 cm). The foam is then dried in air for about 16 hours. Such drying reduces the moisture content to about 9–17% by weight of polymerized material. At this point, the foam sheets are very drapeable and "thin-after-drying".

Sample S.4

Preparation of High Surface Area Foam from a HIPE

The water and oil phase streams to be used in a continuous process for forming a HIPE emulsion is prepared according to Sample S.2. Separate streams of the oil phase (25° C.) and water phase (53°–55° C.) are fed to a dynamic mixing apparatus as detailed in Sample S.2.

Once the apparatus set-up is filled, agitation is begun in the dynamic mixer, with the impeller turning at 1750 RPM and recirculation is begun at a rate of about 30 cm³/sec. The flow rate of the water phase is then steadily increased to a rate of 151.3 cm³/sec over a time period of about 1 min., and the oil phase flow rate is reduced to 3.78 g/sec over a time period of about 3 min. The recirculation rate is steadily increased to about 150 cm³/sec during the latter time period. The back pressure created by the dynamic zone and static mixers at this point is about 18.7 PSI (129 kPa), which represents the total pressure drop of the system. The Waukesha pump speed is then steadily decreased to a yield a recirculation rate of about 75 cm³/sec.

The HIPE flowing from the static mixer at this point is collected and cured into a polymeric foam as detailed in Sample S.2.

The cured HIPE foam is removed from the curing tubs. The foam at this point has residual water phase (containing dissolved emulsifiers, electrolyte, initiator residues, and initiator) about 38–42 times (38–42×) the weight of polymerized monomers. The foam is sliced with a sharp reciprocating saw blade into sheets which are 0.185 inches (4.7 mm) in thickness. These sheets are then subjected to compression in a series of 2 porous nip rolls equipped with vacuum which gradually reduce the residual water phase content of the foam to about 6 times (6×) the weight of the polymerized material. At this point, the sheets are then resaturated with a 1.5% $CaCl_2$ solution at 60° C., are squeezed in a series of 3 porous nip rolls equipped with vacuum to a water phase content of about 4×. The $CaCl_2$ content of the foam is between 8 and 10%.

The foam remains compressed after the final nip at a thickness of about 0.028 in. (0.071 cm). The foam is then dried in air for about 16 hours. Such drying reduces the moisture content to about 9–17% by weight of polymerized material. At this point, the foam sheets are very drapeable and "thin-after-drying".

Sample S.5

Storage Absorbent Member Comprising High Surface Area Polymeric Foam Material

This example describes a high capillary suction absorbent member comprising hydrogel-forming absorbent polymer and the high suction polymeric foam material prepared according to Sample S.3. In order to construct a hydrogel-forming absorbent polymer containing member which approaches a relatively homogeneous distribution of absorbent polymer and polymeric foam, the following procedure is followed.

10 g of air dried polymeric foam (prepared according to Sample S.3 above) is placed in a blender (Osterizer model 848-36L) equipped with a 1.25 liter jar, into which 1 liter of 2% calcium chloride solution has been placed. After ensuring that all of the foam material is submerged, the blender is agitated on the 'Liquify' (high setting) for 10 seconds and then additionally agitated on the 'Grate' setting for 5 sec. The resultant slurry is then transferred to a Buchner funnel (Coors USA model 60283) lined with a paper towel. Approximately 500 ml of fluid is freely drained from the sample. The sample is then covered with a rubber membrane and vacuum is applied (approximately 500 mm Hg or about 66 kPa) to dewater the sample to a weight of 50 to 60 grams.

The sample is returned to a dry blender jar and dispersed with the agitation set on 'Liquify' while the jar and base are inverted and returned to upright several times to disperse the sample to approximately individual particles. The dispersed sample is then air dried under ambient conditions and then the foam particles are combined with hydrogel-forming absorbent polymer (ASAP 2300, available from Chemdal Corporation of Palatine, Ill. also available from The Procter & Gamble Co., Paper Technology Division, Cincinnati, Ohio), to provide a storage absorbent member consisting of a homogeneous blend of 50%, by weight, hydrogel forming polymer and 50%, by weight, high surface area polymeric foam.

Sample S.6

Storage Absorbent Member Comprising High Surface Area Fibrets

This example describes a high capillary suction absorbent member comprising hydrogel-forming absorbent polymer and high surface area fibrets. High surface area fibrets, available from Hoechst Celanese Corp. (Charlotte, N.C.) as cellulose acetate Fibrets®, are combined with hydrogel-forming absorbent polymer (ASAP 2300, available from Chemdal Corporation of Palatine, Ill.; also available from The Procter & Gamble Co., Paper Technology Division, Cincinnati, Ohio), to provide a storage absorbent member consisting of a homogeneous blend of 50%, by weight, hydrogel-forming polymer and 50%, by weight, fibrets.

Structures

As has been laid out in the general part of the description, the absorbent cores can be constructed in a wide variety of possibilities, provided these cores include an acquisition/distribution region, which is in liquid communication with an liquid storage region, and provided, that the materials used in these regions satisfy the respective requirements. Thus, such cores can be constructed from respective materials in a layered arrangement, with the basis weights and sizes adjusted to the requirements of the intended use as laid out in the above.

A specific core construction, which is useful for baby diapers of the commonly designated MAXI size, has a rectangular shape with about 450 mm length and about 100 mm width. Therein, the acquisition/distribution region cosnsits of a layer of material having a dimension of also rectangular shape, which covers the complete absorbent core. The liquid storage region can also be of rectangular shape, also extending over the complete size of the absorbent core, underlying as a layer the acquisition distribution region. The thickness of the materials can vary throughout the length and/or the width of the absorbent core, but in simple constructions it is a uniform thickness throughout the absorbent core.

It is essential for the functioning that the acquisition/distribution material and the storage materials are chosen according to their capillary suction properties as laid out in the above.

With the specially selected samples as described in the above all respective distribution material samples can be combined with any of the respective storage materials and provide a suitable performance.

Test Procedures

Unless specified otherwise, the tests are carried out under controlled laboratory conditions of about 23+/−2° C. and at 50+/−10% relative humidity. Test specimen are stored under these conditions for at least 24 hours before testing.

Synthetic Urine Formulation

Unless specified explicitly, the specific synthetic urine used in the test methods is commonly known as Jayco SynUrine and is available from Jayco Pharmaceuticals Company of Camp Hill, Pa. The formula for the synthetic urine is: 2.0 g/: of KCl; 2.0 g/l of Na2SO4; 0.85 g/l of (NH4)H2PO4; 0.15 g/l (NH4)H2PO4; 0.19 g/l of CaCl2; ad 0.23 g/l of MgCl2. All of the chemicals are of reagent grade. The pH of the synthetic Urine is in the range of 6.0 to 6.4.

Vertical Wicking Time and Vertical Wicking Capacity

Vertical wicking time is determined by measuring the time taken for a colored test liquid (e.g., synthetic urine) in a reservoir to wick a vertical distance of 15 cm through a test strip of foam of specified size. The vertical wicking procedure is detailed in the Test Methods section of U.S. Pat. No. 5,387,207 (which is incorporated by reference,) supra, but is performed at 31° C. instead of 37° C. A material's vertical wicking capacity for a given height is measured using the Vertical Wicking Absorbent Capacity Test also described in the Test Methods section of U.S. Pat. No. 5,387,207, except the test is performed at 31° C. instead of 37° C. Finally, the washing and redrying step in the referenced patent is not performed. The vertical wicking capacity value of note is taken as the capacity achieved at a height of 15 cm at equilibrium. The result is expressed in units of (g/cm$^2$/sec), at a height of 15 cm.

Simplified Liquid Permeability Test

This Simplified Permeability Test provides a measure for permeability for two special conditions: Either the permeability can be measured for a wide range of porous materials (such as non-wovens made of synthetic fibres, or cellulosic structures) at 100% saturation, or for materials, which reach different degrees of saturation with a proportional change in caliper without being filled with air (respectively the outside vapour phase), such as the collapsible polymeric foams, for which the permeability at varying degrees of saturation can readily be measured at various thicknesses.

In particular for polymeric foam materials, it has been found useful to operate the test at an elevated temperature of 31° C., so as to better simulate in-use conditions for absorbent articles.

In principle, this tests is based on Darcy's law, according to which the volumetric flow rate of a liquid through any porous medium is proportional to the pressure gradient, with the proportionality constant related to permeability.

$$Q/A = (k/\eta)*(\Delta P/L)$$

where:

Q=Volumetric Flow Rate [cm³/s];

A=Cross Sectional Area [cm²];

k=Permeability (cm²) (with 1 Darcy corresponding to 9.869* 10⁻¹³ m²);

η=Viscosity (Poise) [Pa*s];

ΔP/L=Pressure Gradient [Pa/m];

L=caliper of sample [cm].

Hence, permeability can be calculated—for a fixed or given sample cross-sectional area and test liquid viscosity—by measurement of pressure drop and the volumetric flow rate through the sample:

$$k=(Q/A)*(L/\Delta P)*\eta$$

The test can be executed in two modifications, the first referring to the transplanar permeability (i.e. the direction of flow is essentially along the thickness dimension of the material), the second being the in-plane permeability m(i.e. the direction of flow being in the x-y-direction of the material).

The test set-up for the simplified, transplanar permeability test can be see in FIG. 1 which is a schematic diagram of the overall equipment and—as an insert diagram—a partly exploded cross-sectional, not to scale view of the sample cell.

The test set-up comprises a generally circular or cylindrical sample cell (120), having an upper (121) and lower (122) part. The distance of these parts can be measured and hence adjusted by means of each three circumferentially arranged caliper gauges (145) and adjustment screws (140). Further, the equipment comprises several fluid reservoirs (150, 154, 156) including a height adjustment (170) for the inlet reservoir (150) as well as tubings (180), quick release fittings (189) for connecting the sample cell with the rest of the equipment, further valves (182, 184, 186, 188). The differential pressure transducer (197) is connected via tubing (180) to the upper pressure detection point (194) and to the lower pressure detection point (196). A Computer device (190) for control of valves is further connected via connections (199) to differential pressure transducer (197), temperature probe (192), and weight scale load cell (198).

The circular sample (110) having a diameter of 1 in (about 2.54 cm) is placed in between two porous screens (135) inside the sample cell (120), which is made of two 1 in (2.54 cm) inner diameter cylindrical pieces (121, 122) attached via the inlet connection (132) to the inlet reservoir (150) and via the outlet connection (133) to the outlet reservoir (154) by flexible tubing (180), such as tygon tubing. Closed cell foam gaskets (115) provide leakage protection around the sides of the sample. The test sample (110) is compressed to the caliper corresponding to the desired wet compression, which is set to 0.2 psi (about 1.4 kPa) unless otherwise mentioned. Liquid is allowed to flow through the sample (110) to achieve steady state flow. Once steady state flow through the sample (110) has been established, volumetric flow rate and pressure drop are recorded as a function of time using a load cell (198) and the differential pressure transducer (197). The experiment can be performed at any pressure head up to 80 cm water (about 7.8 kPa), which can be adjusted by the height adjusting device (170). From these measurements, the flow rate at different pressures for the sample can be determined.

The equipment is commercially available as a Permeameter such as supplied by Porous Materials, Inc, Ithaca, N.Y., US under the designation PMI Liquid Permeameter, such as further described in respective user manual of 2/97. This equipment includes two Stainless Steel Frits as porous screens (135), also specified in said brochure. The equipment consists of the sample cell (120), inlet reservoir (150), outlet reservoir (154), and waste reservoir (156) and respective filling and emptying valves and connections, an electronic scale, and a computerized monitoring and valve control unit (190).

The gasket material (115) is a Closed Cell Neoprene Sponge SNC-1 (Soft), such as supplied by Netherland Rubber Company, Cincinnati, Ohio, US. A set of materials with varying thickness in steps of ¹⁄₁₆" (about 0.159 cm) should be available to cover the range from ¹⁄₁₆"–½" (about 0.159 cm to about 1.27 cm) thickness.

Further a pressurized air supply is required, of at least 60 psi (4.1 bar), to operate the respective valves. Test fluid is deionized water. The test is then executed by the following steps:

1) Preparation of the test sample(s):

In a preparatory test, it is determined, if one or more layers of the test sample are required, wherein the test as outlined below is run at the lowest and highest pressure. The number of layers is then adjusted so as to maintain the flow rate during the test between 0.5 cm³'seconds at the lowest pressure drop and 15 cm³/second at the highest pressure drop. The flow rate for the sample should be less than the flow rate for the blank at the same pressure drop. If the sample flow rate exceeds that of the blank for a given pressure drop, more layers should be added to decrease the flow rate.

Sample size: Samples are cut to 1" (about 2.54 cm) diameter, by using an arch punch, such as supplied by McMaster-Carr Supply Company, Cleveland, Ohio, US. If samples have too little internal strength or integrity to maintain their structure during the required manipulation, a conventional low basis weight support means can be added, such as a PET scrim or net.

Thus, at least two samples (made of the required number of layers each, if necessary) are precut. Then, one of these is saturated in deionized water at the temperature the experiment is to be performed (70° F., (31° C.) unless otherwise noted).

The caliper of the wet sample is measured (if necessary after a stabilization time of 30 seconds) under the desired compression pressure for which the experiment will be run by using a conventional caliper gauge (such as supplied by AMES, Waltham, Mass., US) having a pressure foot diameter of 1⅛" (about 2.86 cm), exerting a pressure of 0.2 psi (about 1.4 kPa) on the sample (110), unless otherwise desired.

An appropriate combination of gasket materials is chosen, such that the total thickness of the gasketing foam (115) is between 150 and 200% of the thickness of the wet sample (note that a combination of varying thicknesses of gasket material may be needed to achieve the overall desired thickness). The gasket material (115) is cut to a circular size of 3" in diameter, and a 1 inch (2.54 cm) hole is cut into the center by using the arch punch.

In case, that the sample dimensions change upon wetting, the sample should be cut such that the required diameter is taken in the wet stage. This can also be assessed in this preparatory test, with monitoring of the respective dimensions. If these change such that either a gap is formed, or the sample forms wrinkles which would prevent it from smoothly contacting the porous screens or frits, the cut diameter should be adjusted accordingly.

The test sample (110) is placed inside the hole in the gasket foam (115), and the composite is placed on top of the bottom half of the sample cell, ensuring that the sample is in flat, smooth contact with the screen (135), and no gaps are formed at the sides.

The top of the test cell (121) is laid flat on the lab bench (or another horizontal plane) and all three caliper gauges (145) mounted thereon are zeroed.

The top of the test cell (121) is then placed onto the bottom part (122) such that the gasket material (115) with the test sample (110) lays in between the two parts. The top and bottom part are then tightened by the fixation screws (140), such that the three caliper gauges are adjusted to the same value as measured for the wet sample under the respective pressure in the above.

2) To prepare the experiment, the program on the computerized unit (190) is started and sample identification, respective pressure etc. are entered.
3) The test will be run on one sample (110) for several pressure cycles, with the first pressure being the lowest pressure. The results of the individual pressure runs are put on different result files by the computerized unit (190). Data are taken from each of these files for the calculations as described below. (A different sample should be used for any subsequent runs of the material.)
4) The inlet liquid reservoir (150) is set to the required height and the test is started on the computerized unit (190).
5) Then, the sample cell (120) is positioned into the permeameter unit with Quick Disconnect fittings (189).
6) The sample cell (120) is filled by opening the vent valve (188) and the bottom fill valves (184, 186). During this step, care must be taken to remove air bubbles from the system, which can be achieved by turning the sample cell vertically, forcing air bubbles—if present—to exit the permeameter through the drain.

Once the sample cell is filled up to the tygon tubing attached to the top of the chamber (121), air bubbles are removed from this tubing into the waste reservoir (156).
7) After having carefully removed air bubbles, the bottom fill valves (184, 186) are closed, and the top fill (182) valve is opened, so as to fill the upper part, also carefully removing all air bubbles.
8) The fluid reservoir is filled with test fluid to the fill line (152).

Then the flow is started through the sample by initiating the computerized unit (190).

After the temperature in the sample chamber has reached the required value, the experiment is ready to begin.

Upon starting the experiment via the computerized unit (190), the liquid outlet flow is automatically diverted from the waste reservoir (156) to the outlet reservoir (154), and pressure drop, and temperature are monitored as a function of time for several minutes.

Once the program has ended, the computerized unit provides the recorded data (in numeric and/or graphical form).

If desired, the same test sample can be used to measure the permeability at varying pressure heads, with thereby increasing the pressure from run to run.

The equipment should be cleaned every two weeks, and calibrated at least once per week, especially the frits, the load cell, the thermocouple and the pressure transducer, thereby following the instructions of the equipment supplier.

The differential pressure is recorded via the differential pressue transducer connected to the pressure probes measurement points (194, 196) in the top and bottom part of the sample cell. Since there may be other flow resistances within the chamber adding to the pressure that is recorded, each experiment must be corrected by a blank run. A blank run should be done at 10, 20, 30, 40, 50, 60, 70, 80 cm requested pressure, each day. The permeameter will output a Mean Test Pressure for each experiment and also an average flow rate.

For each pressure that the sample has been tested at, the flow rate is recorded as Blank Corrected Pressure by the computerized unit (190), which is further correcting the Mean Test Pressure (Actual Pressure) at each height recorded pressure differentials to result in the Corrected Pressure. This Corrected Pressure is the DP that should be used in the permeability equation below.

Permeability can then be calculated at each requested pressure and all permeabilities should be averaged to determine the k for the material being tested.

Three measurements should be taken for each sample at each head and the results averaged and the standard deviation calculated. However, the same sample should be used, permeability measured at each head, and then a new sample should be used to do the second and third replicates.

The measuring of the in-plane permeability under the same conditions as the above described transplanar permeability, can be achieved by modifying the above equipment such as schematically depicted in FIGS. 2A and 2B showing the partly exploded, not to scale view of the sample cell only. Equivalent elements are denoted equivalently, such that the sample cell of FIG. 2 is denoted (210), correlating to the numeral (110) of FIG. 1, and so on. Thus, the transplanar simplified sample cell (120) of FIG. 1 is replaced by the in-plane simplified sample cell (220), which is designed so that liquid can flow only in one direction (either machine direction or cross direction depending on how the sample is placed in the cell). Care should be taken to minimize channeling of liquid along the walls (wall effects), since this can erroneously give high permeability reading. The test procedure is then executed quite analogous to the transplanar simplified test.

The sample cell (220) is designed to be positioned into the equipment essentially as described for the sample cell (120) in the above transplanar test, except that the filling tube is directed to the inlet connection (232) the bottom of the cell (220). FIG. 2A shows a partly exploded view of the sample cell, and FIG. 2B a cross-sectional view through the sample level.

The test cell (220) is made up of two pieces: a bottom piece (225) which is like a rectangular box with flanges, and a top piece (223) that fits inside the bottom piece (225) and has flanges as well. The test sample is cut to the size of 2" in×2" in (about 5.1 cm by 5.1 cm) and is placed into the bottom piece. The top piece (223) of the sample chamber is then placed into the bottom piece (225) and sits on the test sample (210). An incompressible neoprene rubber seal (224) is attached to the upper piece (223) to provide tight sealing. The test liquid flows from the inlet reservoir to the sample space via Tygon tubing and the inlet connection (232) further through the outlet connection (233) to the outlet reservoir. As in this test execution the temperature control of the fluid passing through the sample cell can be insufficient due to lower flow rates, the sample is kept at the desired test temperature by the heating device (226), whereby thermostated water is pumped through the heating chamber (227). The gap in the test cell is set at the caliper corresponding to the desired wet compression, normally 0.2 psi ( about 1.4 kPa). Shims (216) ranging in size from 0.1 mm to 20.0 mm are used to set the correct caliper, optionally using combinations of several shims.

At the start of the experiment, the test cell (220) is rotated 90° (sample is vertical) and the test liquid allowed to enter slowly from the bottom. This is necessary to ensure that all the air is driven out from the sample and the inlet/outlet connections (232/233). Next, the test cell (220) is rotated back to its original position so as to make the sample (210) horizontal. The subsequent procedure is the same as that described earlier for transplanar permeability, i.e. the inlet reservoir is placed at the desired height, the flow is allowed to equilibrate, and flow rate and pressure drop are measured. Permeability is calculated using Darcy's law. This procedure is repeated for higher pressures as well.

For samples that have very low permeability, it may be necessary to increase the driving pressure, such as by extending the height or by applying additional air pressure on the reservoir in order to get a measurable flow rate. In plane permeability can be measured independently in the machine and cross directions, depending on how the sample is placed in the test cell.

General Liquid Permeability Test

The generalized permeability test can measure permeability as a function of saturation for any porous material. The principle of the tests is similar to the one for the Simplified Test, with the essential difference being that the sample is loaded with a defined amount of air in addition to the liquid loading, resulting in a fixed degree of saturation. This is achieved by the test arrangement as schematically depicted in FIG. 3 showing the principles as well as the specifics for the General Transplanar Permeability, and in FIG. 4, showing the differences for the General In-plane Permeability. Unreferenced numerals correspond to the respective numerals of FIG. 1 (e.g., waste reservoir (356) corresponds to waste reservoir (156) etc.).

Therein, also the sample cell (320/420) is mounted with fixation (341, not shown in FIG. 4) on a height adjustment device (372), in addition to the inlet reservoir (350) being height adjustable by a means (370). This inlet reservoir defines a first height difference (357) relative to the outlet reservoir (354), which relates to the differential pressure $\Delta p$ (which denotes the pressure differential for calculating the permeability). This inlet reservoir (350) defines a second height difference (359) relative to the sample height which relates to the differential pressure $\Delta p(c)$, which denotes the pressure differential linked to the saturation in the sample, whereby higher capillary suction typically correlates to lower saturation.

The experiment is started at low $\Delta Pc$ (close to zero cm of water) at which the sample will be at 100% saturation. Liquid flows through the sample due to the applied pressure drop $\Delta p(c)$ (inlet reservoir height—outlet reservoir height). At steady state, the uptake of liquid in the outlet reservoir is measured as a function of time. Permeability can be calculated from the pressure drop and the volumetric flow rate data using Darcy's law. The exact degree of saturation can be obtained from the weight of the wet sample after the test compared to the dry sample before the test.

In order to measure the permeability at saturation below 100%, a new test sample is first brought to 100% saturation as described in the paragraph above. Next, the sample is moved to a higher height (10 cm for example) and is allowed to equilibrate at that height. During this time, liquid continuously flows from the inlet to the outlet reservoir. The saturation in the sample will decrease with time. When steady state is reached, i.e. when the uptake versus time plot is linear, the flow rate, pressure drop and saturation are measured as described above. This procedure is repeated for several sample heights using new samples.

It may be necessary to increase the pressure drop between the inlet and outlet reservoirs as the saturation decreases in order to get a measurable flow rate. This is because, for most porous materials, permeability decreases steeply with decreasing saturation. It is necessary to ensure that the pressure drop between the inlet and outlet reservoirs is much smaller than the capillary suction.

It is necessary to use wide liquid reservoirs (352, 354) in order to ensure that the liquid level does not change significantly while waiting for steady state to be reached.

This test gives permeability versus saturation for the desorption cycle, that is the sample has higher saturation to start with. Whilst of course permeability data can be generated for the absorption cycle, these should not be used in present evaluations, as some hysteresis effects might occur.

The sample cell (320) for the general transplanar permeability test differs from sample cell (120) of the simplified transplanar permeability test essentially in that it comprises two frits (335) arranged on top and underneath the sample (310). For the frits (335) it is necessary to ensure that most of the resistance to flow is offered by the sample and the frit resistance is negligible. A fine pored, thin membrane over a coarse frit allows measurements up to high heights without offering significant resistance to flow. The frits should be selected so as to have a sufficiently high bubble point pressure corresponding to more than about 200 cm water height, but at the same time providing low flow resistance. This can well be achieved by selecting sufficiently thin membranes of the require bubble point pressure overlying a more open support structure.

For the general permeability tests, care must be taken, that the air is allowed to contact the sample via the side surfaces, so as to allow varying degrees of saturation depending on the $\Delta p(c)$. Thus, the sample cell design is essentially identical to the test cell of the simplified transplanar test, except, that the foam gasketing material is removed, and the arrangement to adjust the gap between the top and the bottom parts replaced by a constant pressure generating device, such as a weight (317) to maintain (together with the weight of the top piece (321)) the sample under the desired pressure, of 0.2 psi (about 1.4 kPa) unless otherwise desired.

For the general in-plane permeability test the sample cell (420) is shown in FIG. 4, which is a design being derived from the simplified in-plane test and the principles as described in the above. Thus, the fluid in entering the sample cell (420) via the fluid inlet (432) and outlet (433), which are connected to the membranes (435), such as frits of the type as described above (for frits 335). The test sample (410) is positioned with its ends overlaying the two frits, but not with the center part of 2 in by 2 in (about 5.1 cm by 5.1 cm) whereby wrinkles and gaps between the sample and the membranes have to be avoided. The test sample (410) is placed between the upper and lower part of the sample cell (420), with the weight (417) being used to adjust the pressure under which the experiment is run (0.2 psi (about 1.4 kPa) unless otherwise desired and denoted). Also, the sample is kept a constant temperature via the heating device (426), e.g. by pumping constant temperature water through the heating chamber (427).

Also for this set up, the possibility of air entering into the sample via the side surfaces is essential to allow the varying degrees of saturation.

Liquid Viscosity

The liquid viscosity is an important input parameter for the above determination, and should be taken for the respective fluid for the respective temperature, either from well known tables, or equations, or measured via well established measurement procedures.

Capillary Sorption

Purpose

The purpose of this test is to measure the capillary sorption absorbent capacity, as a function of height, of storage absorbent members of the present invention. (The test is also used to measure the capillary sorption absorbent capacity, as a function of height, of the high surface area materials—i.e., without osmotic absorbent, such as hydrogel-forming absorbent polymer, or other optional materials utilized in the absorbent member. Nonetheless, the discussion that follows discusses the Capillary Sorption method as it pertains to measuring an entire storage absorbent member.) Capillary sorption is a fundamental property of any absorbent that governs how liquid is absorbed into the absorbent structure. In the Capillary Sorption experiment, capillary sorption absorbent capacity is measured as a function of fluid pressure due to the height of the sample relative to the test fluid reservoir.

The method for determining capillary sorption is well recognized. See Burgeni, A. A. and Kapur, C., "Capillary Sorption Equilibria in Fiber Masses," Textile Research Journal, 37 (1967), 356–366; Chatterjee, P. K., Absorbency, Textile Science and Technology 7, Chapter II, pp 29–84, Elsevier Science Publishers B.V, 1985; and U.S. Pat. No. 4,610,678, issued Sep. 9, 1986 to Weisman et al. for a discussion of the method for measuring capillary sorption of absorbent structures. The disclosure of each of these references is incorporated by reference herein.

Principle

A porous glass frit is connected via an uninterrupted column of fluid to a fluid reservoir on a balance. The sample is maintained under a constant confining weight during the experiment. As the porous structure absorbs fluid upon demand, the weight loss in the balance fluid reservoir is recorded as fluid uptake, adjusted for uptake of the glass frit as a function of height and evaporation. The uptake or capacity at various capillary suctions (hydrostatic tensions or heights) is measured. Incremental absorption occurs due to the incremental lowering of the frit (i.e., decreasing capillary suction).

Time is also monitored during the experiment to enable calculation of initial effective uptake rate (g/g/h) at a 200 cm height.

Reagents

Test Liquid: Synthetic urine is prepared by completely dissolving the following materials in distilled water.

| Compound | F.W. | Concentration (g/L) |
| --- | --- | --- |
| KCl | 74.6 | 2.0 |
| Na$_2$SO$_4$ | 142 | 2.0 |
| (NH$_4$)H$_2$PO$_4$ | 115 | 0.85 |
| (NH$_4$)$_2$HPO$_4$ | 132 | 0.15 |
| CaCl$_2$.2H$_2$O | 147 | 0.25 |
| MgCl$_2$.6H$_2$O | 203 | 0.5 |

General Description of Apparatus Set Up

The Capillary Sorption equipment, depicted generally as 520 in FIG. 2A, used for this test is operated under TAPPI conditions (50% RH, 25° C.). A test sample is placed on a glass frit shown in FIG. 2A as 502 that is connected via a continuous column of test liquid (synthetic urine) to a balance liquid reservoir, shown as 506, containing test liquid. This reservoir 506 is placed on a balance 507 that is interfaced with a computer (not shown). The balance should be capable of reading to 0.001 g; such a balance is available from Mettler Toledo as PR1203 (Hightstown, N.J.). The glass frit 502 is placed on a vertical slide, shown generally in FIG. 2A as 501, to allow vertical movement of the test sample to expose the test sample to varying suction heights. The vertical slide may be a rodless actuator which is attached to a computer to record suction heights and corresponding times for measuring liquid uptake by the test sample. A preferred rodless actuator is available from Industrial Devices (Novato, Calif.) as item 202X4X34N-1D4B-84-P-C-S-E, which may be powered by motor drive ZETA 6104-83-135, available from CompuMotor (Rohnert, Calif.). Where data is measured and sent from actuator 501 and balance 507, capillary sorption absorbent capacity data may be readily generated for each test sample. Also, computer interface to actuator 501 may allow for controlled vertical movement of the glass frit 502. For example, the actuator may be directed to move the glass frit 502 vertically only after "equilibrium" (as defined below) is reached at each suction height.

The bottom of glass frit 502 is connected to Tygon® tubing 503 that connects the frit 505 to three-way drain stopcock 509. Drain stopcock 509 is connected to liquid reservoir 505 via glass tubing 504 and stopcock 510. (The stopcock 509 is open to the drain only during cleaning of the apparatus or air bubble removal.) Glass tubing 511 connects fluid reservoir 505 with balance fluid reservoir 506, via stopcock 510. Balance liquid reservoir 506 consists of a lightweight 12 cm diameter glass dish 506A and cover 506B. The cover 506B has a hole through which glass tubing 511 contacts the liquid in the reservoir 506. The glass tubing 511 must not contact the cover 506B or an unstable balance reading will result and the test sample measurement cannot be used.

The glass frit diameter must be sufficient to accommodate the piston/cylinder apparatus, discussed below, for holding the test sample. The glass frit 502 is jacketed to allow for a constant temperature control from a heating bath. The frit is a 350 ml fritted disc funnel specified as having 4 to 5.5 µm pores, available from Coming Glass Co. (Coming, N.Y.) as #36060-350F. The pores are fine enough to keep the frit surface wetted at capillary suction heights specified (the glass frit does not allow air to enter the continuous column of test liquid below the glass frit).

As indicated, the frit 502 is connected via tubing to fluid reservoir 505 or balance liquid reservoir 506, depending on the position of three-way stopcock 510.

Glass frit 502 is jacketed to accept water from a constant temperature bath. This will ensure that the temperature of the glass frit is kept at a constant temperature of 88° F. (31° C.) during the testing procedure. As is depicted in FIG. 2A, the glass frit 502 is equipped with an inlet port 502A and outlet port 502B, which make a closed loop with a circulating heat bath shown generally as 508. (The glass jacketing is not depicted in FIG. 2A. However, the water introduced to the jacketed glass frit 502 from bath 508 does not contact the test liquid and the test liquid is not circulated through the constant temperature bath. The water in the constant temperature bath circulates through the jacketed walls of the glass frit 502.)

Reservoir 506 and balance 507 are enclosed in a box to minimize evaporation of test liquid from the balance reservoir and to enhance balance stability during performance of the experiment. This box, shown generally as 512, has a top and walls, where the top has a hole through which tubing 511 is inserted.

The glass frit 502 is shown in more detail in FIG. 2B. FIG. 2B is a cross-sectional view of the glass frit, shown without inlet port 502A and outlet port 502B. As indicated, the glass frit is a 350 ml fritted disc funnel having specified 4 to 5.5 μm pores. Referring to FIG. 2B, the glass frit 502 comprises a cylindrical jacketed funnel designated as 550 and a glass frit disc shown as 560. The glass frit 502 further comprises a cylinder/piston assembly shown generally as 565 (which comprises cylinder 566 and piston 568), which confines the test sample, shown as 570, and provides a small confining pressure to the test sample. To prevent excessive evaporation of test liquid from the glass frit disc 560, a Teflon ring shown as 562 is placed on top of the glass frit disc 560. The Teflon® ring 562 is 0.0127 cm thick (available as sheet stock from McMasterCarr as #8569K16 and is cut to size) and is used to cover the frit disc surface outside of the cylinder 566, and thus minimizes evaporation from the glass frit. The ring outer diameter and inner diameter is 7.6 and 6.3 cm, respectively. The inner diameter of the Teflon® ring 562 is about 2 mm less than the outer diameter of cylinder 566. A Viton® O-ring (available from McMasterCarr as #AS568A-150 and AS568A-151) 564 is placed on top of Teflon® ring 562 to seal the space between the inner wall of cylindrical jacketed funnel 550 and Teflon® ring 562, to further assist in prevention of evaporation. If the O-ring outer diameter exceeds the inner diameter of cylindrical jacketed funnel 550, the O-ring diameter is reduced to fit the funnel as follows: the O-ring is cut open, the necessary amount of O-ring material is cut off, and the O-ring is glued back together such that the O-ring contacts the inner wall of the cylindrical jacketed funnel 550 all around its periphery.

As indicated, a cylinder/piston assembly shown generally in FIG. 2B as 565 confines the test sample and provides a small confining pressure to the test sample 570. Referring to FIG. 2C, assembly 565 consists of a cylinder 566, a cup-like Teflon® piston indicated by 568 and, when necessary, a weight or weights (not shown) that fits inside piston 568. (Optional weight will be used when necessary to adjust the combined weight of the piston and the optional weight so a confining pressure of 0.2 psi is attained depending on the test sample's dry diameter. This is discussed below.) The cylinder 566 is Lexan® bar stock and has the following dimensions: an outer diameter of 7.0 cm, an inner diameter of 6.0 cm and a height of 6.0 cm. The Teflon® piston 568 has the following dimensions: an outer diameter that is 0.02 cm less than the inner diameter of cylinder 566. As shown in FIG. 2D, the end of the piston 568 that does not contact the test sample is bored to provide a 5.0 cm diameter by about 1.8 cm deep chamber 590 to receive optional weights (dictated by the test sample's actual dry diameter) required to attain a test sample confining pressure of 0.2 psi (1.4 kPa). In other words, the total weight of the piston 568 and any optional weights (not shown in figures) divided by the test sample's actual diameter (when dry) should be such that a confining pressure of 0.2 psi is attained. Cylinder 566 and piston 568 (and optional weights) are equilibrated at 31° C. for at least 30 minutes prior to conducting the capillary sorption absorbent capacity measurement.

A non-surfactant treated or incorporated apertured film (14 cm×14 cm) (not shown) is used to cover the glass frit 502 during Capillary Sorption experiments to minimize air destablization around the sample. Apertures are large enough to prevent condensation from forming on the underside of the film during the experiment.

Test Sample Preparation

The test sample can be obtained by punching out a 5.4 cm diameter circular-shaped structure from a storage absorbent member. When the member is a component of an absorbent article, other components of the article must be removed prior to testing. In those situations where the member cannot be isolated from other components of the article without significantly altering its structure (e.g., density, relative disposition of the component materials, physical properties of constituent materials, etc.) or where the member is not a component of an absorbent article, the test sample is prepared by combining all the materials that constitute the member such that the combination is representative of the member in question. The test sample is a 5.4 cm diameter circle and is obtained by cutting with an arch punch.

The dry weight of the test sample (used below to calculate capillary sorption absorbent capacity) is the weight of the test sample prepared as above under ambient conditions.

Experimental Set Up

1. Place a clean, dry glass frit 502 in a funnel holder attached to the vertical slide 501. Move the funnel holder of the vertical slide such that the glass frit is at the 0 cm height.

2. Set up the apparatus components as shown in FIG. 2A, as discussed above.

3. Place 12 cm diameter balance liquid reservoir 506 on the balance 507. Place plastic lid 506B over this balance liquid reservoir 506 and a plastic lid over the balance box 512 each with small holes to allow the glass tubing 511 to fit through. Do not allow the glass tubing to touch the lid 506B of the balance liquid reservoir or an unstable balance reading will result and the measurement cannot be used.

4. Stopcock 510 is closed to tubing 504 and opened to glass tubing 511. Fluid reservoir 505, previously filled with test fluid, is opened to allow test fluid to enter tubing 511, to fill balance fluid reservoir 506.

5. The glass frit 502 is leveled and secured in place. Also, ensure that the glass frit is dry.

6. Attach the Tygon® tubing 503 to stopcock 509. (The tubing should be long enough to reach the glass frit 502 at its highest point of 200 cm with no kinks.) Fill this Tygon® tubing with test liquid from liquid reservoir 505.

7. Attach the Tygon® tubing 503 to the level glass frit 502 and then open stopcock 509 and stopcock 510 leading from fluid reservoir 505 to the glass frit 502. (Stopcock 510 should be closed to glass tubing 511.) The test liquid fills the glass frit 502 and removes all trapped air during filling of the level glass frit. Continue to fill until the fluid level exceeds the top of the glass frit disc 560.

Empty the funnel and remove all air bubbles in the tubing and inside the funnel. Air bubbles may be removed by inverting glass frit 502 and allowing air bubbles to rise and escape through the drain of stopcock 509. (Air bubbles typically collect on the bottom of the glass frit disc 560.) Relevel the frit using a small enough level that it will fit inside the jacketed funnel 550 and onto the surface of glass frit disc 560.

8. Zero the glass frit with the balance liquid reservoir 506. To do this, take a piece of Tygon® tubing of sufficient length and fill it with the test liquid. Place one end in the balance liquid reservoir 506 and use the other end to position the glass frit 502. The test liquid level indicated by the tubing (which is equivalent to the balance liquid reservoir level) is 10 mm below the top of the glass frit disc 560. If this is not the case, either adjust the amount of liquid in the reservoir or reset the zero position on the vertical slide 501.

9. Attach the outlet and inlet ports from the temperature bath 508 via tubing to the inlet and outlet ports 502A and 502B, respectively, of the glass frit. Allow the temperature of the glass frit disc 560 to come to 31° C. This can be measured by partially filling the glass frit with test liquid and measuring its temperature after it has reached equilibrium temperature. The bath will need to be set a bit higher than 31° C. to allow for the dissipation of heat during the travel of water from the bath to the glass frit.

10. The glass frit is equilibrated for 30 minutes.

Capillary Sorption Parameters

The following describes a computer program that will determine how long the glass frit remains at each height.

In the capillary sorption software program, a test sample is at some specified height from the reservoir of fluid. As indicated above, the fluid reservoir is on a balance, such that a computer can read the balance at the end of a known time interval and calculate the flow rate (Delta reading/time interval) between the test sample and reservoir. For purposes of this method, the test sample is considered to be at equilibrium when the flow rate is less than a specified flow rate for a specified number of consecutive time intervals. It is recognized, that for certain material, actual equilibrium may not be reached when the specified "EQUILIBRIUM CONSTANT" is reached. The time interval between readings is 5 seconds.

The number of readings in the delta table is specified in the capillary sorption menu as "EQUILIBRIUM SAMPLES". The maximum number of deltas is 500. The flow rate constant is specified in the capillary sorption menu as "EQUILIBRIUM CONSTANT".

The Equilibrium Constant is entered in units of grams/sec, ranging from 0.0001 to 100.000.

The following is a simplified example of the logic. The table shows the balance reading and Delta Flow calculated for each Time Interval.

Equilibrium Samples=3

Equilibrium Constant=0.0015

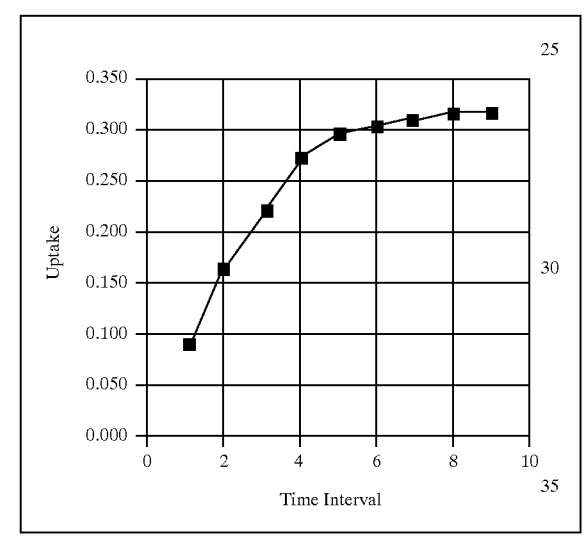

| Time Interval | Balance Value (g) | Delta Flow (g/sec) |
|---|---|---|
| 0 | 0 | |
| 1 | 0.090 | 0.0180 |
| 2 | 0.165 | 0.0150 |
| 3 | 0.225 | 0.0120 |
| 4 | 0.270 | 0.0090 |
| 5 | 0.295 | 0.0050 |
| 6 | 0.305 | 0.0020 |
| 7 | 0.312 | 0.0014 |
| 8 | 0.316 | 0.0008 |
| 9 | 0.318 | 0.0004 |

| | Delta Table: | | | | | | | | | |
|---|---|---|---|---|---|---|---|---|---|---|
| Time | 0 | 1 | 2 | 3 | 4 | 5 | 6 | 7 | 8 | 9 |
| Delta1 | 9999 | 0.0180 | 0.0180 | 0.0180 | 0.0090 | 0.0090 | 0.0090 | 0.0014 | 0.0014 | 0.0014 |
| Delta2 | 9999 | 9999 | 0.0150 | 0.0150 | 0.0150 | 0.0050 | 0.0050 | 0.0050 | 0.0008 | 0.0008 |
| Delta3 | 9999 | 9999 | 9999 | 0.0120 | 0.0120 | 0.0120 | 0.0020 | 0.0020 | 0.0020 | 0.0004 |

The equilibrium uptake for the above simplified example is 0.318 gram.

The following is the code in C language used to determine equilibrium uptake:

```
/*                    takedata.c                                    */
int take_data(int equil_samples,double equilibrium_constant)
{
double     delta;
static     double deltas[500];   /* table to store up to 500 deltas */
double     value;
double     prev_value;
clock_t    next_time;
int        i;
for (i=0; i<equil_samples; i++)
   deltas[i] = 9999.;                /* initialize all values in the delta table to 9999. gms/sec */
delta_table_index = 0;               /* initialize where in the table to store the next delta */
equilibrium_reached = 0;             /* initialize flag to indicate equilibrium has not been reached */
next_time = clock( );                /* initialize when to take the next reading */
prev_reading = 0.;                   /* initialize the value of the previous reading from the balance */
while (!equilibrium_reached) {          /* start of loop for checking for equilibrium */
   next_time += 5000 L;              /* calculate when to take next reading */
   while (clock( ) < next_time);     /* wait until 5 seconds has elasped from prev reading */
   value = get_balance_reading( );   /* read the balance in grams */
   delta = fabs(prev_value - value)/5.0;  /* calculate absolute value of flow in last 5 seconds */
   prev_value = value;               /* store current value for next loop */
   deltas[delta_table_index] = delta;  /* store current delta value in the table of deltas */
   delta_table_index++;              /* increment pointer to next position in table */
   if (delta_table_index == equil_samples)  /* when the number of deltas = the number of */
       delta_table_index = 0;        /* equilibrium samples specified, /*
                                     /* reset the pointer to the start of the table. This way */
                                     /* the table always contains the last xx current samples. */
   equilibrium_reached = 1;          /* set the flag to indicate equilibrium is reached */
   for (i=0; i < equil_samples; i++) /* check all the values in the delta table */
       if (deltas[i] >= equilibrium_constant)  /* if any value is > or = to the equilibrium constant */
           equilibrium_reached = 0;  /* set the equlibrium flag to 0 (not at equilibrium) */
   }                                 /* go back to the start of the loop */
}
```

Capillary Sorption Parameters

Load Description (Confining Pressure): 0.2 psi load

Equilibrium Samples (n): 50

Equilibrium Constant: 0.0005 g/sec

Setup Height Value: 100 cm

Finish Height Value: 0 cm

Hydrostatic Head Parameters: 200, 180, 160, 140, 120, 100, 90, 80, 70, 60, 50, 45, 40, 35, 30, 25, 20, 15, 10, 5 and 0 cm.

The capillary sorption procedure is conducted using all the heights specified above, in the order stated, for the measurement of capillary sorption absorbent capacity. Even if it is desired to determine capillary sorption absorbent capacity at a particular height (e.g., 35 cm), the entire series of hydrostatic head parameters must be completed in the order specified. Although all these heights are used in performance of the capillary sorption test to generate capillary sorption isotherms for a test sample, the present disclosure describes the storage absorbent members in terms of their absorbent properties at specified heights of 200, 140, 100, 50, 35 and 0 cm.

Capillary Sorption Procedure

1) Follow the experimental setup procedure.

2) Make sure the temperature bath 508 is on and water is circulating through the glass frit 502 and that the glass frit disc 560 temperature is 31° C.

3) Position glass frit 502 at 200 cm suction height. Open stopcocks 509 and 510 to connect glass frit 502 with the balance liquid reservoir 506. (Stopcock 510 is closed to liquid reservoir 505.) Glass frit 502 is equilibrated for 30 minutes.

4) Input the above capillary sorption parameters into the computer.

5) Close stopcocks 509 and 510.

6) Move glass frit 502 to the set up height, 100 cm.
7) Place Teflon® ring 562 on surface of glass frit disc 560. Put O-ring 564 on Teflon® ring. Place pre-heated cylinder 566 concentrically on the Teflon® ring. Place test sample 570 concentrically in cylinder 566 on glass frit disc 560. Place piston 568 into cylinder 566. Additional confining weights are placed into piston chamber 590, if required.
8) Cover the glass frit 502 with apertured film.
9) The balance reading at this point establishes the zero or tare reading.
10) Move the glass frit 502 to 200 cm.
11) Open stopcocks 509 and 510 (stopcock 510 is closed to fluid reservoir 505) and begin balance and time readings.

Glass Frit Correction (Blank Correct Uptake)

Since the glass frit disc 560 is a porous structure, the glass frit (502) capillary sorption absorption uptake (blank correct uptake) must be determined and subtracted to get the true test sample capillary sorption absorption uptake. The glass frit correction is performed for each new glass frit used. Run the capillary sorption procedure as described above, except without test sample, to obtain the Blank Uptake(g). The elapsed time at each specified height equals the Blank Time(s).

Evaporation Loss Correction

1) Move the glass frit 502 to 2 cm above zero and let it equilibrate at this height for 30 minutes with open stopcocks 509 and 510 (closed to reservoir 505).
2) Close stopcocks 509 and 510.
3) Place Teflon® ring 562 on surface of glass frit disc 560. Put O-ring 564 on Teflon® ring. Place pre-heated cylinder 566 concentrically on the Teflon® ring. Place piston 568 into cylinder 566. Place apertured film on glass frit 502.
4) Open stopcocks 509 and 510 (closed to reservoir 505) and record balance reading and time for 3.5 hours. Calculate Sample Evaporation (g/hr) as follows:

[balance reading at 1 hr–balance reading at 3.5 hr]/2.5 hr

Even after taking all the above precautions, some evaporative loss will occur, typically around 0.10 gm/hr for both the test sample and the frit correction. Ideally, the sample evaporation is measured for each newly installed glass frit 502.

Cleaning the Equipment

New Tygon® tubing 503 is used when a glass frit 502 is newly installed. Glass tubing 504 and 511, fluid reservoir 505, and balance liquid reservoir 506 are cleaned with 50% Clorox Bleach® in distilled water, followed by distilled water rinse, if microbial contamination is visible.

a. Cleaning After Each Experiment

At the end of each experiment (after the test sample has been removed), the glass frit is forward flushed (i.e., test liquid is introduced into the bottom of the glass frit) with 250 ml test liquid from liquid reservoir 505 to remove residual test sample from the glass frit disc pores. With stopcocks 509 and 510 open to liquid reservoir 505 and closed to balance liquid reservoir 506, the glass frit is removed from its holder, turned upside down and is rinsed out first with test liquid, followed by rinses with acetone and test liquid (synthetic urine). During rinsing, the glass frit must be tilted upside down and rinse fluid is squirted onto the test sample contacting surface of the glass frit disc. After rinsing, the glass frit is forward flushed a second time with 250 ml test liquid (synthetic urine). Finally, the glass frit is reinstalled in its holder and the frit surface is leveled.

b. Monitoring Glass Frit Performance

Glass frit performance must be monitored after each cleaning procedure and for each newly installed glass frit, with the glass frit set up at 0 cm position. 50 ml of test liquid are poured onto the leveled glass frit disc surface (without Teflon® ring, O-ring and the cylinder/piston components). The time it takes for the test fluid level to drop to 5 mm above the glass frit disc surface is recorded. A periodic cleaning must be performed if this time exceeds 4.5 minutes.

c. Periodic Cleaning

Periodically, (see monitoring frit performance, above) the glass frits are cleaned thoroughly to prevent clogging. Rinsing fluids are distilled water, acetone, 50% Clorox Bleach® in distilled water (to remove bacterial growth) and test liquid. Cleaning involves removing the glass frit from the holder and disconnecting all tubing. The glass frit is forward flushed (i.e., rinse liquid is introduced into the bottom of the glass frit) with the frit upside down with the appropriate fluids and amounts in the following order:

1. 250 ml distilled water.
2. 100 ml acetone.
3. 250 ml distilled water.
4. 100 ml 50:50 Clorox®/distilled water solution.
5. 250 ml distilled water.
6. 250 ml test fluid.

The cleaning procedure is satisfactory when glass frit performance is within the set criteria of fluid flow (see above) and when no residue is observable on the glass frit disc surface. If cleaning can not be performed successfully, the frit must be replaced.

Calculations

The computer is set up to provide a report consisting of the capillary suction height in cm, time, and the uptake in grams at each specified height. From this data, the capillary suction absorbent capacity, which is corrected for both the frit uptake and the evaporation loss, can be calculated. Also, based on the capillary suction absorbent capacity at 0 cm, the capillary absorption efficiency can be calculated at the specified heights. In addition, the initial effective uptake rate at 200 cm is calculated.

Blank Correct Uptake $$\text{Blank Correct Uptake (g)} = \text{Blank Uptake (g)} - \frac{\text{Blank Time (s)} * \text{Sample Evap. (g/hr)}}{3600 \text{ (s/hr)}}$$

Capillary Suction Absorbent Capacity ("CSAC")

$$\text{CSAC (g/g)} = \frac{\text{Sample Uptake (g)} - \frac{\text{Sample Time (s)} * \text{Sample Evap. (g/hr)}}{3600 \text{ s/hr}} - \text{Blank Correct Uptake (g)}}{\text{Dry Weight of Sample (g)}}$$

Initial Effective Uptake Rate at 200 cm ("IEUR")

$$\text{IEUR (g/g/hr)} = \frac{\text{CSAC at 200 cm (g/g)}}{\text{Sample Time at 200 cm (s)}}$$

Reporting

A minimum of two measurements should be taken for each sample and the uptake averaged at each height to calculate Capillary Sorption Absorbent Capacity (CSAC) for a given absorbent member or a given high surface area material.

With these data, the respective values can be calculated:
The Capillary Sorption Desorption Height at which the material has released x % of its capacity at 0 cm (i.e. of CSAC 0), (CSDH x) expressed in cm;
The Capillary Sorption Absorption Height at which the material has absorbed y % of its capacity at 0 cm (i.e. of CSAC 0), (CSAH y) expressed in cm;
The Capillary Sorption Absorbent Capacity at a certain height z (CSAC z) expressed in units of g {of fluid}/g {of material}; especially at the height zero (CSAC 0), and at heights of 35 cm, 40 cm, etc
The Capillary Sorption Absorption Efficiency at a certain height z (CSAE. z) expressed in %, which is the ratio of the values for CSAC 0 and CSAC z.

If two materials are combined (such as the first being used as acquisition/distribution material, and the second being used as liquid storage material), the CSAC value (and hence the respective CSAE value) of the second material can be determined for the CSDH x value of the first material.

Teabag Centrifuge Capacity Test (TCC Test)

Whilst the TCC test has been developed specifically for superabsorbent materials, it can readily be applied to other absorbent materials.

The Teabag Centrifuge Capacity test measures the Teabag Centrifuge Capacity values, which are a measure of the retention of liquids in the absorbent materials.

The absorbent material is placed within a "teabag", immersed in a 0.9% by weight sodium chloride solution for 20 minutes, and then centrifuged for 3 minutes. The ratio of the retained liquid weight to the initial weight of the dry material is the absorptive capacity of the absorbent material.

Two litres of 0.9% by weight sodium chloride in distilled water is poured into a tray having dimensions 24 cm×30 cm×5 cm. The liquid filling height should be about 3 cm.

The teabag pouch has dimensions 6.5 cm×6.5 cm and is available from Teekanne in Dusseldorf, Germany. The pouch is heat sealable with a standard kitchen plastic bag sealing device (e.g. VACUPACK2 PLUS from Krups, Germany).

The teabag is opened by carefully cutting it partially, and is then weighed. About 0.200 g of the sample of the absorbent material, accurately weighed to +/−0.005 g, is placed in the teabag. The teabag is then closed with a heat sealer. This is called the sample teabag. An empty teabag is sealed and used as a blank.

The sample teabag and the blank teabag are then laid on the surface of the saline solution, and submerged for about 5 seconds using a spatula to allow complete wetting (the teabags will float on the surface of the saline solution but are then completely wetted). The timer is started immediately. After 20 minutes soaking time the sample teabag and the blank teabag are removed from the saline solution, and placed in a Bauknecht WS130, Bosch 772 NZK096 or equivalent centrifuge (230 mm diameter), so that each bag sticks to the outer wall of the centrifuge basket. The centrifuge lid is closed, the centrifuge is started, and the speed increased quickly to 1,400 rpm. Once the centrifuge has been stabilised at 1,400 rpm the timer is started. After 3 minutes, the centrifuge is stopped.

The sample teabag and the blank teabag are removed and weighed separately.

The Teabag Centrifuge Capacity (TCC) for the sample of absorbent material is calculated as follows:

TCC=[(sample teabag weight after centrifuging)−(blank teabag weight after centrifuging)−(dry absorbent material weight)] ÷(dry absorbent material weight).

Also, specific parts of the structures or the total absorbent articles can be measured, such as "sectional" cut outs, i.e. looking at parts of the structure or the total article, whereby the cutting is done across the full width of the article at determined points of the longitudinal axis of the article. In particular, the definition of the "crotch region" as described above allows to determine the "crotch region capacity". Other cut-outs can be used to determine a "basis capacity" (i.e. the amount of capacity contained in a unit area of the specific region of the article. Depending on the size of the unit area (preferably 2 cm by 2 cm) the defines how much averaging is taking place—naturally, the smaller the size, the less averaging will occur.

Ultimate Storage Capacity

In order to determine or evaluate the Ultimate Design Storage Capacity of an absorbent article, a number of methods have been proposed.

In the context of the present invention, it is assumed, that the Ultimate Storage Capacity of an article is the sum of the ultimate absorbent capacities of the individual elements or material. For these individual components, various well established techniques can be applied as long as these are applied consistently throughout the comparison. For example, the Tea Bag Centrifuge Capacity as developed and well established for superabsorbent polymers (SAP) can be used for such SAP materials, but also for others (see above).

Once the capacities for the individual materials are known, the total article capacity can be calculated by multiplying these values (in ml/g) with the weight of the material used in the article.

For materials having a dedicated functionality other than ultimate storage of fluids—such as acquisition layers and the like—the ultimate storage capacity can be neglected, either as such materials do in fact have only very low capacity values compared to the dedicated ultimate fluid storage materials, or as such materials are intended to not be loaded with fluid, and thus should release their fluid to the other ultimate storage materials.

Density/caliper/basis Weight Measurement

A specimen of a defined area such as by cutting with a sample cutter is weighed to at least 0.1% accuracy. Caliper is measured under an applied pressure of 550 Pa (0.08 psi) for an test area of 50 mm diameter. Basis weight as weight per unit area expressed in g/m2, caliper expressed in mm @ 550 Pa pressure, and density expressed in g/cm3 can be readily calculated.

What is claimed is:

1. Absorbent article comprising a fluid distribution member having a Capillary Sorption Absorption Height for 50% of its capacity at 0 cm (CSAH 50), further having a permeability at 100% saturation k(100), further having a permeability at 50% saturation k(50), further comprising a first fluid storage member in liquid communication with said fluid distribution member, said first fluid storage member having a Capillary Sorption Absorption Height for 50% of its capacity at 0 cm (CSAH 50), characterized in that said fluid distribution member has a permeability at 50% of its saturation k(50) which is more than about 14% of k(100), and in that said first fluid storage member has a CSAH 50 which is higher than the CSAH 50 of the fluid distribution member.

2. Absorbent article according to claim 1, wherein the first fluid storage member has a CSAH 50 of more than about 15 cm.

3. Absorbent article according to claim 2, wherein the first fluid storage member has a CSAH 50 of more than about 23 cm.

4. Absorbent article according to claim 3, wherein the first fluid storage member has a CSAH 50 of more than about 27 cm.

5. Absorbent article according to claim 4, wherein the first fluid storage member has a CSAH 50 of more than about 30 cm.

6. Absorbent article according to claim 5, wherein the first fluid storage member has a CSAH 50 of more than about 47 cm.

7. Absorbent article according to claim 1, wherein the Fluid distribution member has a k(50) value of more than about 18% of k(100).

8. Absorbent article according to claim 7, wherein the Fluid distribution member has a k(50) value of more than about 25% of k(100).

9. Absorbent article according to claim 8, wherein the fluid distribution member has a k(50) value of more than about 35% of k(100).

10. Absorbent article according to claim 1, wherein the fluid distribution member has a permeability at 30% of its saturation k(30) which is more than about 3% of k(100).

11. Absorbent article according to claim 10, wherein the fluid distribution member has a k(30) value, which is more than about 5% of k(100).

12. Absorbent article according to claim 1, wherein the fluid distribution member has a CSDH 50 value of less than about 150 cm.

13. Absorbent article according to claim 12, wherein the Fluid distribution member has a CSDH 50 value of less than about 100 cm.

14. Absorbent article according to claim 13, wherein the Fluid distribution member has a CSDH 50 value of less than about 75 cm.

15. Absorbent article according to claim 14, wherein the Fluid distribution member has a CSDH 50 value of less than about 50 cm.

16. Absorbent article according to claim 1, wherein the fluid distribution member comprises an open celled foam.

17. Absorbent article according to claim 16, wherein the fluid distribution member expands upon wetting.

18. Absorbent article according to any of claim 16, wherein the fluid distribution member re-collapses upon loosing liquid.

19. Absorbent article according to claim 1, further characterized in that said first fluid storage member comprises a hydrophilic, flexible polymeric foam structure of interconnected open-cells.

20. Absorbent article according to claim 19, further characterized in that said first fluid storage member expands upon wetting.

21. Absorbent article according to claim 20, whereby said first fluid storage member re-collapses upon loosing liquid.

22. Fluid handling member according to claim 21, whereby said hydrophilic, flexible polymeric foam has a capillary collapse pressure as defined herein of at least about 15 cm.

23. Absorbent article according to claim 1, further comprising a second liquid storage region, whereby both liquid storage regions are in liquid communication with said fluid distribution member.

24. Absorbent article according claim 23, wherein at least one of said liquid storage regions comprises material exhibiting a Capillary Sorption Absorption Height at 50% of its maximum capacity (CSAH 50) of at least about 40 cm.

25. Absorbent article according to claim 1, further comprising a crotch region and one or more waist regions, whereby said crotch region has a lower ultimate fluid storage capability than said one or more waist regions together.

26. An absorbent article according to claim 25, wherein said crotch region has an ultimate fluid storage basis capacity of less than 0.9 times the average ultimate fluid storage basis capacity of the absorbent core.

27. An absorbent article according to claim 26, wherein said crotch region has an ultimate fluid storage basis capacity of less than 0.5 times the average ultimate fluid storage basis capacity of the absorbent core.

28. An absorbent article according to claim 27, wherein said crotch region has an ultimate fluid storage basis capacity of less than 0.3 times the average ultimate fluid storage basis capacity of the absorbent core.

29. An absorbent article according to claim 25, wherein said crotch region has a sectional ultimate fluid storage capacity of less than 49% of the total core ultimate fluid storage capacity.

30. An absorbent article according to claim 29, wherein said crotch region has a sectional ultimate fluid storage capacity of less than 41% of the total core ultimate fluid storage capacity.

31. An absorbent article according to claim 30, wherein said crotch region has a sectional ultimate fluid storage capacity of less than 23% the total core ultimate fluid storage capacity.

32. An absorbent article according to claim 25, further characterised in that at least 50% of the area of said crotch region contain essentially no ultimate storage capacity.

33. An absorbent article according to claim 25, further characterised in that less than 50% of said ultimate storage capacity are positioned forwardly from the crotch zone in the front half of the article, and more than 50% of said ultimate storage capacity are positioned in the rear half of the article.

34. An absorbent article according to claim 33, wherein less than 33% of said ultimate storage capacity are positioned forwardly from the crotch zone/in the front half of the article, and more than 67% of said ultimate storage capacity are positioned in the rear half of the article.

35. An absorbent article according to claim 1, further characterized in that it comprises an ultimate liquid storage material providing at least 80% of the total ultimate storage capacity of the absorbent core.

36. An absorbent article according to claim 32, further characterized in that comprises a ultimate liquid storage material providing at least 90% of the total ultimate storage capacity of the absorbent core.

\* \* \* \* \*

UNITED STATES PATENT AND TRADEMARK OFFICE
CERTIFICATE OF CORRECTION

PATENT NO.     : 6,570,057 B1
DATED          : May 27, 2003
INVENTOR(S)    : Schmidt et al.

It is certified that error appears in the above-identified patent and that said Letters Patent is hereby corrected as shown below:

<u>Title page, Item [54] and Column 1, line 3,</u>
Title, please delete "SUR-SATURATION" and insert therefore
-- SUB-SATURATION --.

<u>Column 12,</u>
Line 60, after "CELBOND®", please delete ")" (right parenthesis).

<u>Column 28,</u>
Line 53, please delete "Oreg." and insert therefor -- OR --.

<u>Column 29,</u>
Line 55, please delete "HIGH" and insert therfor -- High --.

<u>Column 34,</u>
Line 7, after "by:" please insert carriage return.
Line 8, after "composition;" please insert carriage return.

<u>Column 35,</u>
Line 21, after "50 μm." please insert carriage return.
Line 63, please delete space after "(" (left parenthesis).

<u>Column 57,</u>
Line 19, before "(i.e." please delete "m".

<u>Column 64,</u>
Line 45, please delete both occurrences of "Coming" and insert therefor -- Corning --.

UNITED STATES PATENT AND TRADEMARK OFFICE
CERTIFICATE OF CORRECTION

PATENT NO. : 6,570,057 B1
DATED : May 27, 2003
INVENTOR(S) : Schmidt et al.

It is certified that error appears in the above-identified patent and that said Letters Patent is hereby corrected as shown below:

<u>Column 73,</u>
Line 25, after "(CSAE", please delete "." (the period).

Signed and Sealed this

Eighth Day of June, 2004

JON W. DUDAS
*Acting Director of the United States Patent and Trademark Office*